(12) United States Patent
Falck et al.

(10) Patent No.: US 10,995,056 B2
(45) Date of Patent: May 4, 2021

(54) DIRECT C—H AMINATION AND AZA-ANNULATION

(71) Applicants: The Board of Regents of the University of Texas System, Austin, TX (US); William Marsh Rice University, Houston, TX (US)

(72) Inventors: John R. Falck, Dallas, TX (US); Mahesh P. Paudyal, Fort Worth, TX (US); László Kürti, Houston, TX (US)

(73) Assignees: The Board of Regents of the University of Texas System, Austin, TX (US); William Marsh Rice University, Houston, TX (US)

( * ) Notice: Subject to any disclaimer, the term of this patent is extended or adjusted under 35 U.S.C. 154(b) by 0 days.

(21) Appl. No.: 16/316,692

(22) PCT Filed: Jul. 11, 2017

(86) PCT No.: PCT/US2017/041497
§ 371 (c)(1),
(2) Date: Jan. 10, 2019

(87) PCT Pub. No.: WO2018/013540
PCT Pub. Date: Jan. 18, 2018

(65) Prior Publication Data
US 2019/0152892 A1    May 23, 2019

Related U.S. Application Data

(60) Provisional application No. 62/360,859, filed on Jul. 11, 2016.

(51) Int. Cl.
| | | |
|---|---|---|
| C08F 4/64 | (2006.01) |
| C08F 4/60 | (2006.01) |
| C08F 10/00 | (2006.01) |
| C08F 4/619 | (2006.01) |
| C08F 110/02 | (2006.01) |
| C07C 209/02 | (2006.01) |
| C07D 211/02 | (2006.01) |
| C07C 213/02 | (2006.01) |
| C07J 41/00 | (2006.01) |
| C07C 227/06 | (2006.01) |
| C07D 489/02 | (2006.01) |
| C07D 215/06 | (2006.01) |
| C07D 215/20 | (2006.01) |
| C07D 215/18 | (2006.01) |
| C07D 215/12 | (2006.01) |
| C07D 265/36 | (2006.01) |
| C07D 209/08 | (2006.01) |
| C07D 223/16 | (2006.01) |
| C07D 207/06 | (2006.01) |
| C07D 209/58 | (2006.01) |
| C07D 203/10 | (2006.01) |
| C07C 209/00 | (2006.01) |
| C07C 303/30 | (2006.01) |
| C07D 211/12 | (2006.01) |
| C07D 209/96 | (2006.01) |
| C07J 1/00 | (2006.01) |

(52) U.S. Cl.
CPC .......... *C07C 209/02* (2013.01); *C07C 209/00* (2013.01); *C07C 213/02* (2013.01); *C07C 227/06* (2013.01); *C07C 303/30* (2013.01); *C07D 203/10* (2013.01); *C07D 207/06* (2013.01); *C07D 209/08* (2013.01); *C07D 209/58* (2013.01); *C07D 209/96* (2013.01); *C07D 211/02* (2013.01); *C07D 211/12* (2013.01); *C07D 215/06* (2013.01); *C07D 215/12* (2013.01); *C07D 215/18* (2013.01); *C07D 215/20* (2013.01); *C07D 223/16* (2013.01); *C07D 265/36* (2013.01); *C07D 489/02* (2013.01); *C07J 41/0005* (2013.01); *C07C 2601/02* (2017.05); *C07C 2603/74* (2017.05); *C07J 1/0059* (2013.01)

(58) Field of Classification Search
CPC .... C08F 4/64; C08F 4/60; C08F 10/00; C08F 4/61908; C08F 110/02
See application file for complete search history.

(56) References Cited

FOREIGN PATENT DOCUMENTS

| WO | WO 2015/000715 | 1/2015 |
| WO | WO 2015/103505 | 7/2015 |

OTHER PUBLICATIONS

Label et al., N-Tosyloxycarbamates as a Source of Metal Nitrenes: Rhodium-Catalyzed C—H Insertion and Aziridination Reactions, Journal of the American Chemical Society, vol. 127, No. 41, pp. 14198-14199 (Year: 2005).*

Baburaj et al., "N-amination of amino acids and its derivatives using N-Boc-O-tosyl hydroxylamine as an efficient NH-Boc transfer reagent: electrophilic amination," *Tetrahedron Letters*, 53:2292-2294, 2012.

(Continued)

*Primary Examiner* — Brenda L Coleman
(74) *Attorney, Agent, or Firm* — Parker Highlander PLLC

(57) ABSTRACT

In some aspects, the present disclosure provides methods of aminating an aromatic compound comprising reacting an aminating agent with an aromatic compound in the presence of a rhodium catalyst. In some embodiments, the methods may comprise aminating an aromatic compound which contains multiple different functional groups. The methods described herein may also be used to create bicyclic system comprising reacting an intramolecular aminating agent with an aromatic ring to obtain a second ring containing a nitrogen atom. In another aspect, the methods described herein may also be used to create a cyclic aliphatic cyclic/poly cyclic amine system comprising a reacting an intramolecular aminating agent by insertion into a C(sp3)-H bond.

20 Claims, 11 Drawing Sheets

(56) References Cited

OTHER PUBLICATIONS

Brasche and Buchwald, "C—H functionalization/C—N bond formation: copper-catalyzed synthesis of benzimidazoles from amidines," *Angew. Chem., Int. Ed.*, 47(10):1932-1934, 2008.
Chen et al., "Selective Catalytic Hydrogenation of Heteroarenes with N-Graphene-Modified Cobalt Nanoparticles (Co3O4—Co/NGr@α-Al2O3)," *J. Am. Chem. Soc.*, 137(36):11718-11724, 2015.
Chen et al., "Transition metal-catalyzed C—H bond functionalizations by the use of diverse directing groups," *Org. Chem. Front.*, 2:1107-1295, 2015.
Davies and Dai, "Synthetic Reactions via C—H Bond Activation: Carbene and Nitrene C—H Insertion," *Comprehensive Organometallic Chemistry III.*, 10:167-212, 2007.
Du et al., "Rhodium-catalyzed direct amination of arenes with nitrosobenzenes: a new route to diarylamines," *Chem. Eur. J.*, 20:5727-5731, 2014.
Greulich et al., "N-aminopyridinium salts as precursors for N-centered radicals—direct amidation of arenes and heteroarenes," *Org. Lett.*, 17:254-257, 2015.
Hartwig, "Evolution of a fourth generation catalyst for the amination and thioetherification of aryl halides," *Acc. Chem. Res.*, 41(11):1534-1544, 2008.
Inamoto et al., "Palladium-catalyzed C—H activation/intramolecular amination reaction: a new route to 3-aryl/alkylindazoles," *Org. Lett.*, 9(15):2931-2934, 2007.
Inamoto et al., "Palladium-catalyzed intramolecular amidation of C(sp2)—H bonds: synthesis of 4-aryl-2-quinolinones," *J. Org. Chem.*, 75(11):3900-3903, 2010.
Kunz et al., "Renaissance of Ullmann and Goldberg Reactions—Progress in Copper Catalyzed C—N-, C—O- and C—S-Coupling," *Synlett*, 15:2428-2439, 2003.
Lundgren and Stradiotto, "Recent advances in the Buchwald-Hartwig amination reaction enabled by the application of sterically demanding phosphine ancillary ligands," *Aldrichimica Acta*, 45:59-65, 2012.
Maejima et al., "One-pot aromatic amination based on carbon-nitrogen coupling reaction between aryl halides and azido compounds," *Tetrahedron*, 68(6):1712-1722, 2012.
Martinez-Barrasa et al., "The first example of an intramolecular Westphal reaction. Synthesis of a new aza-quinolizinium type system," *Tetrahedron Letters*, 40:4115-4118, 1999.
Nageli et al., "Rhodium(II)-Catalyzed CH Insertions with {[(4-Nitrophenyl) sulfonyl]iminol}phenyl-$\lambda^3$-iodane," *Helvetica Chimica Acta*, 80:1087-1105, 1997.
Park et al., "Mechanistic studies of the rhodium-catalyzed direct C—H amination reaction using azides as the nitrogen source," *J. Am. Chem. Soc.*, 136:2492-2502, 2014.
Park et al., "Mechanistic studies on the Rh(III)-mediated amido transfer process leading to robust C—H amination with a new type of amidating reagent," *J. Am. Chem. Soc.*, 137(13):4534-4542, 2015.
Park et al., "Rhodium-catalyzed direct amination of arene C—H bonds using azides as the nitrogen source," *Org. Synth.*, 91:52-59, 2014.
Paudyal et al., "Dirhodium-catalyzed C—H arene amination using hydroxylamines," *Science*, 353(6304):1144-1147, 2016.
PCT International Preliminary Report on Patentability issued in International Application No. PCT/US2017/041497, dated Jan. 24, 2019.
PCT International Search Report and Written Opinion issued in International Application No. PCT/US2017/041497, dated Nov. 20, 2017.
Romero et al., "Site-selective arene C—H amination via photoredox catalysis," *Science*, 349:1326-1330, 2015.
Shin et al., "Direct C—H amination of arenes with alkyl azides under rhodium catalysis," *Angew. Chem. Int. Ed.*, 52:8031-8036, 2013.
Shin et al., "Transition-metal-catalyzed C—N bond forming reactions using organic azides as the nitrogen source: a journey for the mild and versatile C—H amination,"*Acc. Chem. Res.*, 48(4):1040-1052, 2015.
Shrestha et al., "Sterically controlled, palladium-catalyzed intermolecular amination of arenes," *J. Am. Chem. Soc.*, 135:8480-8483, 2013.
Starkov et al., "Electrophilic amination: the case of nitrenoids," *Chem.—Eur. J.*, 21:5278-5300, 2015.
Sun and Gu, "Decarboxylative Alkynyl Termination of Palladium-Catalyzed Catellani Reaction: A Facile Synthesis of α-Alkynyl Anilines via Ortho C—H Amination and Alkynylation," *Org. Lett.*, 17:2222-2225, 2015.
Surry and Buchwald, "Biaryl phosphane ligands in palladium-catalyzed amination," *Angew. Chem., Int. Ed.*, 47:6338-6361, 2008.
Suzuki et al., "Direct synthesis of N—H carbazoles via iridium(III)-catalyzed intramolecular C—H amination," *Org. Lett.*, 17:1597-1600, 2015.
Takamatsu et al., "Synthesis of indolines by copper-mediated intramolecular aromatic C-h amination," *J. Org. Chem.*, 80:3242-3249, 2015.
Takemoto and Miyabe, "C—N Bond Formation through Amination," *Comprehensive Organometallic Chemistry III*, 10:695-724, 2007.
Tamura et al., "O-Arenesulfonyl-N-alkylhydroxylamines as Aminating Reagents," *Chemical and Pharmaceutical Bulletin*, 30:1221-1224, 1982.
Tsang et al., "Combined C—H functionalization/C—N bond formation route to carbazoles," *J. Am. Chem. Soc.*, 127:14560-14561, 2005.
Xia and Taillefer, "A very simple copper-catalyzed synthesis of anilines by employing aqueous ammonia," *Angew. Chem., Int. Ed.*, 48:337-339, 2009.
Xue et al., "RhIII—Catalysed Hydrazine—Directed C(sp2)—H Amination of Phenidones with N-Alkyl-O-benzoyl-hydroxylamines," *Eur. J. Org. Chem.*, 2014(33):7481-7488, 2014.
Yan et al., "Nickel-catalyzed direct amination of arenes with alkylamines," *Org. Lett.*, 17:2482-2485, 2015.
Zalatan et al., "Understanding the differential performance of Rh2(esp)2 as a catalyst for C—H amination," *Journal of the American Chemical Society*, 131:7558-7559, 2009.
Zeng et al., "An efficient copper-catalyzed synthesis of anilines by employing aqueous ammonia," *Org. Biomol. Chem.*, 9:8224-8227, 2011.

\* cited by examiner

DIRECT C—H AMINATION AND AZA-ANNULATION

This application is a national phase application under 35 U.S.C. § 371 of International Application No. PCT/US2017/041497, filed Jul. 11, 2017, which claims the benefit of priority to U.S. Provisional Application Ser. No. 62/360,859, filed on Jul. 11, 2016, the entire contents of each of which are hereby incorporated by reference.

The invention was made with government support under Grant Nos. HL034300, HL111392, DK038226, and R01GM11460901 awarded by the National Institutes of Health and CHE-1455335 awarded by the National Science Foundation. The government has certain rights in the invention.

BACKGROUND

1. Field

The present disclosure relates generally to the field of synthetic methodology. More particularly, it concerns methods for directly aminating CH bonds in an arene or forming a azaarene. In other embodiments, the methods relate to the intramolecular insertion of an alkylnitrogen into sp$^3$ C—H bonds.

2. Description of Related Art

Arylamine motifs (Hili and Yudin, 2006 and Ricci, 2008) are prevalent in natural products, pharmaceuticals, agrochemicals, functional materials, and dyestuffs as well as many synthetic reagents and catalysts (Angelici, 1990, Dalla Cort et al., 2005 and Candeias et al., 2009). The traditional methodologies for creating an aryl amine from a corresponding C(sp$^2$)-H bond involve multi-step sequences and/or harsh conditions (Hartwig et al., 2007, Xie et al., 2013 and Yu, et al., 2013). The initial product of these traditional methodologies (nitro, azide, azo, nitroso, chloronitroso, amide/imide/sulfonamide, or imine) requires an additional step(s) before arriving at a free amine (Hartwig et al., 2007). The amination of organic anions is a useful and direct alternative (Daskapan, 2011), but is generally restricted to the introduction of —NR$_1$R$_2$ when R$_1$ and R$_2$ are not H and is not applicable to base sensitive substrates. The studies of Ullman and Goldberg into metal-mediated arene C(sp$^2$)-N bond formation at the beginning of the 20th century were harbingers (Kunz et al., 2003) of more efficient palladium catalyzed cross-couplings between aromatic halides/sulfonates and ammonia or nitrogen surrogates developed independently by Hartwig (Hartwig, 2008) and Buchwald (Surry and Buchwald, 2008) in the early 1990s. These methods have been further optimized to include improvements, up to the present time, with the aim of mitigating the original stringent Hartwig-Buchwald reaction conditions (Xia and Taillefer, 2009, Zeng et al., 2011, Lundgren and Stradiotto, 2012 and Maejima et al., 2012). Regardless of the conditions used in these protocols, however, the methodologies share one significant restriction, the need for a pre-functionalized arene.

Recently, research has been towards catalytic, direct arene aminations (Davies and Dai, 2007, Takemoto and Miyabe, 2007 and Starkov et al., 2015). Many elegant atom- and step-efficient protocols have been introduced, but most require a directing group while others may also need an excess of arene, high temperatures, or generate amides, imides, and sulfomamides instead of free amines (Tsang et al., 2005, Inamoto et al., 2007, Brasche and Buchwald, 2008, Inamoto et al., 2010, Shrestha et al., 2013, Xue et al. 2014, Chen et al., 2015, Park et al., 2015, Shin et al., 2015, Sun and Gu, 2015, Suzuki et al., 2015 and Takamatsu et al., 2015). A noteworthy exception is the photoredox driven process of Nicewicz (Romero et al., 2015) and colleagues that circumvents many of the preceding limitations, but this methodology has not been demonstrated in the presence of alcohol substituents or on a multigram scale. It also utilizes an enriched oxygen atmosphere which, when in contact with organic material, might be hazardous. As can be seen, the current methods have numerous limitations and thus there remains a need for new CH amination reactions which do not require directing groups or harsh conditions.

SUMMARY

In some aspects, the present disclosure provides methods of obtaining an amino aromatic compound comprising reacting an aromatic compound with an aminating agent in the presence of a rhodium catalyst, wherein the aminating agent is a compound of the formula:

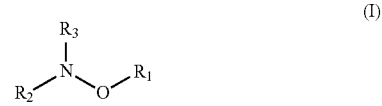

(I)

wherein:
R$_1$ is an arylsulfonyl$_{(C \leq 18)}$ or substituted arylsulfonyl$_{(C \leq 18)}$;
R$_2$ is hydrogen, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, alkynyl$_{(C \leq 12)}$, substituted alkynyl$_{(C \leq 12)}$, aryl$_{(C \leq 12)}$, substituted aryl$_{(C \leq 12)}$, aralkyl$_{(C \leq 12)}$, substituted aralkyl$_{(C \leq 12)}$, heteroaryl$_{(C \leq 12)}$, substituted heteroaryl$_{(C \leq 12)}$, or a monovalent amino protecting group, or R$_2$ and R$_3$ are taken together and are a divalent amino protecting group; and
R$_3$ is hydrogen, a monovalent amino protecting group, or R$_3$ and R$_2$ are taken together and are a divalent amino protecting group.

In some embodiments, the aminating agent is further defined as:

(II)

wherein:
R$_1$ is an arylsulfonyl(cis, or substituted arylsulfonyl$_{(C \leq 18)}$;
R$_2$ is hydrogen, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, alkynyl$_{(C \leq 12)}$, substituted alkynyl$_{(C \leq 12)}$, aryl$_{(C \leq 12)}$, substituted aryl$_{(C \leq 12)}$, aralkyl$_{(C \leq 12)}$, substituted aralkyl$_{(C \leq 12)}$, heteroaryl$_{(C \leq 12)}$, substituted heteroaryl$_{(C \leq 12)}$, or a monovalent amino protecting group.
R$_2$ may be hydrogen, alkyl$_{(C \leq 12)}$, substituted alkyl$_{(C \leq 12)}$, cycloalkyl$_{(C \leq 12)}$, substituted cycloalkyl$_{(C \leq 12)}$, aryl$_{(C \leq 12)}$, substituted aryl$_{(C \leq 12)}$, or a monovalent amino protecting group. In some embodiments, R$_2$ is hydrogen. In other embodiments, R$_2$ is alkyl$_{(C \leq 12)}$ or substituted alkyl$_{(C \leq 12)}$ such as methyl or n-butyl. In still other embodiments, R$_2$ is a monovalent amino protecting group such as t-butyloxy-carbonyl. $R_1$ may be an arylsulfonyl$_{(C \leq 18)}$ such as p-toluenesulfonyl or 2,4,6-trimethylphenylsulfonyl. In some aspects, the aminating agent is a compound of the formula:

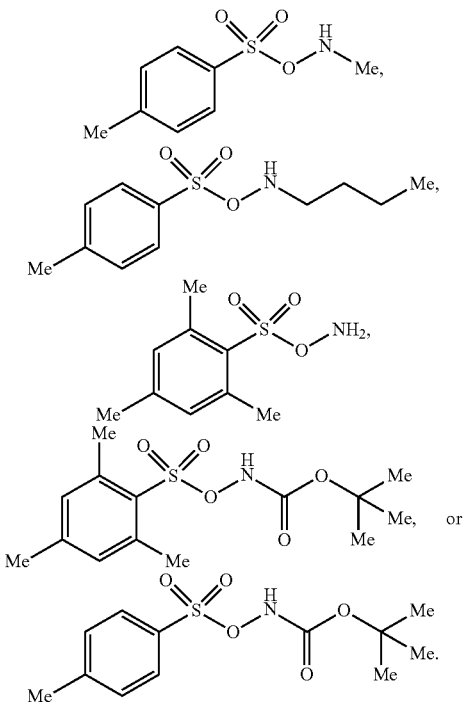

In some embodiments, the rhodium catalyst is a dirhodium catalyst such as a tetravalent dirhodium catalyst. In some embodiments, the rhodium catalyst of the formula: $Rh_2(L_1)_4$ or $Rh_2(L_2)_2$, wherein:
$L_1$ is an acylate$_{(C \leq 12)}$ or a substituted acylate$_{(C \leq 12)}$; and
$L_2$ is a diacylate$_{(C \leq 18)}$ or a substituted diacylate$_{(C \leq 18)}$.
In some embodiments, $L_1$ is acylate$_{(C \leq 12)}$ such as acetate or octanoate or a substituted acylate$_{(C \leq 12)}$ such as trifluoroacetate. In other embodiments, $L_2$ is diacylate$_{(C \leq 18)}$ such as:

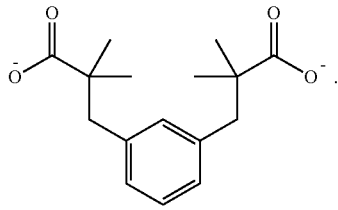 [SMILES: CC(C)(Cc1cccc(CC(C)(C)C(=O)O)c1)C(=O)O]

The rhodium catalyst may be $Rh_2(OAc)_4$, $Rh_2(TFA)_4$, $Rh_2(C_8H_{15}O_2)_4$, or $Rh_2(esp)_2$. In some embodiments, the rhodium catalyst is $Rh_2(esp)_2$.

In another embodiment, the aromatic compound comprises from 6 carbon atoms to 30 carbon atoms. In some embodiments, the aromatic compound comprises from 6 carbon atoms to 18 carbon atoms or from 6 carbon atoms to 12 carbon atoms. The aromatic compound may be an aryl compound containing 1-6 rings or an aryl compound containing 1-3 rings. In some embodiments, the aromatic compound is not substituted. In other embodiments, the aromatic compound is substituted. The aromatic compound may be substituted with 1-10 groups selected from amino, carboxy, cyano, halo, hydroxy, hydroxyamino, hydroxysulfonyl, nitro, aminosulfonyl, or acyl$_{(C \leq 6)}$, alkoxy$_{(C \leq 6)}$, acyloxy$_{(C \leq 6)}$, amido$_{(C \leq 6)}$, alkylamino$_{(C \leq 6)}$, dialkylamino$_{(C \leq 6)}$, or a substituted version of these six groups. In some embodiments, the aromatic compound is substituted with 1, 2, or 3 groups selected from bromo, fluoro, methoxy, ethoxy, propoxy, or oxo.

In another embodiment, the present methods may further comprise reacting the aromatic compound with the aminating compound in a reaction mixture. The reaction mixture may comprise an organic solvent. In some embodiments, the organic solvent contains one or more halogen atoms. The organic solvent may be an alcohol$_{(C1-8)}$ such as 2,2,2-trifluoroethanol. In other embodiments, the organic solvent is a mixture of trifluoroethanol and a second organic solvent. The second organic solvent may be a haloalkane$_{(C1-8)}$ or an alcohol$_{(C1-8)}$. In some embodiments, the second organic solvent is dichloromethane or methanol.

In another embodiment, the reaction mixture has a temperature from about −30° C. to about 30° C. In some embodiments, the methods comprise adding from about 0.5 to about 5 equivalents of the aminating compound relative to the aromatic compound to the reaction mixture. In some embodiments, the methods comprise adding from about 1 equivalent to about 2 equivalents of the aminating compound. The methods may comprise adding about 1.5 equivalent of the aminating compound. The methods comprise adding from about 0.05 mol % to about 10 mol % of the rhodium catalyst. In some embodiments, the methods comprise adding from about 0.1 mol % to about 5 mol % of the rhodium catalyst. The methods may comprise adding from about 0.5 mol % to about 2.5 mol % of the rhodium catalyst. In some embodiments, the methods comprise adding about 2 mol % of the rhodium catalyst.

In another embodiment, the methods further comprise adding a deprotecting agent. The deprotecting agent may be an acid such as trifluoroacetic acid. In some embodiments, the deprotecting agent is added when the aminating agent contains a monovalent amino protecting group or a divalent amino protecting group.

In another aspect, the present disclosure provides methods of preparing an aza-arene comprising:
(A) converting a reactive functional group on an branched chain, wherein the branched chain may optionally contain 1, 2, or 3 heteroatoms selected from nitrogen, oxygen, or sulfur atoms within the chain, attached to an aromatic compound to a group of the formula:

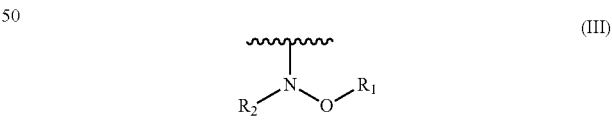

wherein:
$R_1$ is an arylsulfonyl$_{(C \leq 18)}$ or substituted arylsulfonyl$_{(C \leq 18)}$; and
$R_2$ is hydrogen, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, alkynyl$_{(C \leq 12)}$, substituted alkynyl$_{(C \leq 12)}$, aryl$_{(C \leq 12)}$, substituted aryl$_{(C \leq 12)}$, aralkyl$_{(C \leq 12)}$, substituted aralkyl$_{(C \leq 12)}$, heteroaryl$_{(C \leq 12)}$, substituted heteroaryl$_{(C \leq 12)}$, or a monovalent amino protecting group; and
(B) reacting the aromatic compound with a rhodium catalyst to obtain an aza-arene.

In some embodiments, the reactive functional group is a hydroxy group. The reactive functional group may be an activated hydroxy group. In some embodiments, the reactive functional group is converted by nucleophilic displacement such as through a Mitsunobu reaction.

In some embodiments, the branched chain contains 1 or 2 heteroatoms. The branched chain may contain 1 heteroatom such as —O—. In some embodiments, the branched chain comprises 1, 2, 3, or 4 atoms between the carbon atom attached to the reactive functional group and the attachment point of the branched chain to the aromatic compound. In some embodiments, the branched chain is attached to a carbon atom which is a part of an aromatic ring within the aromatic compound. In other embodiments, the branched chain is attached to a carbon atom on an aliphatic group wherein the carbon atom is within 1, 2, or 3 atoms of an aromatic ring within the aromatic compound. In some embodiments, the aromatic compound is further defined as:

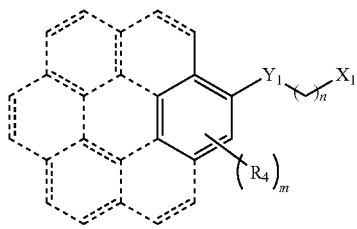

(IV)

wherein:
n is, 0, 1, 2, 3, or 4;
$Y_1$ is —CH$_2$—, —NR$_a$—, or —O—; wherein:
   $R_a$ is hydrogen, alkyl$_{(C≤6)}$, or alkyl$_{(C≤6)}$;
$X_1$ is the reactive functional group;
m is an integer between 1 and 10; and
$R_4$ is amino, cyano, halo, hydroxy, hydroxysulfonyl, nitro, aminosulfonyl, acyl$_{(C≤6)}$, alkoxy$_{(C≤6)}$, acyloxy$_{(C≤6)}$, amido$_{(C≤6)}$, alkylamino$_{(C≤6)}$, dialkylamino$_{(C≤6)}$, or a substituted version of the last six groups.

In some embodiments, n is 0, 1, or 2. The variable, n, may be 1. The variable, n, may be 2.

In some embodiments, the rhodium catalyst is a dirhodium catalyst such as a tetravalent dirhodium catalyst. In some embodiments, the rhodium catalyst of the formula: Rh$_2$(L$_1$)$_4$ or Rh$_2$(L$_2$)$_2$, wherein:
$L_1$ is an acylate$_{(C≤12)}$ or a substituted acylate$_{(C≤12)}$; and
$L_2$ is a diacylate$_{(C≤18)}$ or a substituted diacylate$_{(C≤18)}$.

In some embodiments, $L_1$ is acylate$_{(C≤12)}$ such as acetate or octanoate or a substituted acylate$_{(C≤12)}$ such as trifluoroacetate. In other embodiments, $L_2$ is diacylate$_{(C≤18)}$ such as:

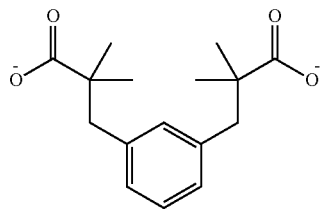

The rhodium catalyst may be Rh$_2$(OAc)$_4$, Rh$_2$(TFA)$_4$, Rh$_2$(C$_8$H$_{15}$O$_2$)$_4$, or Rh$_2$(esp)$_2$. In some embodiments, the rhodium catalyst is Rh$_2$(esp)$_2$.

In another embodiment, the aromatic compound comprises from 6 carbon atoms to 30 carbon atoms. In some embodiments, the aromatic compound comprises from 6 carbon atoms to 18 carbon atoms or from 6 carbon atoms to 12 carbon atoms. The aromatic compound may be an aryl compound containing 1-6 rings or an aryl compound containing 1-3 rings. In some embodiments, the aromatic compound is not substituted. In other embodiments, the aromatic compound is substituted. The aromatic compound may be substituted with 1-10 groups selected from amino, carboxy, cyano, halo, hydroxy, hydroxyamino, hydroxysulfonyl, nitro, aminosulfonyl, or acyl$_{(C≤6)}$, alkoxy$_{(C≤6)}$, acyloxy$_{(C≤6)}$, amido$_{(C≤6)}$, alkylamino$_{(C≤6)}$, dialkylamino$_{(C≤6)}$, or a substituted version of these six groups. In some embodiments, the aromatic compound is substituted with 1, 2, or 3 groups selected from bromo, fluoro, methoxy, ethoxy, propoxy, or oxo.

In another embodiment, the present methods may further comprise reacting the aromatic compound with the aminating compound in a reaction mixture. The reaction mixture may comprise an organic solvent. In some embodiments, the organic solvent contains one or more halogen atoms. The organic solvent may be an alcohol$_{(C1-8)}$ such as 2,2,2-trifluoroethanol. In other embodiments, the organic solvent is a mixture of trifluoroethanol and a second organic solvent. The second organic solvent may be a haloalkane$_{(C1-8)}$ or an alcohol$_{(C1-8)}$. In some embodiments, the second organic solvent is dichloromethane or methanol.

In another embodiment, the reaction mixture has a temperature from about −30° C. to about 30° C. In some embodiments, the methods comprise adding from about 0.5 to about 5 equivalents of the aminating compound relative to the aromatic compound to the reaction mixture. In some embodiments, the methods comprise adding from about 1 equivalent to about 2 equivalents of the aminating compound. The methods may comprise adding about 1.5 equivalent of the aminating compound. The methods comprise adding from about 0.05 mol % to about 10 mol % of the rhodium catalyst. In some embodiments, the methods comprise adding from about 0.1 mol % to about 5 mol % of the rhodium catalyst. The methods may comprise adding from about 0.5 mol % to about 2.5 mol % of the rhodium catalyst. In some embodiments, the methods comprise adding about 2 mol % of the rhodium catalyst.

In another embodiment, the methods further comprise adding a deprotecting agent. The deprotecting agent may be an acid such as trifluoroacetic acid. In some embodiments, the deprotecting agent is added when the aminating agent contains a monovalent amino protecting group or a divalent amino protecting group. In other embodiments, the deprotecting agent is added when $R_2$ is a monovalent amino protecting group.

In still yet another aspect, the present disclosure provides methods of preparing a N-heterocycloalkane group comprising:
(A) reacting a reactant compound, wherein the reactant compound contains a reactive functional group attached to an aliphatic linker and a second aliphatic or aromatic group; with an aminating agent of the formula:

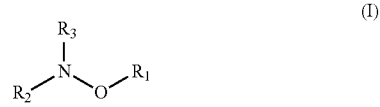

(I)

wherein:
R$_1$ is an arylsulfonyl$_{(C≤18)}$ or substituted arylsulfonyl$_{(C≤18)}$;
R$_2$ is hydrogen, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, alkynyl$_{(C≤12)}$, substituted alkynyl$_{(C≤12)}$, aryl$_{(C≤12)}$, substituted aryl$_{(C≤12)}$, aralkyl$_{(C≤12)}$, substituted aralkyl$_{(C≤12)}$, or a monovalent amino protecting group; and
R$_3$ is hydrogen, a monovalent amino protecting group; and
under conditions sufficient to displace the reactive functional group to obtain an aminating compound with the group:

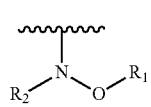

(III)

wherein:
R$_1$ is an arylsulfonyl$_{(C≤18)}$ or substituted arylsulfonyl$_{(C≤18)}$; and
R$_2$ is hydrogen, alkyl$_{(C≤12)}$, substituted alkyl$_{(C≤12)}$, cycloalkyl$_{(C≤12)}$, substituted cycloalkyl$_{(C≤12)}$, alkenyl$_{(C≤12)}$, substituted alkenyl$_{(C≤12)}$, alkynyl$_{(C≤12)}$, substituted alkynyl$_{(C≤12)}$, aryl$_{(C≤12)}$, substituted aryl$_{(C≤12)}$, aralkyl$_{(C≤12)}$, substituted aralkyl$_{(C≤12)}$, or a monovalent amino protecting group; and (B) reacting the aminating compound prepared in step (A) in the presence of a rhodium catalyst and an acid to obtain a compound containing a N-heterocycloalkyl group wherein the N-heterocycloalkyl group contains 3 to 10 ring atoms and a bond is formed between a second carbon atom of the reactant compound and the nitrogen atom of the group of formula III.

The reactant compound may comprise 3 carbon atoms to 30 carbon atoms. In some embodiments, the reactant compound comprises 6 carbon atoms to 24 carbon atoms. In some embodiments, the reactant compound comprises 6 carbon atoms to 18 carbon atoms. The reactant compound may be further defined as:

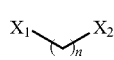

(V)

wherein:
X$_1$ is a reactive functional group;
X$_2$ is alkyl$_{(C≤18)}$, cycloalkyl$_{(C≤18)}$, alkenyl$_{(C≤18)}$, alkynyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, alkoxy$_{(C≤18)}$, cycloalkoxy$_{(C≤18)}$, alkenyloxy$_{(C≤18)}$, alkynyloxy$_{(C≤18)}$, aryloxy$_{(C≤18)}$, aralkyloxy$_{(C≤18)}$, heteroaryloxy$_{(C≤18)}$, heteroaralkyloxy$_{(C≤18)}$, heterocycloalkoxy$_{(C≤18)}$, alkylamino$_{(C≤18)}$, dialkylamino$_{(C≤18)}$, cycloalkylamino$_{(C≤18)}$, dicycloalkylamino$_{(C≤18)}$, alkenylamino$_{(C≤18)}$, alkynylamino$_{(C≤18)}$, arylamino$_{(C≤18)}$, aralkylamino$_{(C≤18)}$, heteroarylamino$_{(C≤18)}$, heteroaralkylamino$_{(C≤18)}$, heterocycloalkylamino$_{(C≤18)}$, or a substituted version of any of these groups; and
n is 1, 2, 3, 4, 5, 6, 7, or 8;
provided that the reactant compound does not contain a nonoxidized sulfur atom or a thiocarbonyl.

In some embodiments, X$_2$ is alkyl$_{(C≤18)}$, cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, alkoxy$_{(C≤18)}$, cycloalkoxy$_{(C≤18)}$, aryloxy$_{(C≤18)}$, aralkyloxy$_{(C≤18)}$, heteroaryloxy$_{(C≤18)}$, heteroaralkyloxy$_{(C≤18)}$, heterocycloalkoxy$_{(C≤18)}$, alkylamino$_{(C≤18)}$, dialkylamino$_{(C≤18)}$, cycloalkylamino$_{(C≤18)}$, dicycloalkylamino$_{(C≤18)}$, arylamino$_{(C≤18)}$, aralkylamino$_{(C≤18)}$, heteroarylamino$_{(C≤18)}$, heteroaralkylamino$_{(C≤18)}$, heterocycloalkylamino$_{(C≤18)}$, or a substituted version of any of these groups. X$_2$ may be cycloalkyl$_{(C≤18)}$, aryl$_{(C≤18)}$, aralkyl$_{(C≤18)}$, cycloalkoxy$_{(C≤18)}$, aryloxy$_{(C≤18)}$, aralkyloxy$_{(C≤18)}$, cycloalkylamino$_{(C≤18)}$, dicycloalkylamino$_{(C≤18)}$, arylamino$_{(C≤18)}$, aralkylamino$_{(C≤18)}$, or a substituted version of any of these groups. In some embodiments, X$_2$ is cycloalkyl$_{(C≤18)}$, aryl$_{(C≤18)}$, or a substituted version of any of either group. In some embodiments, the reactive functional group or X$_1$ is a hydroxy group. The reaction conditions may be Mitsunobu conditions. In some embodiments, the Mitsunobu conditions comprise adding an azodicarboxylate$_{(C≤12)}$. The azodicarboxylate$_{(C≤12)}$ may be diethyl azodicarboxylate or diisopropyl azodicarboxylate. In some embodiments, the Mitsunobu condition further comprise adding a triarylphosphine$_{(C≤24)}$ or substituted triarylphosphine$_{(C≤24)}$ such as triphenylphosphine. In some embodiments, R$_2$ is a monovalent amino protecting group such as t-butyloxycarbonyl. R$_1$ may be an arylsulfonyl$_{(C≤12)}$ such as p-toluenesulfonyl, 2,4,6-trimethylphenylsulfonyl, or 2,4,6-triisopropylphenylsulfonyl.

In some embodiments, the rhodium catalyst is a dirhodium catalyst such as a tetravalent dirhodium catalyst. In some embodiments, the rhodium catalyst of the formula: Rh$_2$(L$_1$)$_4$ or Rh$_2$(L$_2$)$_2$, wherein:
L$_1$ is an acylate$_{(C≤12)}$ or a substituted acylate$_{(C≤12)}$; and
L$_2$ is a diacylate$_{(C≤18)}$ or a substituted diacylate$_{(C≤18)}$.
In some embodiments, L$_1$ is acylate$_{(C≤12)}$ such as acetate or octanoate or a substituted acylate$_{(C≤12)}$ such as trifluoroacetate. In other embodiments, L$_2$ is diacylate$_{(C≤18)}$ such as:

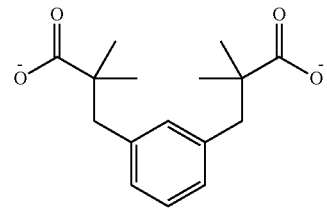

The rhodium catalyst may be Rh$_2$(OAc)$_4$, Rh$_2$(TFA)$_4$, Rh$_2$(C$_8$H$_{15}$O$_2$)$_4$, Rh$_2$(esp)$_2$, Rh$_2$(R)-(PTAD) [PTAD=tetrakis[(R)-(−)-(1-adamantyl)-(N-phthalimido)acetato]dirhodium (II), or Rh$_2$(S)-(PTAD). In some embodiments, the rhodium catalyst is Rh$_2$(esp)$_2$.

In some embodiments, the N-heterocycloalkyl group contains 4 to 8 ring atoms or 4 to 6 ring atoms. The N-heterocycloalkyl group may contain 5 ring atoms. In some embodiments, the methods further comprise reacting the substrate compound with the rhodium catalyst in a reaction mixture. The reaction mixture may comprise an organic solvent. In some embodiments, organic solvent contains one or more halogen atoms. The organic solvent may be an alcohol$_{(C1-8)}$ such as trifluoroethanol.

In some embodiments, the reaction mixture has a temperature from about 0° C. to about 100° C. The temperature from about 0° C. to about 75° C. or from about 0° C. to about 50° C. The temperature may be about 25° C. or about room temperature. The methods may comprise adding from about 0.05 mol % to about 10 mol % of the rhodium catalyst. In some embodiments, the methods comprise adding from about 0.1 mol % to about 5 mol % of the rhodium catalyst. The method may comprise adding from about 0.5 mol % to about 2.5 mol % of the rhodium catalyst. In some embodiments, the methods comprise adding about 2 mol % of the rhodium catalyst. In some embodiments, the acid is $R_4CO_2H$; wherein: $R_4$ is alkyl$_{(C≤8)}$, cycloalkyl$_{(C≤8)}$, or a substituted version of either group. $R_4$ may be alkyl$_{(C≤8)}$ or substituted alkyl$_{(C≤8)}$ such as trifluoromethyl. In some embodiments, the acid is trifluoroacetic acid.

In some embodiments, the aminating compound is reacted with the acid and the rhodium catalyst for a time period from about 1 hour to about 3 days. The time period may be from about 6 hours to about 2.5 days or from about 12 hours to about 36 hours.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

Figure 1:
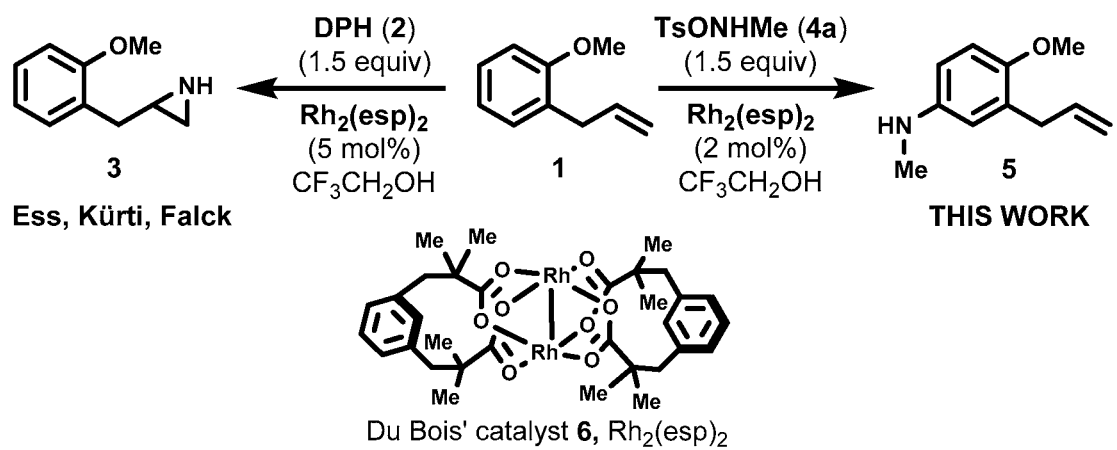
FIG. 1 shows a dramatic shift in chemoselectivity arises with different aminating agents. o-Allylanisole (1) undergoes chemoselective olefin aziridination in the presence of catalytic $Rh_2(esp)_2$ (6) and aminating agent o-(2,4-dinitrophenyl)hydroxylamine (DPH) (2) in 2,2,2-trifluoroethanol (TFE=$CF_3CH_2OH$) to give 3. Changing the aminating agent to TsONHMe (4a) furnishes the corresponding N-Me aniline (5).

In some aspects, the present disclosure provides synthetic methodologies which may be used to introduce an amino group on an aryl ring. In other aspects, the methods may be used to generate a nitrogen containing cyclic structure joined to an aryl ring. In yet another aspect, the nitrogen atom is inserted intramolecularly into sp2 C—H bonds to form alicyclic nitrogen heterocycles. In some embodiments, these reactions are carried out without the need to employ one or more directing groups or the use of harsh conditions. The methods described herein may be used in the synthesis of a variety of useful primary and secondary amines on aromatic rings which may be used as precursors in the preparation of other compounds or as the final step of a longer synthetic scheme. In another embodiments, the methods may result in the formation of an N-heterocycloalkane group resultant from the intramolecular cyclization of the aminating compound and a reactant compound for use in other synthetic pathways.

I. AROMATIC COMPOUNDS

The methods described herein may be used to introduce an amine group on an aromatic compound. As used herein, the term aromatic compound is a series of atoms which contains 4n+2, wherein n is an integer, pi electrons in a cyclic system with all atoms being either sp or sp$^2$ hybridized and has at least one hydrogen atom attached to one of the carbon atoms of the aromatic ring. In some embodiments, the aromatic compound consists of a ring with only carbon atoms. In other embodiments, one or more of the ring atoms is a heteroatom selected from a nitrogen or oxygen atom. Additionally, the aromatic compound may further comprise 1, 2, 3, 4, 5, 6, 7, 8, or 9 additional rings which may be either aromatic as described above or aliphatic (e.g., cycloalkyl such as cyclopentyl, cyclohexyl, or cycloheptyl). These additional rings may be attached to the aromatic compound in a pendant fashion or may be fused to the aromatic ring. The aliphatic rings may also contain one or more double or triple bonds. Within the context of the aromatic compound, the ring system is the series of rings (either pendant or fused) which contain the aromatic ring. The ring system may contain only one aromatic ring or contain as many as 5 aromatic rings. The ring system does not include any rings contained within additional functional groups which may be optionally joined to the aromatic compound such as those described below or a protecting group as descried herein. Additionally, in some embodiments, the aromatic compound may contain one or more attached alkyl, alkenyl, or alkynyl functional groups attached to the aromatic compound. Some non-limiting examples of alkyl, alkenyl, or alkynyl function groups which may be attached to the aromatic compound include methyl, ethyl, isopropyl, t-butyl, allyl, or ethynyl group.

Additionally, the aromatic compound may be unsubstituted and contain only hydrogen and carbon atoms. In other embodiments, the aromatic compound is substituted with one or more functional groups selected from amino, carboxy, halo, hydroxy, oxo, phosphate, hydroxysulfonyl, or acyl, alkoxy, acyloxy, amido, alkylamino, dialkylamino, alkylsulfonyl, arylsulfonyl, alkylsulfonylamino, arylsulfonylamino, or a substituted version of any of these groups. The aromatic compound may be substituted with 1, 2, 3, 4, 5, 6, 7, or 8 additional functional groups. In some embodiments, the aromatic compound is substituted with 1, 2, 3, or 4 functional groups. In another aspect, it is contemplated that one or more of these functional groups may contain a protecting group which prevents that group from interfering with the amination reaction. Such protecting groups are known to a person of ordinary skill in the art and are taught such as those by Greene and Wuts, "Greene's Protecting Groups in Organic Synthesis: Fifth Edition," John Wiley & Sons. Inc. (2014). These protecting groups may be removed using deprotecting agents. The appropriate deprotecting agents needed to remove a specific protecting group and known to those of skill in the art and are taught by Greene and Wuts (2014). In some embodiments, the substrate may not comprise a nonoxidized sulfur atom. In some embodiments, the aromatic ring is an electron rich aromatic ring.

The aromatic compounds which may be used in the methods described herein may contain less than 100 atoms. In some embodiments, the aromatic compound contains from 3, 4, 5, 6, 7, 8, 9, 10, 11, 12, 13, 14, 15, 16, 17, 18, 19, 20, 21, 22, 23, 24, 25, 26, 27, 28, 29, or 30 atoms, or any range derivable therein. In some embodiments, the aromatic compound has from about 5 atoms to about 24 atoms, from about 5 atoms to about 18 atoms, or from about 5 atoms to about 12 atoms. It is contemplated that the aromatic compound may further comprise one or more heteroatoms in the ring system. The ring system may contain 1, 2, 3, 4, 5, 6, 7, 8, 9, 10, or more heteroatoms selected from nitrogen, oxygen, phosphorus, or boron atoms. In some embodiments, the ring system contains from 1 to 4 heteroatoms, 1 to 3 heteroatoms, 1 heteroatom, or 2 heteroatoms. The heteroatoms may be in the same ring or multiple different rings within the ring system. Additionally, in some embodiments, the heteroatoms is a nitrogen atom or an oxygen atom.

In some embodiments, the aminating agent may be contained with a branch of the aromatic ring such that the reaction with the aromatic ring to form a second ring containing a nitrogen atom. The branched chain containing the aminating agent may be attached to a ring which is fused to the aromatic ring. In other embodiments, the aminating agent is attached to an alipathic chain which separates the aromatic ring and the aminating agent. The number of atoms between the aromatic ring and the aminating agent is from 0, 1, 2, 3, 4, or 5 atoms such that the resultant ring formed is a four membered ring, a five membered ring, a six membered ring, a seven membered ring, an eight membered ring, or a nine membered ring.

II. N-HETEROCYCLOALKANE COMPOUND

In other aspects, the present disclosure relates to methods of prepare an N-heterocycloalkane compound wherein the nitrogen atom arises from the reactive aminating agent. In some embodiments, the methods comprise reacting a reactant compound which contains at least one aliphatic linker and a second aliphatic or aromatic group. In some embodiments, the aliphatic linker contains no aromatic carbon atoms and reacts with itself to form the N-heterocycloalkane group. As described above for the aromatic compound, the N-heterocycloalkane group may be optionally substituted with groups selected from an amino, carboxy, halo, hydroxy, oxo, phosphate, hydroxysulfonyl, aminosulfonyl, or acyl, alkoxy, acyloxy, amido, alkylamino, dialkylamino, alkylsulfonyl, arylsulfonyl, alkylsulfonylamino, arylsulfonylamino, or a substituted version of any of these groups. In some embodiments, the N-heterocycloalkane group may be substituted from 0, 1, 2, 3, 4, 5, or 6 times. In some embodiments, the substrate may not comprise a nonoxidized sulfur atom. In some embodiments, the substrate comprises an electron deficient aromatic ring or an aliphatic group.

III. AMINATING AGENT

In some aspects, the present disclosure comprises using an aminating agent which transfers a nitrogen atom to the aromatic compound. The aminating agent is an aliphatic or aromatic sulfonylhydroxyamino such as those described by formula I below:

wherein $R_1$ is an aliphatic or aromatic sulfonyl group; $R_2$ is hydrogen or alkyl$_{(C\leq12)}$, alkenyl$_{(C\leq12)}$, alkynyl$_{(C\leq12)}$, aryl$_{(C\leq12)}$, aralkyl$_{(C\leq12)}$, or a substituted version of any of these groups, or a monovalent amino protecting group, or $R_2$ and $R_3$ are taken together and are a divalent amino protecting group; and $R_3$ is hydrogen or a monovalent amino protecting group. In other embodiments, $R_1$ may be a dinitrophenyl group such as 2,4-dinitrophenyl provided that the reaction mixture is sufficiently acidic. In some embodiments, $R_1$ is an aromatic sulfonyl group such as an arylsulfonyl$_{(C\leq12)}$ or a substituted arylsulfonyl$_{(C\leq12)}$. Some non-limiting examples of aminating agents include:

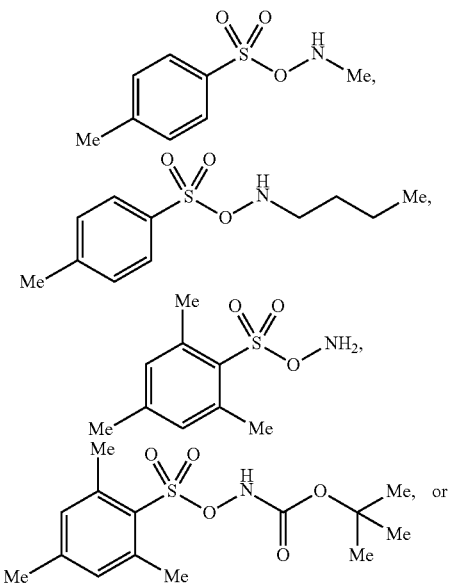

-continued

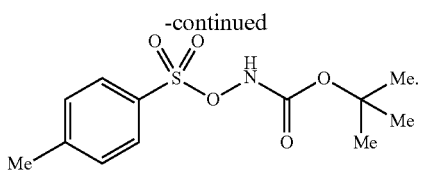

The aminating agent may also be introduced into the same molecule by converting a reactive functional group. A reactive functional group is a functional group which may be converted through one or two steps into a group which undergoes nucleophilic displacement or is a functional group which undergoes nucleophilic displacement. Some non-limiting examples of reactive functional groups including tosyl, mesyl, trifluoromethanesulfonyl, hydroxy, mercapto, or halo. Methods of converting a reactive functional group include those taught by *March's Advanced Organic Chemistry* (2013) and *Strategic Applications of Named Reactions in Organic Synthesis* (2005).

IV. RHODIUM CATALYST

In some aspects, the methods described herein uses a rhodium catalyst. The rhodium catalyst may contain one or more divalent rhodium atoms. In some embodiments, the rhodium catalyst contains two rhodium atoms. The catalyst may further comprise one or more carboxylate ligands such as acetate, trifluoroacetate, octanoate, or a single ligand may contain two or more carboxylate ligands such as:

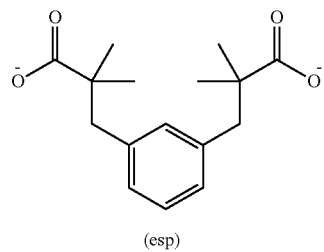

(esp)

Some non-limiting examples of the rhodium catalyst described herein include $Rh_2(OAc)_4$, $Rh_2(TFA)_4$, $Rh_2(C_8H_{15}O_2)_4$, or $Rh_2(esp)_2$. In another aspect, the rhodium catalyst may be $Rh_2(R)$-(PTAD) or $Rh_2(S)$-(PTAD), wherein PTAD is tetrakis[(R)-(−)-(1-adamantyl)-(N-phthalimido)acetato]dirhodium (II).

V. REACTION CONDITIONS

In another aspect, the present disclosure provides methods of carrying out a reaction which comprises creating a reaction mixture containing an organic solvent. The solvent may be an alcohol containing from 1 to 8 carbon atoms such as methanol, ethanol, butanol, or trifluoroethanol. In some embodiments, the solvent may comprise a second solvent such as a second alcohol or haloalkane. Some non-limiting examples of haloalkanes such as dichloromethane, chloroform, or dichloroethane. In some embodiments, one of the two solvents if a mixture of solvents is used is trifluoroethanol. In some embodiments, the reaction mixture may further comprise an anhydrous solvent. In other embodiments, the solvent or solvent mixture may further comprise less than 5% water.

Furthermore, the methods described herein may further comprise adjusting the temperature of the reaction mixture. The temperature of the reaction may be reduced below room temperature such as a temperature below 20° C. The temperature of the reaction may be from about −30° C. to about 30° C. In some embodiments, the temperature of the reaction mixture is about 0° C.

Additionally, the methods described herein may further comprises adding specific amounts of each of the components. In some embodiments, the methods comprise adding from about 0.5 equivalents to about 5 equivalents of the aminating compound relative to the aromatic compound. In particular, the methods may use greater than 1 equivalent of the aminating compound. The methods may comprises using from about 1 equivalent to about 2 equivalents of the aminating compound such as about 1.5 equivalents of the aminating compound. Additionally, the methods that are described herein may include using greater than 0.01 mol % of the rhodium catalyst. In some embodiments, the amount of the rhodium catalyst is from about 0.05 mol % to about 10 mol %, from about 0.1 mol % to about 5 mol %, or from about 0.5 mol % to about 2.5 mol %. The methods require using either 1 mol % or 2 mol % of the rhodium catalyst.

VI. PROCESS SCALE-UP

The synthetic methods described herein can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of the compounds described herein.

VII. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxysulfonyl" means —S(O)$_2$OH; "aminosulfonyl" means —S(O)$_2$NH$_2$; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example,

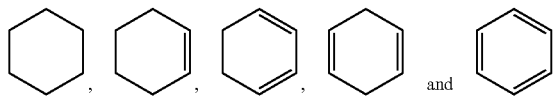 and .

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⫼" means a single bond where the group attached to the thick end of the wedge is "into the page". The symbol "⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

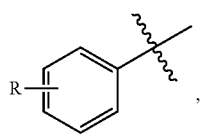

then R may replace any hydrogen atom attached to any of the ring atoms, including a depicted, implied, or expressly defined hydrogen, so long as a stable structure is formed.

When a group "R" is depicted as a "floating group" on a fused ring system, as for example in the formula:

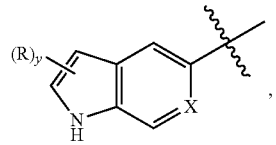

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in a moiety replacing a hydrogen atom is not counted. Thus methoxyhexyl, which has a total of seven carbon atoms, is an example of a substituted alkyl$_{(C1-6)}$.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic a system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$) CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C (CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkanetriyl" group refers to a trivalent saturated aliphatic group, with one or two saturated carbon atom(s) as the point(s) of attachment, a linear or branched acyclic structure, no carbon-carbon double or triple bonds, and no atoms other than carbon and hydrogen. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

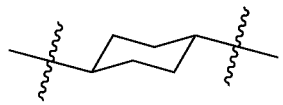 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —OCH, —CH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH₃, and —CH₂C≡CCH₃ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aryl" when used without the "substituted" modifier refers to a monovalent unsaturated aromatic group with an aromatic carbon atom as the point of attachment, said carbon atom forming part of a one or more aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

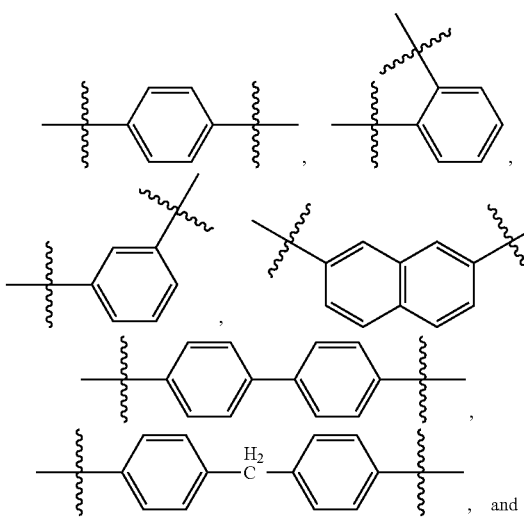

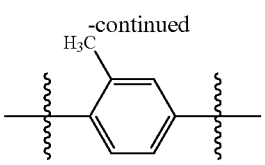

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. Similarly, the term "aralkanediyl" refers to the group: -alkanediyl-arenediyl-, -arenediyl-alkanediyl-, -alkanediyl-arenediyl-alkanediyl-, or -alkanetriyl-aryl- as those terms are defined above. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen or oxygen, and wherein the heteroaryl group consists of no atoms other than carbon, hydrogen, aromatic nitrogen, and aromatic oxygen. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O) CH₃, —NHC(O)CH₃, —S(O)₂OH, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen or oxygen, and wherein the heterocycloalkyl group consists of no atoms other than carbon, hydrogen, nitrogen, and oxygen. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, tetrahydrofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. The term "aldehyde" corresponds to an alkyl group, as defined above, attached to a —CHO group. The term "acylate" refers to the group RC(O)O$^-$, in which R is a hydrogen, alkyl, cycloalkyl, or aryl as those terms are defined above. Similarly, the term "diacylate" refers to the group $^-$OC(O)RC(O)O$^-$, wherein R is alkanediyl, cycloalkanediyl, arenediyl, or aralkanediyl as those terms are defined above. The term "azodicarboxylate" references to a compound of the formula: R'OC(O)N=NC(O)OR", wherein R' and R" are an alkyl group as that term is defined above. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The terms "alkylsulfonyl" when used without the "substituted" modifier refers to the groups —S(O)$_2$R, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —OCH, —CH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The terms "phosphine" and "phosphane" are used synonymously herein. When used without the "substituted" modifier these terms refer to a compound of the formula PR$_3$, wherein each R is independently hydrogen, alkyl, cycloalkyl, alkenyl, aryl, or aralkyl, as those terms are defined above. Non-limiting examples include PMe$_3$, PPh$_3$, and PCy$_3$ (tricyclohexylphosphine). The terms "triarylphosphine" and "triarylphosphane" are also synonymous. Such groups are a subset of phosphine, wherein each R is an aryl group. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. In all other contexts, the term "about" represents±5%.

An "amino protecting group" is well understood in the art. An amino protecting group is a group which prevents the reactivity of the amine group during a reaction which modifies some other portion of the molecule and can be easily removed to generate the desired amine. Amino protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amino protecting group" can be a divalent protecting group such that both hydrogen atoms on a primary amine are replaced with a single protecting group. In such a situation the amino protecting group can be phthalimide (phth) or a substituted derivative thereof wherein the term "substituted" is as defined above. In some embodiments, the halogenated phthalimide derivative may be tetrachlorophthalimide (TCphth). When used herein, a protected amino group is a group of the formula PG$_{A1}$PG$_{A2}$N— wherein PG$_{A1}$ and PG$_{A2}$ are an monovalent amino protecting group as described above or one of these two groups may be a hydrogen provided the other is a monovalent amino protecting group or the two groups are taken together to form a divalent amino protecting group.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

An "isomer" of a first compound is a separate compound in which each molecule contains the same constituent atoms as the first compound, but where the configuration of those atoms in three dimensions differs.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present disclosure.

VIII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Amination of Arene

Following a systematic investigation, arene amination was demonstrated as described as FIG. 1. Treatment of 1-allyl-2-methoxybenzene (o-allylanisole, 1) with O-(2,4-dinitrophenyl)-hydroxylamine (2) (Yang, 2014) and catalytic Rh$_2$(esp)$_2$ (Du Bois' catalyst, 6: 5 mol %) in 2,2,2-trifluoroethanol (TFE) at 0° C. afforded the corresponding aziridine (3) as the primary product whereas use of N-methyl-O-tosylhydroxylamine (4a) (John et al., 2007) as the aminating agent and catalytic Rh$_2$(esp)$_2$ (Du Bois' catalyst, 6: 2 mol %) under similar conditions furnished primarily the arene amination adduct 3-allyl-4-methoxy-N-methylaniline (5). Consequently, a study of the direct arene amination lead to a versatile, regioselective, operationally simple and mild dirhodium-catalyzed direct arene amination, without external oxidant, suitable for both intermolecular and intramolecular applications.

Mesitylene (7a) was selected as a model arene to optimize reaction parameters. Use of 2 mol % Rh$_2$(esp)$_2$ and 1.5 equivalents of aminating agent 4a in TFE as solvent smoothly generated N-methylaniline 8a (75%) in just 30 min at 0° C. (FIG. 2, Entry 1); comparable yields were obtained with 1 mol % and 0.5 mol % catalyst, except the latter required 1 h for complete consumption of starting material. Combinations of TFE with CH$_2$Cl$_2$ or MeOH in ratios up to 1:1 were suitable, but aminations run in EtOH or MeOH as the only solvent delivered poor yields (~10-20%) and those run in only DMF, CH$_3$CN, THF, toluene, and dioxane failed. Amongst alternative Rh-catalysts, Rh$_2$(OAc)$_2$ and Rh$_2$(C$_8$H$_{15}$O$_2$)$_4$ were the next best with moderate yields (~40-45%) while the performance by Rh$_2$(TFA)$_4$ was poor. Results from other catalysts are summarized in Example 4. Generally, reactions were quenched as soon as the substrate was completely consumed to minimize by-product formation. Air and water (5% v/v) were well tolerated making the methodology operationally convenient for standard lab conditions.

The successful transfer of a nBuNH— unit to 7a from TsONHnBu (4b) affording 8b in a 52% yield (FIG. 2, Entry 2) suggests more complex amino moieties should also be suitable. For the introduction of —NH$_2$ into 7a, 2,4,6-Me$_3$C$_6$H$_3$S(O)$_2$ONH$_2$ (Mendiola et al., 2009) (4c, 2 equiv) was utilized as aminating agent because of its superior handling characteristics compared with TsONH$_2$ (Carpino, 1960). While all of 4c was consumed, a considerable amount of unreacted 7a was recovered and a modest yield (49%) of 8c was realized (Entry 3). On the other hand, the simple and expedient generation of the aminating agent in situ from 2,4,6-Me$_3$C$_6$H$_3$S(O)$_2$ONH$^t$Boc (4d, 1.5 equiv) and CF$_3$CO$_2$H (2 equiv) proved quite effective and boosted the yield of 8c to 70% (Entry 4), although the reaction was much slower than in the case of aminating agent 4c (Entry 3) and appeared to be dependent upon the rate of $^t$Boc cleavage.

Figure 2:
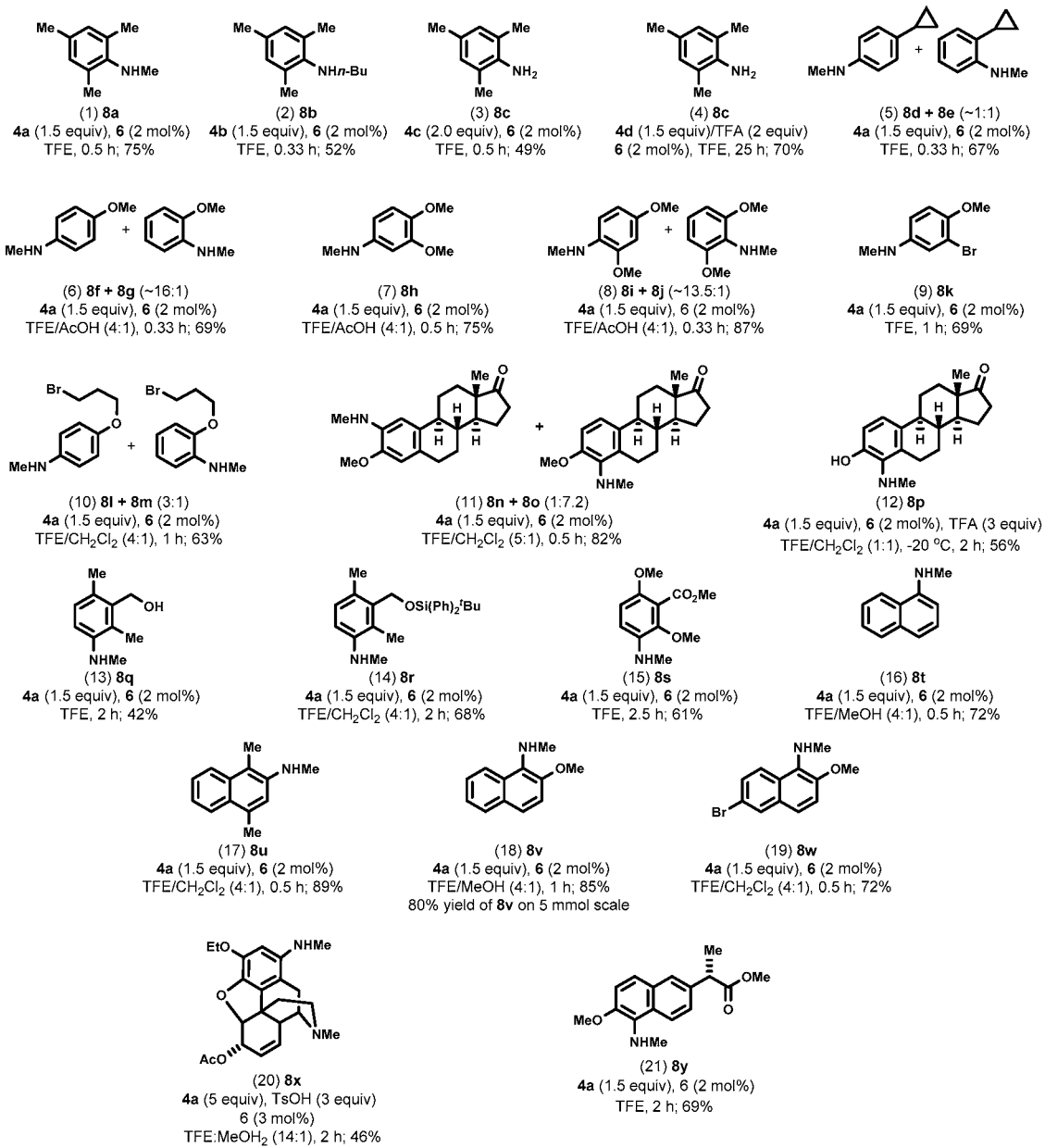
FIG. 2 shows the direct intermolecular amination of arenes. Reactions were conducted on a 0.25 mmole scale at 0.1 M using 2,2,2-trifluoroethanol (TFE=$CF_3CH_2OH$) as solvent or using mixtures of TFE and other solvents as indicated.

The results from other representative arenes are also summarized in FIG. 2. Despite having only a single aliphatic substituent, cyclopropylbenzene (7d) was well behaved, affording a 1:1 p-lo-mixture (8d & 5e) in 20 min at 0° C. with no evidence of addition to the strained three-membered ring (Entry 5). The directing effect in favor of the para-isomer was more pronounced with anisole (7f) and led to a 16:1 distribution of 8f and 8g (Entry 6). This effect completely dominated in veratrole (7h) that gave 8h as the sole regioisomer (Entry 7) and was equally evident in the conversion of 1,3-dimethoxybenzene (7i) into 8i, although a minor amount (6%) of the ortho-isomer 8j was found despite the increased steric congestion at this site (Entry 8). Addition of acetic acid to the reaction solvent for the latter three examples (e.g., Entries 6-8) improved the yields and suppressed the formation of mauve-colored by-products that we assume arose from further oxidation of the aminated adducts.

Aryl bromide 7k (Entry 9) and terminal alkyl bromide 7l (Entry 10) endured to deliver 8k and a mixture of 8l/8m (3:1), respectively, leaving the halogens available for further manipulation, if desired. The smooth generation of 8n and 8o (1:7.2, Entry 11) in very good yield from O-methyestrone (7n) and only one regioisomer 8p (Entry 12) from the parent phenol, estrone (7p), illustrates the suitability of this methodology for late stage functionalization of complex molecules and validates the applicability of the amination methodology for substrates containing potentially sensitive benzylic, tertiary, and α-keto hydrogens. However, the presence of some functional groups partially retard amination, e.g. exposure of benzyl alcohol 7q to the standard amination conditions generated a modest amount of 8q (42%) after 2 h (Entry 13); on the other hand, protection as silyl ether 7r resulted in a much improved yield of 8r (68%) (Entry 14). Fortunately, a synthetically useful yield of amine could be obtained even in the presence of electron withdrawing substituents, e.g. 7s→8s (Entry 15). The amination process was also extended to fused aromatics: naphthalene (7t) and 1,4-dimethylnapthalene (7u) gave rise to N-methyl-1-naphthylamine (St, Entry 16) and N-methyl-1,4-dimethyl-2-naphthylamine (8u, Entry 17), respectively, while 2-methoxynaphthalene (7v) readily underwent amination to give 8v in 85% yield on a 0.5 mmol scale and in 80% yield on a 5 mmol scale (Entry 18). The smooth amination of 2-methoxy-6-bromonaphthalene (7w) into N-methyl-2-methoxy-6-bromo-1-naphthylamine (8w, Entry 19) succinctly illustrates the chemo- and regio-selectivities of this methodology. Additional examples of late stage arene aminations are found in 3-O-ethyl-6-acetylmorphine (8, Entry 20) and methyl naproxen (8y, Entry 21).

Example 2—Formation of Aza-Annulation

Figure 3:
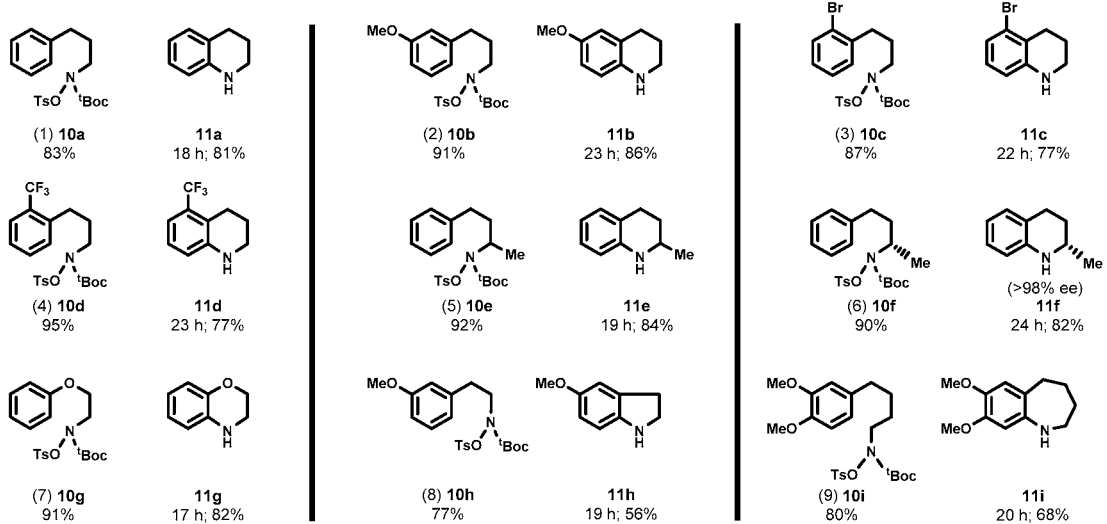
FIG. 3 shows the direct intramolecular cyclization (aza-annulation) of arenes. Cyclizations were conducted at 0.1 M using 2,2,2-trifluoroethanol (TFE=$CF_3CH_2OH$) as the solvent on a 0.5 mmol scale unless otherwise indicated.

The intramolecular version of the amination proved quite facile and represents a mild and efficient aza-annulation (FIG. 3). The enabling amination functionality was introduced in uniformly good yields via the Mitsunobu reaction under standard conditions from the corresponding alcohols, 9a-i. Acidic cleavage of the $^t$Boc on the Mitsunobu adducts 10a-i and subsequent in situ amination proceeded at 0° C. Fused aza-annulated bicycles were created in good yields irrespective of additional ring substituents, 10a→11a (Entry 1), electron donating, 10b→11b (Entry 2), or electron withdrawing functionality, 10c→11c (Entry 3) and 10d→11d (Entry 4). Secondary alcohols likewise participated readily in the Mitsunobu and aza-annulation reactions, 9e→10e→11e (Entry 5). Importantly, this 2-step sequence, when conducted using the chiral alcohol 9f, showed no loss of stereochemical integrity (Entry 6). Incorporation of a heteroatom into the ring closure, e.g., 9g→10g→11g (Entry 7), did not perturb the chemistry and provided easy access to the dihydrobenzoxazine class of heterocycles. The yield declined somewhat for making the 5-membered dihydroindole 11h from alcohol 9h (Entry 8), but improved for the 7-membered tetrahydrobenzazepine 11i from 9i (Entry 9).

Example 3—Proposed Reaction Mechanism

Figure 4:
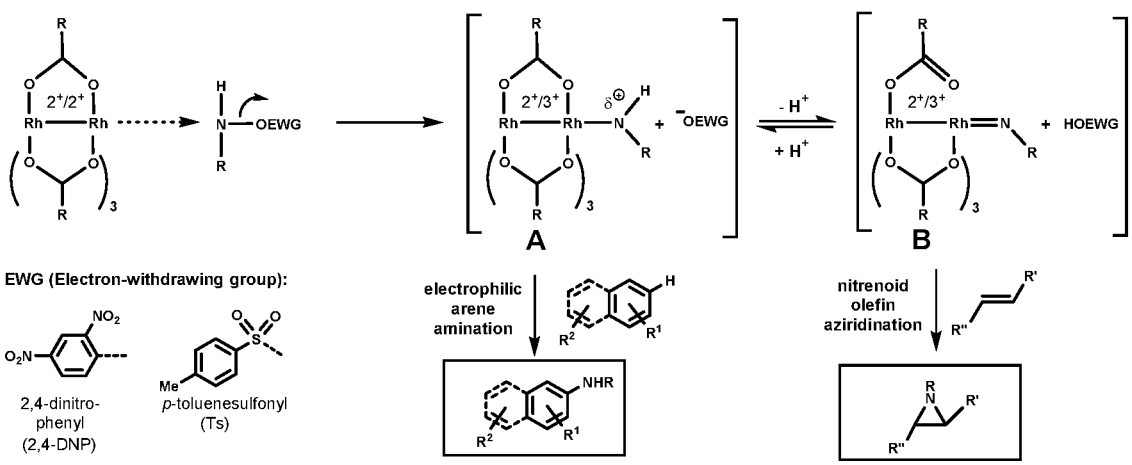
FIG. 4 shows the proposed intermediates leading to amination or aza-amination versus aziridination and insertion.
Figure 5:
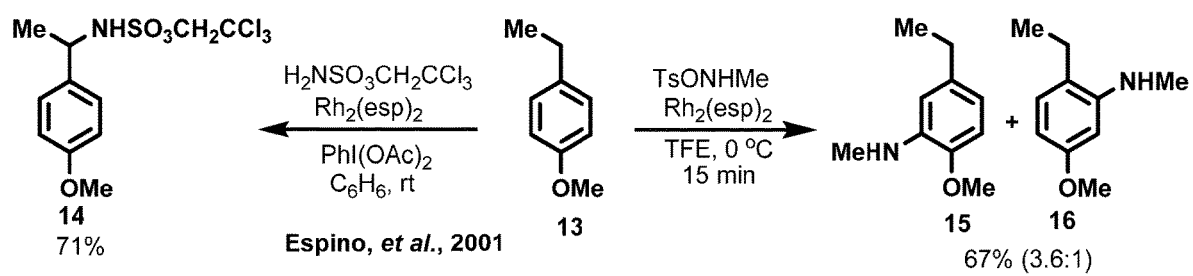
FIG. 5 shows the direct arene amination presented herein vs. benzylic C—H insertion described by Du Bois (Espino et al., 2004).

In order to obtain some insight into the mechanism of the amination, a 1:1 mixture of naphthalene (7t) and 7t-d$_8$ was treated with a limited amount of amination reagent (4a, 0.5 equiv) under otherwise standard reaction conditions. Samples were taken and quenched at 10, 20, 30 and 40 min. Analysis via SIM-LC/MS revealed the product ratios remained constant at ~1:1, a ratio inconsistent with an organometallic C—H activation pathway which are typically ~3:1 or higher (Jones, 2003 and Simmons and Hartwig, 2012). Based on density functional theory calculations, the aziridination of alkenes has been suggested to involve the dirhodium-nitrenoid intermediate B shown in FIG. 4 that arises from overall NH transfer from the DPH-aminating reagent to the dirhodium catalyst (Jat et al., 2014). In contrast, reaction of O-tosylhydroxylamine reagents with the dirhodium catalyst favor intermediate A since TsO$^-$ is weakly basic and the equilibrium with intermediates B lies far to the left. Without wishing to be bound by any theory it is believed that the chemoselectivity may be explained by the more electrophilic nature of intermediate A versus nitrenoid B. This preliminary hypothesis is consistent with the observation that moderate to strong bases such as K$_2$CO$_3$, Et$_3$N, and pyridine completely inhibit amination, but not aziridination. Moreover, addition of TsOH (1.5 equiv) to the reaction of 1 with 2,4-DNPONHMe (12) produced only the arene amination adduct 5 and no aziridine. As an additional control, it was shown that the presence of 2,4-DNP—OH (1.5 equiv) did not alter the reaction manifold in favor of aziridination when 4a was utilized as the aminating reagent and only 5 was observed.

The present methodology was also compared with the intermolecular Rh-catalyzed amination procedure of Du Bois to gain a perspective of their respective complementary chemoselectivities (FIG. 4) (Espino et al., 2004). Both have similar efficiency using p-ethylanisole (13), but the Du Bois procedure leads to benzylic C—H insertion only whereas our methodology gives arene amination exclusively providing 15 and 16 in a combined 67% yield.

Example 4—Insertion Characterization

Proton and carbon nuclear magnetic resonance spectra ($^1$H and $^{13}$C NMR) were obtained on a Varian 400 spectrometer at 400 MHz and 101 MHz, respectively, or on a Varian 500 at 500 MHz and 126 MHz, respectively, in CDCl$_3$, unless otherwise stated. The $^1$H NMR chemical shifts were measured relative to CDCl$_3$ as the internal reference (CDCl$_3$: δ=7.26 ppm), unless otherwise stated. The $^{13}$C NMR chemical shifts were given using CDCl$_3$ as the internal standard (CDCl$_3$: δ=77.00 ppm). $^1$H NMR data are reported as: chemical shift (ppm), multiplicity (s=singlet, br s=broad singlet, d=doublet, t=triplet, q=quartet, app q=apparent quartet, qn=quintet, app qn=apparent quintet, app sextet=apparent sextet, m=multiplet), and coupling constant (Hz). High resolution mass spectra (HRMS) were obtained using a Shimadzu IT-TOF mass spectrometer at UT Arlington. Melting points were measured using an OptiMelt from Stanford Research Systems and are uncorrected. Analytical thin layer chromatography (TLC) used EMD Chemicals TLC silica gel 60 F$_{254}$ plates (0.040-0.063 mm) with visualization by UV light and/or KMNO$_4$ or phosphomolybdic acid (PMA) solution followed by heating. Chromatographic purifications utilized preparative TLC or flash chromatography using pre-packed SiO$_2$ columns on a medium pressure automated chromatograph. Unless otherwise noted, yields refer to isolated, purified material with spectral data consistent with assigned structures or, if known, were in agreement with literature values. All reactions were conducted under an argon atmosphere in oven-dried glassware with magnetic stirring, unless otherwise stated. Reagents were purchased at the highest commercial quality and used without further purification. Reaction solvents, except anhydrous CH$_3$CN and 2,2,2-trifluoroethanol (Aldrich Chem. Co.) which were used directly, were purified via passage through activated, neutral alumina columns and stored under argon. Amination reagents were obtained from Corvinus Chemicals and Rh catalysts from Sigma-Aldrich and Strem Chemicals.

FIG. 1: Left Panel

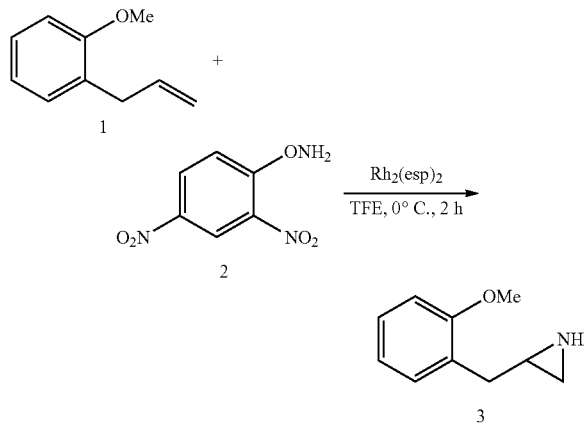

FIG. 1: Right Panel

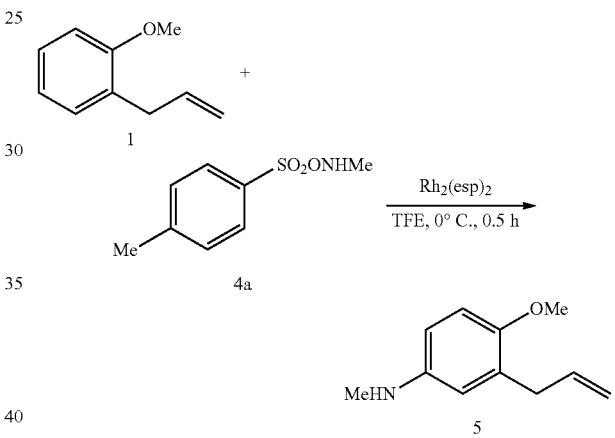

To a stirring, 0° C. solution of 2-allylanisole (1: 30 mg, 0.2 mmol) in 2,2,2-trifluoroethanol (TFE: 2 mL) was added Du Bois' catalyst, Rh$_2$(esp)$_2$ (7.6 mg, 0.01 mmol) followed by O-(2,4-dinitrophenyl)hydroxylamine (2: 60 mg, 0.3 mmol). After 2 h, the reaction mixture was diluted with CH$_2$Cl$_2$ (20 mL) and washed with saturated aqueous Na$_2$CO$_3$ solution (5 mL). The aqueous layer was separated and extracted with CH$_2$Cl$_2$ (2×5 mL). The extracts were combined with the original organic layer, then washed with brine (5 mL), dried over anhydrous Na$_2$SO$_4$, and concentrated in vacuo. The crude residue was purified by preparative TLC using 5% MeOH/CH$_2$Cl$_2$ as eluent to furnish 2-(2-methoxybenzyl)aziridine (3: 10 mg, 32%) as an oil. TLC: R$_f$≈0.3 (5% MeOH/CH$_2$Cl$_2$); $^1$H NMR (400 MHz, CDC$_3$) δ 7.27-7.17 (m, 2H), 6.96-6.83 (m, 2H), 3.83 (s, 3H), 2.79 (dd, J=14.3, 6.0 Hz, 1H), 2.71 (dd, J=14.3, 5.9 Hz, 1H), 2.29-2.19 (m, 1H), 1.75 (d, J=5.7 Hz, 1H), 1.45 (d, J=3.5 Hz, 1H), 0.77 (br s, 1H); $^3$C NMR (101 MHz, CDCl$_3$) δ 157.44, 130.26, 127.63, 127.38, 120.44, 110.17, 55.22, 34.60, 30.11, 24.97. HRMS (ESI$^+$) Calcd. for [C$_{10}$H$_{13}$NO+H]$^+$ 164.1075, Found 164.1072.

Following the general intermolecular amination procedure (vide infra), 2-allylanisole (1: 44 mg, 0.3 mmol), Du Bois' catalyst (4.5 mg, 6.0 μmol), and TsONHMe (91 mg, 0.45 mmol) were stirred at 0° C. in TFE (3 mL) for 0.5 h. Chromatographic purification of the crude product afforded 3-allyl-4-methoxy-N-methylaniline (5: 32 mg, 60%) as an oil. TLC: R$_f$≈0.6 (30% EtOAc/hexanes); $^1$H NMR (400 MHz, CDCl$_3$) δ 6.77 (dd, J=8.1, 1.2 Hz, 1H), 6.50-6.45 (m, 2H), 6.05-5.93 (m, 1H), 5.12-4.98 (m, 2H), 3.76 (s, 3H), 3.35 (d, J=7.2 Hz, 2H), 2.80 (s, 3H); $^{13}$C NMR (101 MHz, CDCl$_3$) δ 149.95, 143.51, 137.16, 129.63, 115.29, 115.25, 112.23, 110.54, 56.33, 34.38, 31.65. HRMS (ESI$^+$) Calcd. for [C$_{11}$H$_{15}$NO+H]$^+$ 178.1232, Found 178.1231.

General Procedure for Intermolecular C—H Amination

Du Bois' catalyst [Rh$_2$(esp)$_2$: 2 mol %] and aminating agent (1.5 equiv) were added to a stirring 0.1 M solution of arene (1.0 equiv) at 0° C. under an argon atmosphere in 2,2,2-trifluoroethanol (TFE), unless otherwise stated. The progress of the reaction was monitored by TLC (20 min to 2 h). After complete consumption of the starting material, the reaction mixture was diluted with EtOAc or CH$_2$Cl$_2$ and basified with saturated aqueous Na$_2$CO$_3$ solution (pH~9). The aqueous layer was extracted thrice with EtOAc. The combined organic extracts were washed with brine, dried over anhydrous Na$_2$SO$_4$, and concentrated in vacuo. The crude residue was purified on pre-packed SiO₂ columns using a medium pressure, automated chromatograph.

Intermolecular Amination Experimental

FIG. 2: Entry 1

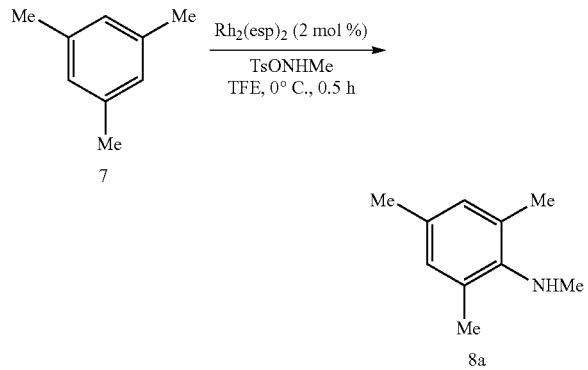

Following the general intermolecular amination procedure, mesitylene (7a: 60 mg, 0.5 mmol), Du Bois' catalyst (7.6 mg, 0.01 mmol), and TsONHMe (0.151 g, 0.75 mmol) were stirred at 0° C. in TFE (5 mL) for 0.5 h. Chromatographic purification of the crude product afforded N,2,4,6-tetramethylaniline (8a: 56 mg, 75%) as an oil. TLC: $R_f$≈0.6 (20% EtOAc/hexanes); $^1$H NMR (400 MHz, CDCl₃) δ 6.85 (s, 2H), 2.93 (br s, 1H), 2.76 (s, 3H), 2.29 (s, 6H), 2.25 (s, 3H); $^{13}$C NMR (101 MHz, CDCl₃) δ 144.89, 131.30, 129.52, 129.44, 35.60, 20.55, 18.17. HRMS (ESI⁺) Calcd. for $[C_{10}H_{15}N+H]^+$ 150.1283, Found 150.1279.

FIG. 2: Entry 2

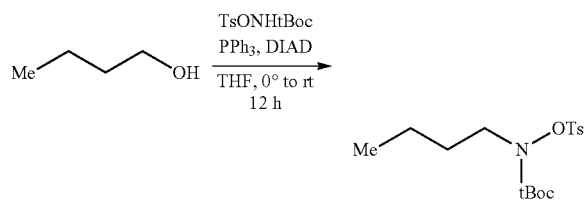

Following the general Mitsunobu procedure (vide infra), n-butanol (0.37 g, 5.0 mmol), PPh₃ (1.44 g, 5.5 mmol), DIAD (1.11 g, 5.5 mmol), and TsONH$^t$Boc (1.44 g, 5.0 mmol) were stirred at rt in dry THF (10 mL) for 12 h. Chromatographic purification of the crude product afforded tert-butyl butyl(tosyloxy)carbamate as an oil (1.63 g, 95%). TLC: $R_f$≈0.8 (25% EtOAc/hexane); $^1$H NMR (600 MHz, CDCl₃) δ 7.84 (d, J=8.1 Hz, 2H), 7.33 (d, J=8.0 Hz, 2H), 3.59 (br s, 2H), 2.44 (s, 3H), 1.58 (br s, 2H), 1.31-1.23 (m, 2H), 1.21 (s, 9H), 0.89 (t, J=7.4 Hz, 3H); $^{13}$C NMR (151 MHz, CDCl₃) δ 155.50, 145.62, 131.31, 129.67, 129.49, 83.03, 52.67, 27.84, 27.59, 21.67, 19.74, 13.69. HRMS (ESI⁺) Calcd. for $[C_{15}H_{25}NO_5S+H]^+$ 344.1532, Found 344.1525.

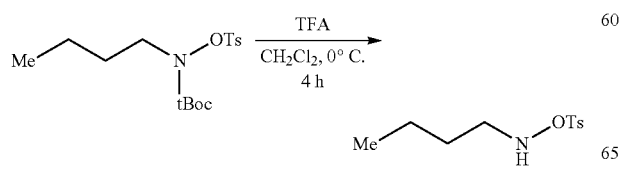

Trifluoroacetic acid (3 mL, 39 mmol) was added to a stirred 0° C. solution of tert-butyl butyl(tosyloxy)carbamate (0.620 g, 1.8 mmol) in dry CH₂Cl₂ (1 mL). After 4 h, all volatiles were evaporated, the residue was treated with saturated aq. Na₂CO₃ (10 mL), and extracted with EtOAc (10 mL×4). The combined organic extracts were dried over anhydrous Na₂SO₄ and concentrated in vacuo to afford N-butyl-O-tosylhydroxylamine as an oil (436 mg, 99%) which was used directly for the amination step without further purification. TLC: $R_f$≈0.6 (25% EtOAc/hexane.

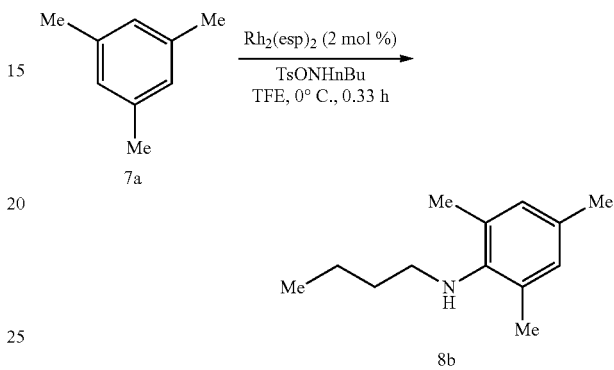

Following the general intermolecular amination procedure, mesitylene (7a: 60 mg, 0.5 mmol), Du Bois' catalyst (7.6 mg, 0.01 mmol), and TsONHnBu (0.182 g, 0.75 mmol) were stirred at 0° C. in TFE (4 mL) for 0.33 h. Chromatographic purification of the crude product afforded N-butyl-2,4,6-trimethylaniline (8b: 50 mg, 52%) as an oil. TLC: $R_f$≈0.5 (8% EtOAc/hexane); $^1$H NMR (600 MHz, CDCl₃) δ 6.82 (s, 2H), 2.93 (t, J=7.2 Hz, 2H), 2.25 (s, 6H), 2.23 (s, 3H), 1.57 (app qn, J=7.5 Hz, 2H), 1.42 (app sextet, J=7.5 Hz, 2H), 0.94 (t, J=7.3 Hz, 3H); $^{13}$C NMR (151 MHz, CDCl₃) δ 144.20, 131.34, 129.80, 129.73, 49.04, 33.63, 20.89, 20.73, 18.70, 14.35. HRMS (ESI⁺) Calcd. for $[C_{13}H_{21}N+H]^+$ 192.1752. Found 192.1761.

FIG. 2: Entry 3 (General Intermolecular Procedure)

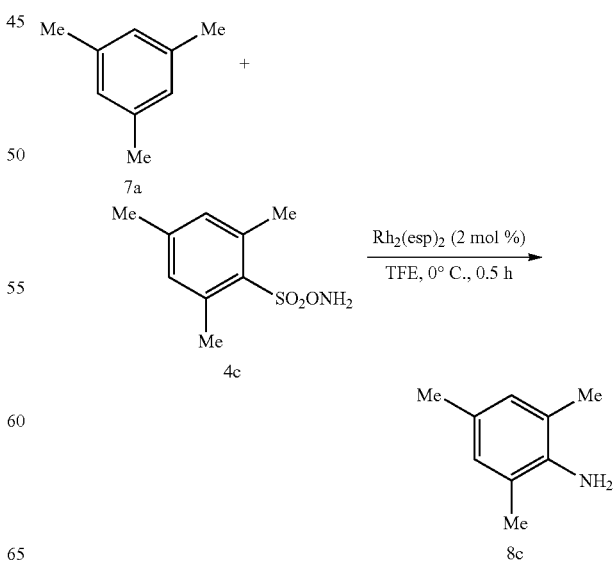

Following the general intermolecular amination procedure, mesitylene (7a: 60 mg, 0.5 mmol), Du Bois' catalyst (7.6 mg, 0.01 mmol), and O-(mesitylsulfonyl)hydroxylamine (4c: 0.215 g, 1.0 mmol) were stirred at 0° C. in TFE (5 mL) for 0.5 h. Chromatographic purification of the crude product afforded 2,4,6-trimethylaniline (8c: 66 mg, 49%) as an oil whose spectral characteristics were concordant with literature values (43). $^1$H NMR (400 MHz, CDCl$_3$) δ 6.79 (s, 2H), 3.56 (br s, 2H), 2.23 (s, 3H), 2.18 (s, 6H); $^{13}$C NMR (101 MHz, CDCl$_3$) δ 139.96, 128.84, 127.26, 121.96, 20.37, 17.61.

FIG. 2: Entry 4 (In Situ Generation Procedure)

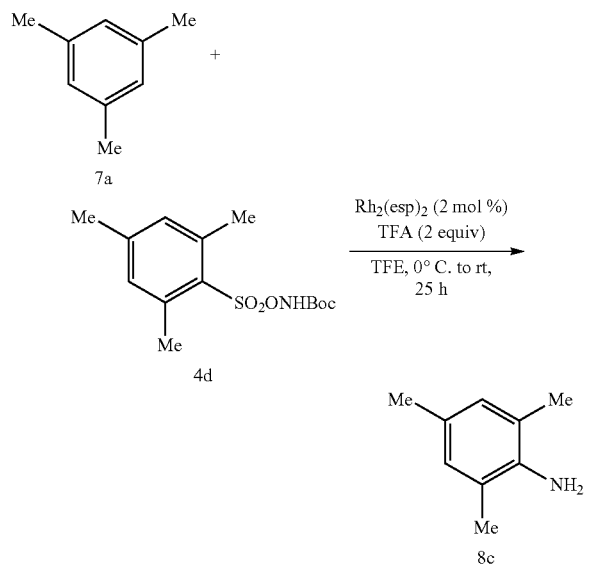

To a 0° C. solution of mesitylene (7a: 42 μL, 0.3 mmol) and tert-butyl (mesitylsulfonyl)oxycarbamate (4d: 142 mg, 0.45 mmol, 1.5 equiv) in TFE (3 mL) was added CF$_3$CO$_2$H (TFA: 46 μL, 0.6 mmol, 2 equiv) and Rh$_2$(esp)$_2$ (4.55 mg, 6 μmol). The reaction was allowed to gradually warm to rt overnight. After 25 h, the reaction mixture (a suspension) was poured carefully into sat. aq. NaHCO$_3$ (15 mL) and extracted with EtOAc (3×7 mL). The combined organic extracts were dried over Na$_2$SO$_4$, filtered, and concentrated in vacuo. The residue was purified by PTLC (15% EtOAc/hexanes) to give 2,4,6-trimethylaniline (8c: 28.5 mg, 70%) as an oil whose spectral characteristics were concordant with literature values (see above).

FIG. 2: Entry 5

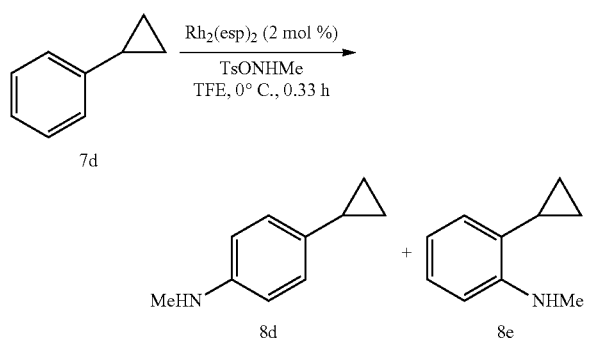

Following the general intermolecular amination procedure, cyclopropyl benzene (7d: 0.118 g, 1.0 mmol), Du Bois' catalyst (15.2 mg, 0.02 mmol), and TsONHMe (0.302 g, 1.5 mmol) were stirred at 0° C. in TFE (10 mL) for 0.33 h. Chromatographic purification of the crude product afforded 8d (50 mg) and 8e (48 mg) (98 mg total, 67% combined yield) as oils.

4-Cyclopropyl-N-methylaniline (8d): TLC: R$_f$≈0.6 (20% EtOAc/hexanes); $^1$H NMR (400 MHz, CDCl$_3$) δ 6.98 (d, J=8.5 Hz, 2H), 6.58 (d, J=8.5 Hz, 2H), 3.49 (br s, 1H), 2.83 (s, 3H), 1.89-1.80 (m, 1H), 1.00-0.80 (m, 2H), 0.70-0.49 (m, 2H); $^{13}$C NMR (101 MHz, CDCl$_3$) δ 147.31, 132.47, 126.82, 112.63, 31.10, 14.58, 8.14. HRMS (ESI$^+$) Calcd. for [C$_{10}$H$_{13}$N+H]$^+$ 148.1126, Found 148.1121.

2-Cyclopropyl-N-methylaniline (Se): TLC: R$_f$≈0.8 (20% EtOAc/hexanes); $^1$H NMR (400 MHz, CDCl$_3$) δ 7.18 (t, J=7.4 Hz, 1H), 7.07 (d, J=7.5 Hz, 1H), 6.68 (t, J=7.4 Hz, 1H), 6.62 (d, J=8.0 Hz, 1H), 4.39 (br s, 1H), 2.94 (s, 3H), 1.65-1.56 (m, 1H), 1.07-0.74 (m, 2H), 0.71-0.46 (m, 2H); $^{13}$C NMR (101 MHz, CDCl$_3$) δ 148.67, 128.10, 127.44, 126.37, 116.36, 108.83, 30.73, 11.23, 4.99. HRMS (ESI$^+$) Calcd. for [C$_{10}$H$_{13}$N+H]$^+$148.1126, Found 148.1124.

FIG. 2: Entry 6

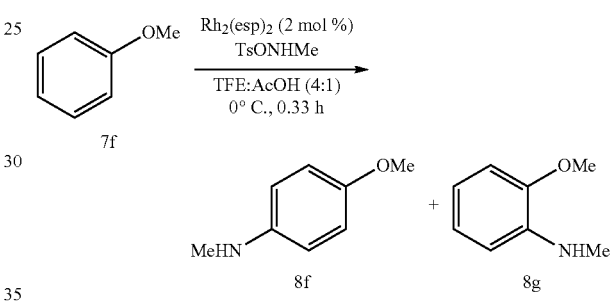

Following the general intermolecular amination procedure, anisole (7f: 54 mg, 0.5 mmol), Du Bois' catalyst (7.6 mg, 0.01 mmol), and TsONHMe (0.151 g, 0.75 mmol) were stirred at 0° C. in a mixture of TFE/AcOH (4:1, 5 mL) for 0.33 h. The reaction was basified with aqueous 1.0 M NaOH. Chromatographic purification of the crude product afforded 8f (44 mg) and 8g (3 mg) as oils (69% combined yield) whose spectral data were in agreement with literature values (44).

4-Methoxy-N-methylaniline (8f)

TLC: R$_f$≈0.5 (30% EtOAc/hexanes); $^1$H NMR (400 MHz, CDC$_3$) δ 6.81 (d, J=8.9 Hz, 2H), 6.60 (d, J=8.8 Hz, 2H), 3.76 (s, 3H), 3.29 (br s, 1H), 2.81 (s, 3H).

2-Methoxy-N-methylaniline (8g)

TLC: R$_f$≈0.7 (30% EtOAc/hexanes); $^1$H NMR (400 MHz, CDCl$_3$) δ 6.90 (td, J=7.5, 1.2 Hz, 1H), 6.77 (dd, J=7.9, 1.4 Hz, 1H), 6.67 (td, J=7.6, 1.4 Hz, 1H), 6.60 (dd, J=7.8, 1.5 Hz, 1H), 4.23 (br s, 1H), 3.84 (s, 3H), 2.86 (s, 3H).

FIG. 2: Entry 7

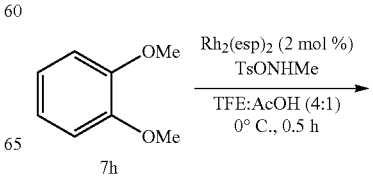

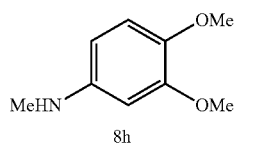

Following the general intermolecular amination procedure, veratrole (7h: 0.138 g, 1.0 mmol), Du Bois' catalyst (15.2 mg, 0.02 mmol), and TsONHMe (0.301 g, 1.5 mmol) were stirred in a mixture of TFE/AcOH (4:1, 10 mL) at 0° C. for 0.5 h. The reaction was basified with 1.0 M aq. NaOH. Chromatographic purification of the crude product afforded 3,4-dimethoxy-N-methylaniline (8h: 126 mg, 75%) as an oil whose spectral data were in agreement with literature values (45). TLC: $R_f$≈0.3 (40% EtOAc/hexanes); $^1$H NMR (400 MHz, CDCl$_3$) δ 6.76 (d, J=8.6 Hz, 1H), 6.25 (d, J=2.6 Hz, 1H), 6.15 (dd, J=8.5, 2.6 Hz, 1H), 3.83 (s, 3H), 3.80 (s, 3H), 3.49 (br s, 1H), 2.81 (s, 3H); $^{13}$C NMR (101 MHz, CDCl$_3$) δ 149.97, 144.25, 141.53, 113.24, 103.10, 98.61, 56.73, 55.69, 31.58.

FIG. 2: Entry 8

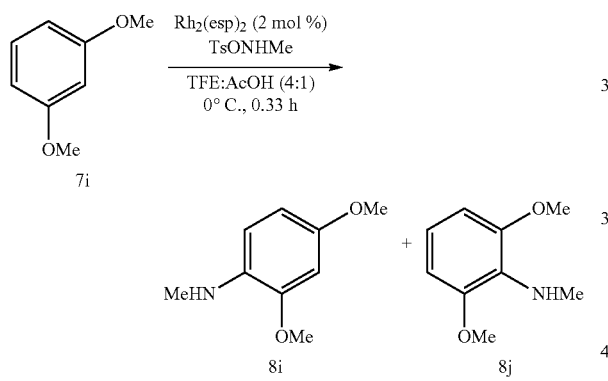

Following the general intermolecular amination procedure, 1,3-dimethoxybenzene (7i: 69 mg, 0.5 mmol), Du Bois' catalyst (7.6 mg, 0.01 mmol), TsONHMe (0.151 g, 0.75 mmol) were stirred in a mixture of TFE/AcOH (4:1, 5 mL) at 0° C. for 0.33 h. The reaction was basified with 1.0 M aq. NaOH. Chromatographic purification of the crude product afforded 8i (68 mg) and 8j (5 mg) as oils (87% combined yield).

2,4-Dimethoxy-N-methylaniline (46) (8i)

TLC: $R_f$≈0.4 (40% EtOAc/hexanes); $^1$H NMR (400 MHz, CDCl$_3$) δ 6.52 (d, J=8.2 Hz, 1H), 6.48-6.42 (m, 2H), 3.82 (s, 3H), 3.76 (s, 3H), 2.83 (s, 3H); $^{13}$C NMR (101 MHz, CDCl$_3$) δ 151.82, 147.97, 133.80, 109.54, 103.69, 99.07, 55.82, 55.42, 31.10.

2,6-Dimethoxy-N-methylaniline (8j)

TLC: $R_f$≈0.2 (40% EtOAc/hexanes); $^1$H NMR (400 MHz, CDCl$_3$) δ 6.81 (t, J=8.3 Hz, 1H), 6.55 (d, J=8.3 Hz, 2H), 3.84 (s, 6H), 2.89 (s, 3H); $^{13}$C NMR (101 MHz, CDCl$_3$) δ 151.01, 128.93, 119.87, 104.77, 55.93, 34.62. HRMS (ESI$^+$) Calcd. for [C$_9$H$_{13}$NO$_2$+H]$^+$ 168.1024, Found 168.1018.

FIG. 2: Entry 9

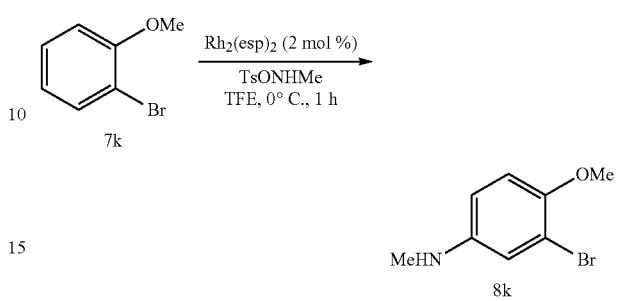

Following the general intermolecular amination procedure, 2-bromoanisole (7k: 56 mg, 0.3 mmol), Du Bois' catalyst (4.5 mg, 6.0 μmol), and TsONHMe (90 mg, 0.45 mmol) were stirred in TFE (3 mL) at 0° C. for 1 h. Chromatographic purification of the crude product afforded 3-bromo-4-methoxy-N-methylaniline (8k) as an oil (45 mg, 69%). TLC: $R_f$≈0.4 (30% EtOAc/hexanes); $^1$H NMR (400 MHz, CDCl$_3$) δ 6.84 (d, J=2.8 Hz, 1H), 6.80 (d, J=8.8 Hz, 1H), 6.53 (dd, J=8.8, 2.8 Hz, 1H), 3.81 (s, 3H), 3.52 (br s, 1H), 2.79 (s, 3H); $^{13}$C NMR (101 MHz, CDCl$_3$) δ 148.19, 144.59, 117.34, 114.00, 112.69, 112.39, 57.14, 31.37. HRMS (ESI$^+$) Calcd. for [C$_8$H$_{10}$BrNO+H]$^+$ 216.0024, Found 216.0019.

FIG. 2: Entry 10

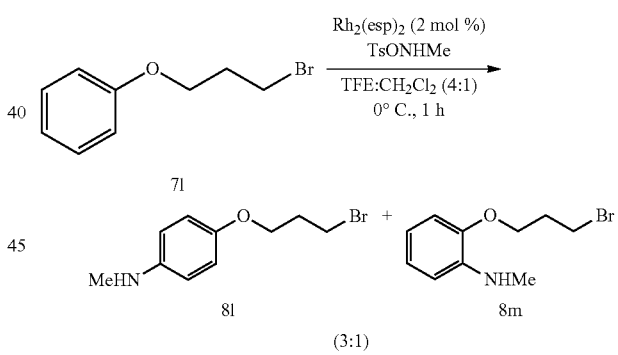

Following the general intermolecular amination procedure, 3-phenoxy-1-bromopropane (7l: 43 mg, 0.2 mmol), Du Bois' catalyst (3.0 mg, 4.0 μmol), TsONHMe (60 mg, 0.3 mmol) were stirred at 0° C. in a mixture of TFE/CH$_2$Cl$_2$ (4:1, 2 mL) for 1 h. Chromatographic purification of the crude product afforded 8l (23 mg) and 8m (8 mg) as oils (63% combined yield).

4-(3-Bromopropoxy)-N-methylaniline (8l)

TLC: $R_f$≈0.4 (30% EtOAc/hexanes); $^1$H NMR (400 MHz, CDCl$_3$) δ 6.81 (d, J=8.9 Hz, 2H), 6.63 (d, J=8.9 Hz, 2H), 4.03 (t, J=5.8 Hz, 2H), 3.60 (t, J=6.5 Hz, 2H), 2.83 (s, 3H), 2.35-2.22 (m, 2H); $^{13}$C NMR (101 MHz, CDCl$_3$) δ 151.35, 143.45, 115.86, 114.04, 66.17, 32.54, 31.89, 30.25. HRMS (ESI⁺) Calcd. for [C₁₀H₁₄BrNO+H]⁺ 244.0337, Found 244.0332.

2-(3-bromopropoxy)-N-methylaniline (8m)

TLC: R_f≈0.6 (30% EtOAc/hexanes); ¹H NMR (400 MHz, CDCl₃) δ 6.91 (td, J=7.6, 1.2 Hz, 1H), 6.78 (dd, J=8.0, 1.4 Hz, 1H), 6.67 (dd, J=7.8, 1.4 Hz, 1H), 6.62 (td, J=7.6, 1.2 Hz, 1H), 4.21 (br s, 1H), 4.14 (t, J=5.8 Hz, 2H), 3.60 (t, J=6.5 Hz, 2H), 2.87 (s, 3H), 2.35 (app qn, J=6.2 Hz, 2H); ¹³C NMR (101 MHz, CDCl₃) δ 145.67, 139.38, 121.67, 116.29, 110.42, 109.54, 65.67, 32.42, 30.35, 29.98. HRMS (ESI⁺) Calcd. for [C₁₀H₁₄BrNO+H]⁺ 244.0337, Found 244.0339.

FIG. 2: Entry 11

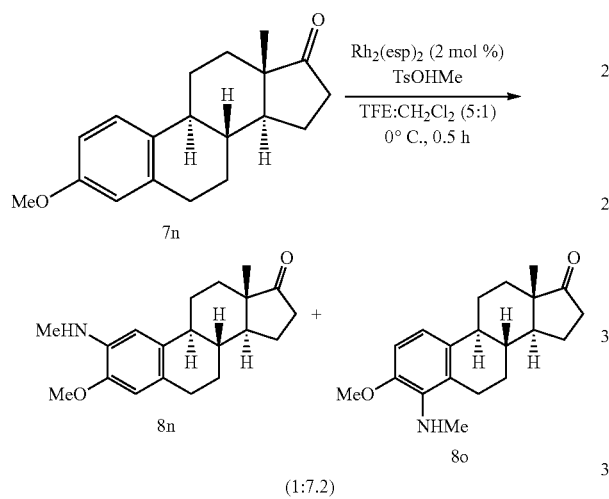

Following the general intermolecular amination procedure, O-methylestrone (7n: 85 mg, 0.3 mmol), Du Bois' catalyst (4.5 mg, 6 μmol), and TsONHMe (90 mg, 0.45 mmol) were stirred at 0° C. in a mixture of TFE/CH₂Cl₂ (5:1, 3.0 mL) for 0.5 h. Chromatographic purification of the crude product afforded 8n (9 mg) and 8o (68 mg) as solids (82% combined yield).

(8R,9S,13S,14S)-3-Methoxy-13-methyl-2-(methylamino)-7,8,9,11,12,13,15,16-octahydro-6H-cyclopenta[a]phenanthren-17(14H)-one (8n)

mp 139.0° C. (dec.); TLC: R_f≈0.4 (30% EtOAc/hexanes); ¹H NMR (400 MHz, CDC₃) δ 6.54 (s, 1H), 6.49 (s, 1H), 4.15 (br s, 1H), 3.81 (s, 3H), 2.96-2.72 (m, 2H), 2.85 (s, 3H), 2.50 (dd, J=18.8, 8.6 Hz, 1H), 2.46-2.38 (m, 1H), 2.35-2.25 (m, 1H), 2.24-1.87 (m, 4H), 1.72-1.34 (m, 6H), 0.91 (s, 3H); ¹³C NMR (101 MHz, CDCl₃) δ 221.21, 145.41, 137.37, 131.74, 123.99, 109.96, 106.73, 55.46, 50.44, 48.08, 44.39, 38.58, 35.92, 31.70, 30.74, 29.14, 26.86, 26.17, 21.59, 13.89. HRMS (ESI⁺) Calcd. for [C₂₀H₂₇NO₂+H]⁺ 314.2120, Found 314.2128.

(8R,9S,13S,14S)-3-Methoxy-13-methyl-4-(methylamino)-7,8,9,11,12,13,15,16-octahydro-6H-cyclopenta[a]phenanthren-17(14H)-one (8o)

mp 147.4° C. (dec.); TLC: R_f≈0.3 (30% EtOAc/hexanes); ¹H NMR (400 MHz, CDCl₃) δ 6.91 (d, J=8.7 Hz 1H), 6.73 (d, J=8.5 Hz, 1H), 3.82 (s, 3H), 3.50 (br s, 1H), 2.98-2.86 (m, 1H), 2.80 (s, 3H), 2.78-2.64 (m, 1H), 2.50 (dd, J=18.6, 8.7 Hz, 1H), 2.45-2.34 (m, 1H), 2.34-2.23 (m, 1H), 2.21-2.01 (m, 3H), 1.99-1.89 (m, 1H), 1.71-1.30 (m, 6H), 0.92 (s, 3H); ¹³C NMR (101 MHz, CDCl₃) δ 221.00, 149.40, 137.67, 133.03, 128.89, 118.56, 108.41, 55.75, 50.49, 47.99, 44.60, 37.91, 35.92, 35.27, 31.68, 26.45, 26.19, 25.70, 21.59, 13.87. HRMS (ESI⁺) Calcd. for [C₂₀H₂₇NO₂+H]⁺ 314.2120, Found 314.2140.

FIG. 2: Entry 12

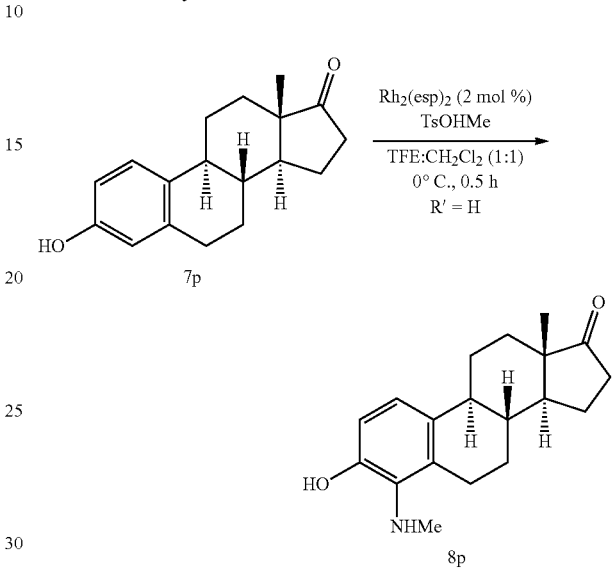

Following the general intermolecular amination procedure, estrone (7p: 135 mg, 0.5 mmol), Du Bois catalyst (7.6 mg, 0.01 mmol), TsONHMe (0.151 g, 0.75 mmol), and TFA (115 μL, 1.5 mmol) were stirred at −20 to 0° C. in a mixture of TFE/CH₂Cl₂ (1:1, 4 mL) for 2 h. Chromatographic purification of the crude product afforded (8R,9S,13S,14S)-3-hydroxy-13-methyl-4-(methylamino)-7,8,9,11,12,13,15,16-octahydro-6H-cyclopenta[a]phenanthren-17(14H)-one (8p) as a powder (89 mg, 56%), mp 174-176° C. TLC: R_f≈0.4 (50% EtOAc/Hexane); ¹H NMR (600 MHz, CDC₃) δ 7.02 (d, J=8.6 Hz, 1H), 6.81 (d, J=8.4 Hz, 1H), 5.15 (br s, 1H), 2.94 (dd, J=16.7, 5.9 Hz, 1H), 2.85-2.75 (m, 1H), 2.72 (s, 3H), 2.51 (dd, J=19.1, 8.8 Hz, 1H), 2.41-2.36 (m, 1H), 2.28-2.22 (m, 1H), 2.19-2.02 (m, 3H), 1.98-1.92 (m, 1H), 1.71-1.37 (m, 6H), 0.91 (s, 3H); ¹³C NMR (151 MHz, CDCl₃) δ 221.19, 150.15, 133.23, 132.15, 131.93, 123.10, 112.30, 50.71, 48.30, 44.57, 38.14, 36.22, 35.84, 31.92, 26.60, 26.42, 24.90, 21.93, 14.18. HRMS (ESI⁺) Calcd. for [C₁₉H₂₅NO₂+H]⁺ 300.1964, Found 300.1980.

FIG. 2: Entry 13

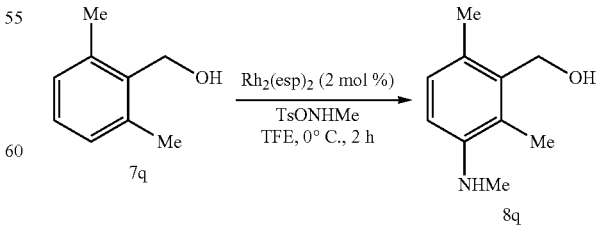

Following the general intermolecular amination procedure, 2,6-dimethylbenzyl alcohol (7q: 54 mg, 0.4 mmol), Du Bois' catalyst (6.1 mg, 8.0 μmol), and TsONHMe (0.121 g, 0.6 mmol) were stirred in TFE (4 mL) at 0° C. for 2 h. Chromatographic purification of the crude product afforded (2,6-dimethyl-3-(methylamino)phenyl)methanol (8q: 28 mg, 42%) as a solid, mp 78.6° C. TLC: $R_f$≈0.4 (40% EtOAc/hexanes); $^1$H NMR (400 MHz, CDCl$_3$) δ 7.00 (d, J=8.2 Hz, 1H), 6.56 (d, J=8.2 Hz, 1H), 4.74 (s, 2H), 2.88 (s, 3H), 2.35 (s, 3H), 2.20 (s, 3H); $^{13}$C NMR (101 MHz, CDCl$_3$) δ 145.88, 136.50, 128.53, 125.51, 121.93, 109.72, 59.77, 31.30, 19.13, 12.57. HRMS (ESI$^+$) Calcd. for [C$_{10}$H$_{15}$NO+H]$^+$ 166.1232, Found 166.1228.

FIG. 2: Entry 14

(m, 6H), 6.95 (d, J=8.1 Hz, 1H), 6.56 (d, J=8.1 Hz, 1H), 4.74 (s, 2H), 3.53 (br s, 1H), 2.90 (s, 3H), 2.13 (s, 3H), 2.10 (s, 3H), 1.06 (s, 9H); $^{13}$C NMR (101 MHz, CDCl$_3$) δ 145.67, 136.57, 135.80, 133.85, 129.58, 128.09, 127.57, 125.82, 122.37, 109.30, 60.94, 31.38, 26.89, 19.37, 19.25, 12.91. HRMS (ESI$^+$) Calcd. for [C$_{26}$H$_{33}$NOSi+H]$^+$ 404.2410, Found 404.2408.

FIG. 2: Entry 15

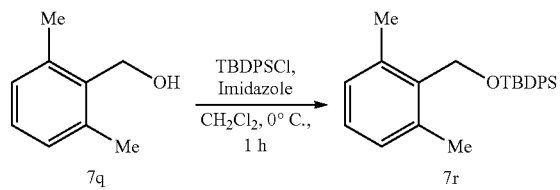

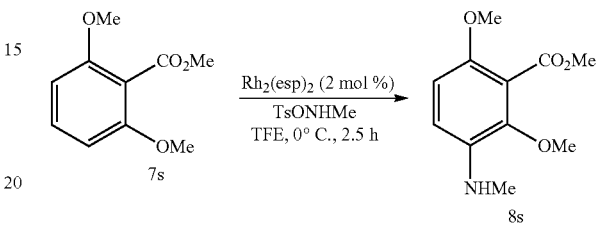

To a stirring, 0° C. solution of 2,6-dimethylbenzyl alcohol (7q: 0.272 g, 2.0 mmol) in dry CH$_2$Cl$_2$ (10 mL) was sequentially added imidazole (0.272 g, 4.0 mmol) and TBDPS chloride (0.62 mL, 2.4 mmol). After 1 h, the reaction mixture was diluted with CH$_2$Cl$_2$ (10 mL) and water (5 mL). The layers were separated and the organic layer was washed with brine (5 mL), dried over anhydrous Na$_2$SO$_4$, and concentrated in vacuo. The crude product was purified on a pre-packed SiO$_2$ column using a medium pressure, automated chromatograph to furnish tert-butyl-(2,6-dimethylbenzyloxy)diphenylsilane (7r: 0.695 g, 93%) as a solid, mp 41.5-41.8° C. TLC: $R_f$≈0.8 (10% EtOAc/hexanes); $^1$H NMR (400 MHz, CDCl$_3$) δ 7.74-7.62 (m, 4H), 7.48-7.33 (m, 6H), 7.12-7.03 (m, 1H), 6.98 (d, J=7.5 Hz, 2H), 4.71 (s, 2H), 2.24 (s, 6H), 1.04 (s, 9H); $^{13}$C NMR (101 MHz, CDCl$_3$) δ 137.46, 136.64, 135.75, 133.71, 129.61, 128.04, 127.58, 127.45, 60.56, 26.85, 19.65, 19.34. HRMS (ESI$^+$) Calcd. for [C$_{25}$H$_{30}$OSi+Na]$^+$ 397.1964, Found 397.1952.

Following the general intermolecular amination procedure, methyl 2,6-dimethoxybenzoate (7s: 29 mg, 0.15 mmol), Du Bois' catalyst (2.3 mg, 3.0 μmol), and TsONHMe (45 mg, 0.225 mmol) were stirred at 0° C. in TFE (2 mL) for 2.5 h. Chromatographic purification of the crude product afforded methyl 2,6-dimethoxy-3-(methylamino)benzoate (8s: 20 mg, 61%) as a solid, mp 83.6° C. TLC: $R_f$≈0.5 (30% EtOAc/hexanes); $^1$H NMR (400 MHz, CDCl$_3$) δ 6.65-6.58 (m, 2H), 3.92 (s, 3H), 3.77 (s, 3H), 3.75 (s, 3H), 2.81 (s, 3H); $^{13}$C NMR (101 MHz, CDCl$_3$) δ 167.01, 148.08, 144.54, 137.11, 118.19, 111.84, 107.79, 60.92, 56.61, 52.43, 30.97. HRMS (ESI$^+$) Calcd. for [C$_{11}$H$_{15}$NO$_4$+H]$^+$ 226.1079, Found 226.1074.

FIG. 2: Entry 16

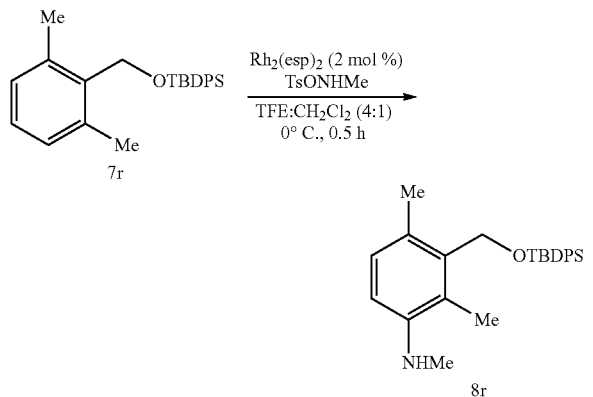

Following the general intermolecular amination procedure, tert-butyl((2,6-dimethylbenzyl)oxy)-diphenylsilane (7r 37 mg, 0.1 mmol), Du Bois' catalyst (1.5 mg, 2.0 μmol), and TsONHMe (30 mg, 0.15 mmol) were stirred at 0° C. in a mixture of TFE/CH$_2$Cl$_2$ (4:1, 1 mL) for 0.5 h. Chromatographic purification of the crude product afforded 3-((tert-butyldiphenylsilyloxy)methyl)-N,2,4-trimethylaniline (8r 27 mg, 68%) as an oil. TLC: $R_f$≈0.6 (10% EtOAc/hexanes); $^1$H NMR (400 MHz, CDCl$_3$) δ 7.75-7.68 (m, 4H), 7.48-7.31

Following the general intermolecular amination procedure, naphthalene (7t: 0.128 g, 1.0 mmol), Du Bois' catalyst (15.2 mg, 0.02 mmol), and TsONHMe (0.302 g, 1.5 mmol) were stirred at 0° C. in a mixture of TFE/MeOH (4:1, 10 mL) for 0.5 h. Chromatographic purification of the crude product afforded N-methylnaphthalen-1-amine (8t: 0.112 g, 72%) as a colorless oil whose spectral data were in agreement with literature values in Kung and Falvey, 2005. TLC: $R_f$≈0.8 (20% EtOAc/hexanes); $^1$H NMR (400 MHz, CDCl$_3$) δ 7.88-7.77 (m, 2H), 7.52-7.43 (m, 2H), 7.41 (d, J=8.1 Hz, 1H), 7.29 (d, J=8.2 Hz, 1H), 6.64 (d, J=7.1 Hz, 1H), 4.47

(br s, 1H), 3.03 (s, 3H); $^{13}$C NMR (101 MHz, CDCl$_3$) δ 144.48, 134.23, 128.67, 126.70, 125.74, 124.72, 123.46, 119.83, 117.36, 103.86, 31.07.

FIG. 2: Entry 17

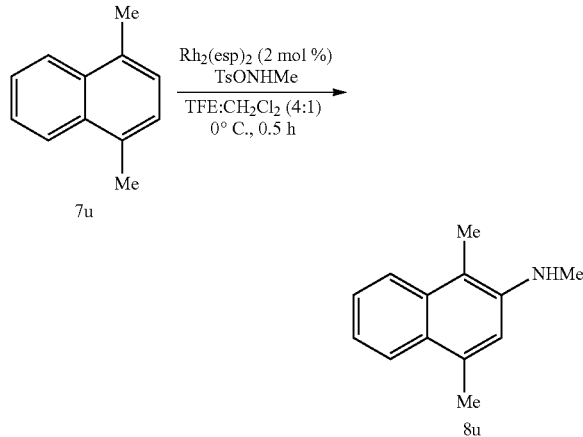

Following the general intermolecular amination procedure, 1,4-dimethylnaphthalene (7u: 78 mg, 0.5 mmol), Du Bois' catalyst (7.6 mg, 0.01 mmol), and TsONHMe (0.151 g, 0.75 mmol) were stirred at 0° C. in a mixture of TFE/ CH$_2$Cl$_2$ (4:1, 5 mL) for 0.5 h. Chromatographic purification of the crude product afforded N,1,4-trimethylnaphthalen-2-amine (8u: 83 mg, 89%) as an oil. TLC: R$_f$≈0.6 (25% EtOAc/hexane); $^1$H NMR (600 MHz, CDCl$_3$) δ 7.96 (d, J=9.7 Hz, 2H), 7.51 (t, J=7.7 Hz, 1H), 7.33 (t, J=7.5 Hz, 1H), 7.04 (s, 1H), 3.82 (br s, 1H), 3.07 (s, 3H), 2.76 (s, 3H), 2.43 (s, 3H); $^{13}$C NMR (151 MHz, CDCl$_3$) δ 144.15, 133.80, 133.48, 126.92, 126.05, 124.93, 123.08, 121.48, 114.64, 110.64, 31.77, 20.15, 11.43. HRMS (ESI$^+$) Calcd. for [C$_{13}$H$_{15}$N+H]$^+$ 186.1283, Found 186.1280.

FIG. 2: Entry 18

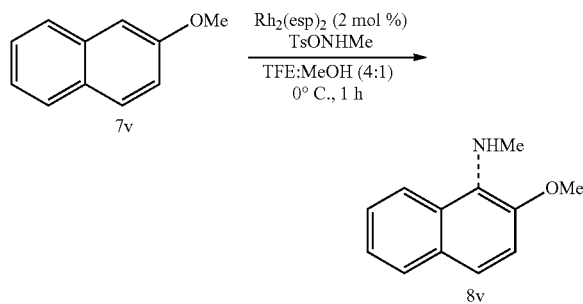

Following the general intermolecular amination procedure, 2-methoxynaphthalene (7v: 79 mg, 0.5 mmol), Du Bois' catalyst (7.6 mg, 0.01 mmol), and TsONHMe (0.151 g, 0.75 mmol) were stirred at 0° C. in a mixture of TFE/ MeOH (4:1, 5 mL) for 1 h. Chromatographic purification of the crude product afforded 2-methoxy-N-methylnaphthalen-1-amine (8v: 79 mg, 85%) as a solid, mp 106.6° C. (dec). Repetition on a 5.0 mmol (0.791 g) scale afforded 8v in 80% isolated yield. TLC: R$_f$≈0.6 (30% EtOAc/hexanes); $^1$H NMR (400 MHz, CDCl$_3$) δ 8.12 (d, J=8.7 Hz, 1H), 7.80 (d, J=8.1 Hz, 1H), 7.52 (d, J=8.7 Hz, 1H), 7.50-7.45 (m, 1H), 7.40-7.33 (m, 1H), 7.27 (d, J=8.8 Hz, 1H), 3.96 (s, 3H), 3.01 (s, 3H); $^{13}$C NMR (101 MHz, CDCl$_3$) δ 147.49, 133.91, 129.96, 128.33, 128.21, 125.30, 123.58, 122.85, 122.55, 113.53, 56.87, 37.17. HRMS (ESI$^+$) Calcd. for [C$_{12}$H$_{13}$NO+ H]$^+$ 188.1075, Found 188.1064.

FIG. 2: Entry 19

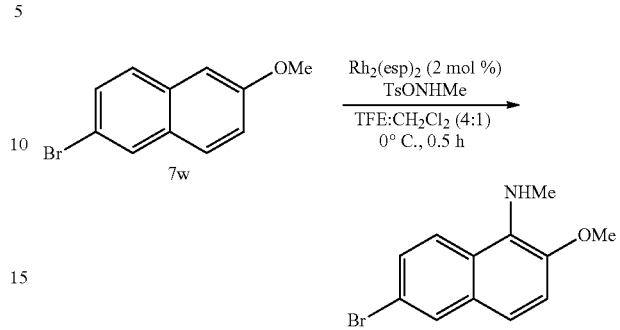

Following the general intermolecular amination procedure, 2-bromo-6-methoxynaphthalene (7w: 0.122 g, 0.5 mmol), Du Bois' catalyst (7.6 mg, 0.01 mmol), and TsONHMe (0.151 g, 0.75 mmol) were stirred at 0° C. in a mixture of TFE/CH$_2$Cl$_2$ (4:1, 5 mL) for 0.5 h. Chromatographic purification of the crude product afforded 6-bromo-2-methoxy-N-methylnaphthalen-1-amine (8w: 95 mg, 72%) as an oil. TLC: R$_f$≈0.7 (25% EtOAc/hexane); $^1$H NMR (600 MHz, CDCl$_3$) δ 7.96 (d, J=9.1 Hz, 1H), 7.91 (d, J=2.0 Hz, 1H), 7.49 (dd, J=9.1, 2.0 Hz, 1H), 7.38 (d, J=8.8 Hz, 1H), 7.25 (d, J=8.9 Hz, 1H), 3.94 (s, 3H), 2.95 (s, 3H); $^{13}$C NMR (151 MHz, CDCl$_3$) δ 147.99, 134.72, 131.34, 130.44, 128.71, 126.92, 125.22, 121.75, 117.71, 114.64, 57.10, 37.56. HRMS (ESI$^+$) Calcd. for [C$_{12}$H$_{12}$BrNO+H]$^+$ 266.0181.

Found 266.0207.

FIG. 2: Entry 20

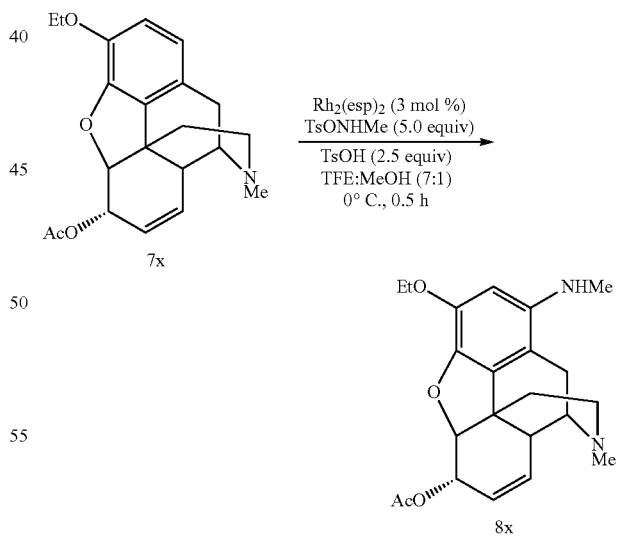

To an oven-dried vial with a magnetic stir bar was added the morphine alkaloid (7x: 35.5 mg, 0.1 mmol) and TsONHMe (0.101 g, 0.5 mmol, 5 equiv), followed by TFE (0.7 mL). The mixture was stirred until complete dissolution of solids, then cooled to 0° C. TsOH.H$_2$O (38.5 mg, 0.2 mmol, 2 equiv) was added to the solution, followed by Rh$_2$(esp)$_2$ (2.3 mg, 3 μmmol, 0.03 equiv) 10 min later. The mixture was stirred vigorously for 30 min at 0° C., poured into saturated sodium carbonate solution (10 mL), and extracted with DCM (3×5 mL). The combined organic extracts was dried over anhydrous Na$_2$SO$_4$, decanted and concentrated on a rotary evaporator. The crude material was purified on a Teledyne Isco Combiflash purification system using methanol and dichloromethane as eluent to give the aminated product (8x: 17.5 mg, 46%) as a light brown solid. TLC: R$_f$≈0.3 (10% MeOH/CH$_2$Cl$_2$); $^1$H NMR (500 MHz, CD$_3$OD) δ 6.02 (s, 1H), 5.60 (dt, J=10.1, 2.2 Hz, 1H), 5.46 (dt, J=10.1, 2.2 Hz, 1H), 5.17-5.13 (m, 1H), 4.99 (d, J=7.1 Hz, 1H), 4.21-4.09 (m, 2H), 3.60-3.56 (m, 1H), 2.82 (d, J=18.7 Hz, 1H), 2.80-2.77 (m, 1H), 2.76 (s, 3H), 2.72 (dd, J=12.5, 4.2 Hz, 1H), 2.54 (s, 3H), 2.47 (dt, J=12.5, 3.4 Hz, 1H), 2.20 (dd, J=18.7, 6.25 Hz, 1H), 2.12 (s, 3H), 2.08 (dt, J=12.8, 5.0 Hz, 1H), 1.87-1.82 (complex m, 1H), 1.33 (t, J=6.7 Hz, 3H); $^{13}$C NMR (125 MHz, CD$_3$OD) δ 170.66, 141.53, 141.42, 138.72, 130.50, 128.16, 127.98, 112.00, 98.72, 86.76, 67.90, 65.29, 59.01, 46.49, 41.93, 41.31, 38.91, 33.94, 30.06, 19.21, 17.11, 14.09. HRMS (ESI$^+$) Calcd. for [C$_{22}$H$_{28}$N$_2$O$_4$+H]$^+$ 385.2127, Found 385.2115.

NMR data were collected on a Varian NMR-S 500 MHz console using a OneNMR probe with the sample at 294 K. Chemical shifts are reported in delta (δ) units, in parts per million (ppm) downfield from tetramethylsilane. Proton nuclear magnetic resonance (1H-NMR) data are reported as follows: s (singlet), d (doublet), t (triplet), q (quartet), dd (doublet of doublets), dt (doublet of triplets), dq (doublet of quartets), m (multiplet), dm (doublet of multiplets). Coupling constants are reported in hertz (Hz). 2D NMR data are summarized in table S1 and the parameters used for the 2D protocols are summarized in table S2. Atom positions are given relative to the labeling below.

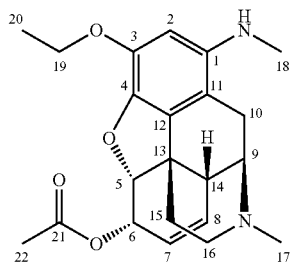 [SMILES: CCOc1cc(NC)c2c3c1O[C@H]1[C@@H](OC(C)=O)C=C[C@H]4[C@@H](C2)N(C)CC[C@@]341]

The position on the aromatic ring that was aminated was confirmed using both HMBC and NOESY data. The HMBC data is consistent with amination at C1:C10 sees H2 ($^4J_{CH}$) and C2 sees both H10a & H10b ($^4J_{CH}$); but, C2 does not see H9. Furthermore, C11 sees H2 ($^3J_{CH}$) while C12 does not see H2. Most importantly, C4 sees H2 ($^3J_{CH}$). The NOESY data confirms this conclusion with H2 showing strong correlations to both H19 (a & b) and H18, but not H10; and H18 showing strong correlations to both H2 and H10 (a & b), but not H19 or H20. The only arrangement consistent these data is amination at C1.

TABLE S1

| | | | | | | |
|---|---|---|---|---|---|---|
| NMR Summary for AA-IX-174 in CD$_3$OD | | | | | | |
| Position | Type | $^{13}$C (ppm) | $^1$H (ppm) | COSY | HMBC | NOESY |
| 1 | C | 141.42 | — | — | 2, 10a, 10b, 18 | — |
| 2 | CH | 98.72 | 6.02 | — | 10a, 10b | 18, 19a, 19b |
| 3 | C | 141.53 | — | — | 2, 19a, 19b | — |
| 4 | C | 138.72 | — | — | 2, 5 | — |
| 5 | CH | 86.76 | 4.99 | 6 | 15b | 6, 14, 15a, 15b |
| 6 | CH | 67.90 | 5.13 | 5, 7, 8, 14 | — | 5, 8, 14 |
| 7 | CH | 127.98 | 5.46 | 6, 8, 14 | 5, 8 | 8, 9, 10a, 14 |
| 8 | CH | 128.16 | 5.60 | 6, 7, 14 | 5, 7 | 6, 7 |
| 9 | CH | 59.01 | 3.58 | 10a, 14 | 10a, 10b, 16b, 17 | 7, 10a, 10b, 14, 17 |
| 10 | CH$_2$ | 17.11 | 2.20/2.82 | 9, 10b/10a | 2 | 7, 9, 10b/9, 10a, 16a, 17, 18 |
| 11 | C | 112.00 | — | — | 2, 9, 10a, 10b | — |
| 12 | C | 130.50 | — | — | 5, 10a, 10b, 15b | — |
| 13 | C | 41.93 | — | — | 9, 15a, 15b, 16b | — |
| 14 | CH | 38.91 | 2.78 | 6, 7, 8, 9 | 7, 8, 9, 10b, 15a, 15b | 5, 6, 7, 9 |
| 15 | CH$_2$ | 33.94 | 1.84/2.08 | 15b, 16a/15a, 16a, 16b | 5, 16b, 17 | 5, 15b, 16a, 16b/5, 14, 15a, 16b |
| 16 | CH$_2$ | 46.49 | 2.47/2.72 | 15a, 15b, 16b/15b, 16a | 9, 15b, 17 | 15a, 16b, 17/15a, 15b, 16a, 17 |
| 17 | CH$_3$ | 41.31 | 2.54 | — | 9, 15b, 16b | 9, 10b, 16a, 16b |
| 18 | CH$_3$ | 30.06 | 2.76 | — | — | 2, 10b |
| 19 | CH$_2$ | 65.29 | 4.11/4.15 | 20/20 | 20 | 2, 20/2, 20 |
| 20 | CH$_3$ | 14.09 | 1.33 | 19a, 19b | 19a, 19b | 19a, 19b |
| 21 | C | 170.66 | — | — | 22 | — |
| 22 | CH$_3$ | 19.21 | 2.12 | — | — | — |

TABLE S2

NMR Protocols

| Protocol | Scans | t1 incr. | Other Key Parameters |
|---|---|---|---|
| Proton | 64 | | |
| Carbon | 25,000 | | |
| gDQCOSY | 16 | 512 | |
| HSQCAD | 64 | 96 | J1 = 146 Hz |
| gHMBCAD | 96 | 96 | Jn = 8 Hz |
| NOESY | 32 | 512 | mixing time = 500 ms, ZQ-filtered |

Note:
90° pulse widths were 8.4 μs for $^1$H and 9.8 μs for $^{13}$C
All spectra were collected with a 1 s relaxation delay.
All 2D transients were preceded by a grad-90°-grad steady-state pulse.

FIG. 2: Entry 21

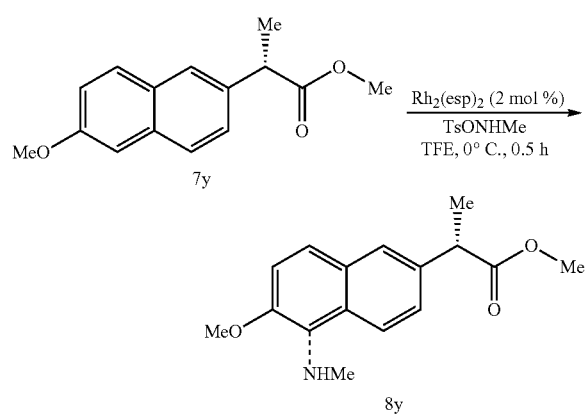

Following the general intermolecular amination procedure, naproxen methyl ester (7y: 73 mg, 0.3 mmol), Du Bois' catalyst (4.5 mg, 6.0 μmol), and TsONHMe (90 mg, 0.45 mmol) were stirred in TFE (3 mL) at 0° C. for 0.5 h. Chromatographic purification of the crude product afforded methyl (S)-2-(6-methoxy-5-(methylamino)naphthalen-2-yl) propanoate (8y) as a pale yellow oil (57 mg, 69%). TLC: $R_f$=0.4 (30% EtOAc/hexanes); $^1$H NMR (400 MHz, CDC$_3$) δ 8.04 (d, J=8.8 Hz, 1H), 7.65 (d, J=1.4 Hz, 1H), 7.46 (d, J=8.4 Hz, 1H), 7.40 (dd, J=8.8, 1.9 Hz, 1H), 7.24 (d, J=8.9 Hz, 1H), 3.94 (s, 3H), 3.86 (q, J=7.2 Hz, 1H), 3.67 (s, 3H), 2.97 (s, 3H), 1.58 (d, J=7.1 Hz, 3H); $^{13}$C NMR (101 MHz, CDCl$_3$) δ 175.11, 147.37, 135.51, 133.98, 129.91, 127.24, 126.39, 125.07, 123.39, 122.24, 113.79, 56.85, 52.02, 45.24, 37.13, 18.47. HRMS (ESI$^+$) Calcd. for [C$_{16}$H$_{19}$NO$_3$+H]$^+$ 274.1443, Found 274.1438.

A. 5.1.2 General Mitsunobu Procedure

Diisopropyl azodicarboxylate (DIAD: 1.2 equiv) was added to a stirring, 0° C. solution of triphenylphosphine (1.2 equiv) in dry THF under an argon atmosphere. A white precipitate developed after stirring for about 10 min. After 30 min total, a solution of alcohol (1.0 equiv) in dry THF and tert-butyl tosyloxycarbamate (TsONH$^t$Boc: 1.2 equiv) were added successively. The ice bath was removed after 1 h and the reaction mixture was stirred for 2-24 h. The volatiles were then removed in vacuo and, unless otherwise stated, the residue was purified with a pre-packed SiO$_2$ column on a medium pressure, automated chromatograph using EtOAc/hexanes as eluent to furnish the $^t$Boc-amino adduct.

B. 5.1.3 General Intramolecular Aza-Annulation Procedure

To a stirring, 0° C. solution of $^t$Boc-protected amino adduct (1.0 equiv) in 2,2,2-trifluoroethanol were added sequentially trifluoroacetic acid (TFA, 2.0 equiv) and Rh$_2$(esp)$_2$ (2 mol %). After stirring for 2 h, the cold bath was removed and the stirring was continued for an additional 16-22 h. The reaction mixture was diluted with CH$_2$Cl$_2$ and washed successively with saturated aqueous Na$_2$CO$_3$ and brine. The organic layer was dried over anhydrous Na$_2$SO$_4$ and concentrated in vacuo. The crude product was purified with a pre-packed SiO$_2$ column on a medium pressure, automated chromatograph using EtOAc/hexanes as eluent to furnish an N-heterocycle.

Intramolecular Aza-Annulation Experimental

FIG. 3: Entry 1

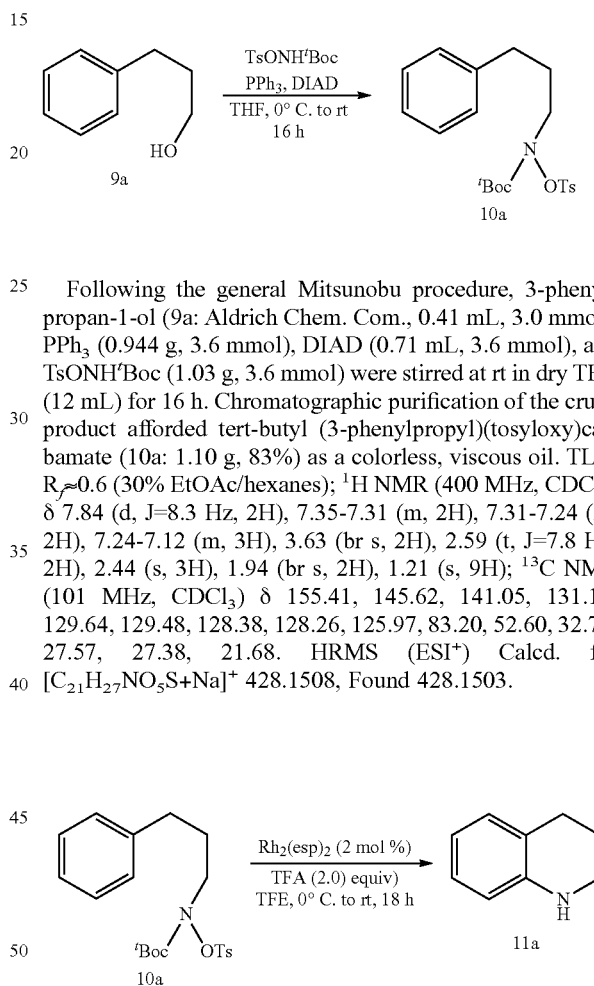

Following the general Mitsunobu procedure, 3-phenyl-propan-1-ol (9a: Aldrich Chem. Com., 0.41 mL, 3.0 mmol), PPh$_3$ (0.944 g, 3.6 mmol), DIAD (0.71 mL, 3.6 mmol), and TsONH$^t$Boc (1.03 g, 3.6 mmol) were stirred at rt in dry THF (12 mL) for 16 h. Chromatographic purification of the crude product afforded tert-butyl (3-phenylpropyl)(tosyloxy)carbamate (10a: 1.10 g, 83%) as a colorless, viscous oil. TLC: $R_f$=0.6 (30% EtOAc/hexanes); $^1$H NMR (400 MHz, CDCl$_3$) δ 7.84 (d, J=8.3 Hz, 2H), 7.35-7.31 (m, 2H), 7.31-7.24 (m, 2H), 7.24-7.12 (m, 3H), 3.63 (br s, 2H), 2.59 (t, J=7.8 Hz, 2H), 2.44 (s, 3H), 1.94 (br s, 2H), 1.21 (s, 9H); $^{13}$C NMR (101 MHz, CDCl$_3$) δ 155.41, 145.62, 141.05, 131.17, 129.64, 129.48, 128.38, 128.26, 125.97, 83.20, 52.60, 32.78, 27.57, 27.38, 21.68. HRMS (ESI$^+$) Calcd. for [C$_{21}$H$_{27}$NO$_5$S+Na]$^+$ 428.1508, Found 428.1503.

Following the general intramolecular aza-annulation procedure, tert-butyl (3-phenylpropyl)(tosyloxy)carbamate (10a: 0.101 g, 0.25 mmol), TFA (38 μL, 0.5 mmol), and Du Bois' catalyst (3.8 mg, 5 μmol) were stirred at rt in TFE (2.5 mL) for 18 h. Chromatographic purification of the crude product afforded 1,2,3,4-tetrahydroquinoline (11a: 27 mg, 81%) as an oil whose spectral data were in agreement with literature values in Ortiz-Marciales, et al., 2005. TLC: $R_f$=0.6 (30% EtOAc/hexanes); $^1$H NMR (400 MHz, CDCl$_3$) δ 7.00-6.91 (m, 2H), 6.60 (td, J=7.4, 1.2 Hz, 1H), 6.51-6.44

(m, 1H), 3.37-3.25 (m, 2H), 2.76 (t, J=6.4 Hz, 2H), 2.01-1.86 (m, 2H); $^{13}$C NMR (101 MHz, CDCl$_3$) δ 144.65, 129.48, 126.68, 121.46, 116.96, 114.18, 41.95, 26.92, 22.13.

FIG. 3: Entry 2

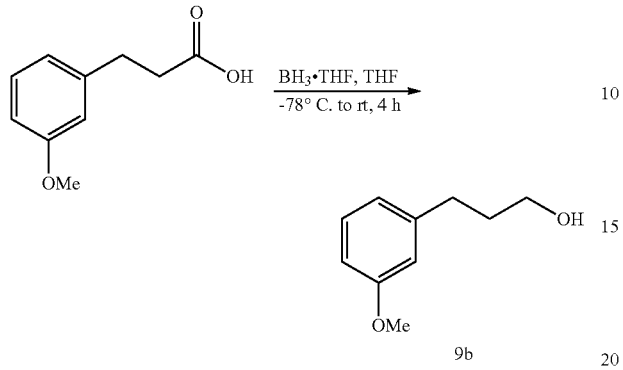

A solution of BH$_3$·THF (1.0 M in THF, 3.6 mL, 3.6 mmol) was added dropwise to a −78° C. solution of 3-(3-methoxyphenyl)propanoic acid (0.541 g, 3.0 mmol; Aldrich Chem. Co.) in anhydrous THF (9.0 mL). After 1 h, the reaction temperature was raised to 0° C. and the stirring was continued for another 4 h, and then quenched with excess methanol. All volatiles were removed in vacuo and the residue was purified by chromatography using 40% EtOAc/hexanes as eluent to furnish 3-(3-methoxyphenyl)propan-1-ol (9b: 0.450 g, 90%) as a colorless oil whose spectral data were in agreement with literature values in Manas and Smith, 1987. TLC: R$_f$=0.3 (40% EtOAc/hexanes); $^1$H NMR (400 MHz, CDCl$_3$) δ 7.26-7.16 (m, 1H), 6.82-6.78 (m, 1H), 6.77-6.72 (m, 2H), 3.80 (s, 3H), 3.67 (t, J=6.4 Hz, 2H), 2.69 (t, J=6.4 Hz, 2H), 1.96-1.82 (m, 2H), 1.59 (br s, 1H); $^{13}$C NMR (101 MHz, CDCl$_3$) δ 159.63, 143.46, 129.35, 120.83, 114.20, 111.10, 62.25, 55.13, 34.09, 32.13.

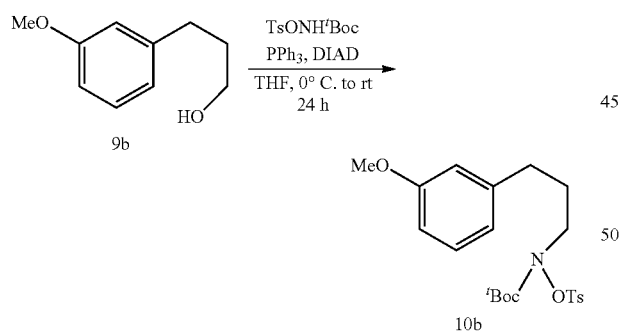

Following the general Mitsunobu procedure, 3-(3-methoxyphenyl)propan-1-ol (9b: 0.309 g, 1.86 mmol), PPh$_3$ (0.585 g, 2.23 mmol), DIAD (0.44 mL, 2.23 mmol), and TsONH$^t$Boc (0.641 g, 2.23 mmol) were stirred in dry THF (10 mL) at rt for 24 h. Chromatographic purification of the crude product afforded tert-butyl (3-(3-methoxyphenyl)propyl)(tosyloxy)carbamate (10b: 0.740 g, 91%) as a colorless, viscous oil. TLC: R$_f$=0.7 (40% EtOAc/hexanes); $^1$H NMR (400 MHz, CDCl$_3$) δ 7.84 (d, J=8.3 Hz, 2H), 7.32 (d, J=8.2 Hz, 2H), 7.19 (t, J=7.8 Hz, 1H), 6.79-6.65 (m, 3H), 3.79 (s, 3H), 3.61 (br s, 2H), 2.57 (t, J=7.8 Hz, 2H), 2.44 (s, 3H), 1.95 (br s, 2H), 1.21 (s, 9H); $^{13}$C NMR (101 MHz, CDCl$_3$) δ 159.64, 155.42, 145.66, 142.68, 131.17, 129.65, 129.50, 129.36, 120.66, 113.93, 111.41, 83.23, 55.14, 52.58, 32.84, 27.58, 27.29, 21.69. HRMS (ESI$^+$) Calcd. for [C$_{22}$H$_{29}$N$_6$S+Na]$^+$ 458.1613, Found 458.1620.

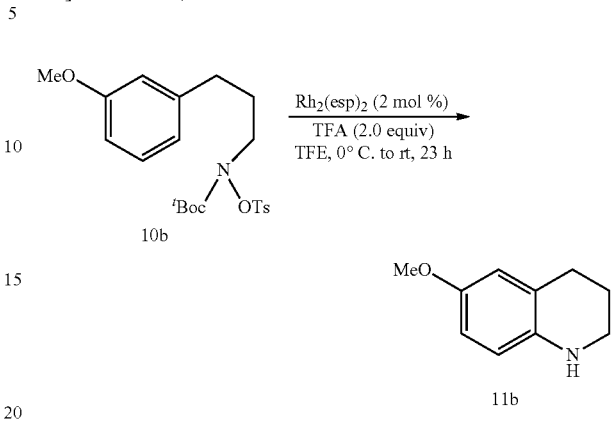

Following the general intramolecular aza-annulation procedure, tert-butyl (3-(3-methoxyphenyl)propyl)(tosyloxy)carbamate (10b: 87 mg, 0.20 mmol), TFA (31 μL, 0.4 mmol), and Du Bois' catalyst (3.0 mg, 4 μmol) were stirred at rt in TFE (2.0 mL) for 23 h. Chromatographic purification of the crude product afforded 6-methoxy-1,2,3,4-tetrahydroquinoline (11b: 28 mg, 86%) as an oil whose spectral data were in agreement with literature values in Chen, et al., 2015. TLC: R$_f$=0.5 (20% EtOAc/hexanes); $^1$H NMR (400 MHz, CDCl$_3$) δ 6.64-6.54 (m, 2H), 6.45 (d, J=8.5 Hz, 1H), 3.73 (s, 3H), 3.25 (t, J=6.5 Hz, 2H), 2.76 (t, J=6.5 Hz, 2H), 1.98-1.89 (m, 2H); $^{13}$C NMR (101 MHz, CDCl$_3$) δ 151.89, 138.59, 123.00, 115.68, 114.84, 112.86, 55.78, 42.32, 27.11, 22.37.

FIG. 3: Entry 3

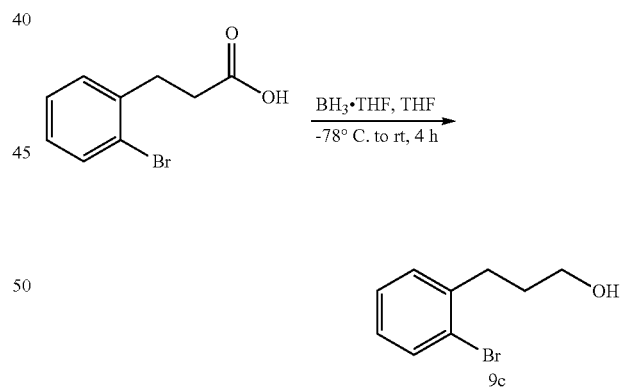

Following the acid reduction procedure as applied to 9b, 3-(2-bromophenyl)propanoic acid (0.916 g, 4.0 mmol; Aldrich Chem. Co.), and BH$_3$·THF (1.0 M in THF, 4.8 mL, 4.8 mmol) were reacted in THF (10 mL). Chromatographic purification of the crude product afforded 3-(2-bromophenyl)propan-1-ol (9c) as a colorless oil (0.732 g, 85%) whose spectral values were in agreement with literature values in Cooke, et al., 1987. TLC: R$_f$=0.6 (40% EtOAc/hexanes); $^1$H NMR (400 MHz, CDCl$_3$) δ 7.59-7.47 (m, 1H), 7.27-7.21 (m, 2H), 7.09-7.02 (m, 1H), 3.70 (t, J=6.3 Hz, 2H), 2.91-2.77 (m, 2H), 1.97-1.81 (m, 2H), 1.46 (br s, 1H).

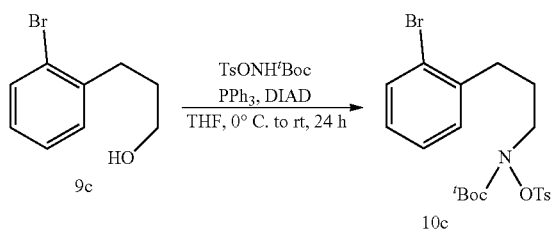

Following the general Mitsunobu procedure, 3-(2-bromophenyl)propan-1-ol (9c: 0.215 g, 1.0 mmol), PPh$_3$ (0.315 g, 1.2 mmol), DIAD (0.24 mL, 1.2 mmol), and TsONHBoc (0.345 g, 1.2 mmol) were stirred at rt in dry THF (5 mL) for 24 h. Chromatographic purification of the crude product afforded tert-butyl (3-(2-bromophenyl)propyl)(tosyloxy) carbamate (10c: 0.422 g, 87%) as colorless solid, mp 55.2° C. TLC: R$_f$=0.6 (20% EtOAc/hexanes); $^1$H NMR (400 MHz, CDCl$_3$) δ 7.84 (d, J=8.3 Hz, 2H), 7.50 (dd, J=8.0, 1.2 Hz, 1H), 7.32 (d, J=8.6 Hz, 2H), 7.27-7.16 (m, 2H), 7.12-6.97 (m, 1H), 3.66 (br s, 2H), 2.70 (t, J=7.9 Hz, 2H), 2.43 (s, 3H), 2.09-1.83 (m, 2H), 1.22 (s, 9H); $^{13}$C NMR (101 MHz, CDCl$_3$) δ 155.34, 145.70, 140.37, 132.80, 131.14, 130.17, 129.64, 129.52, 127.78, 127.51, 124.35, 83.28, 52.52, 33.12, 27.60, 26.04, 21.71. HRMS (ESI$^+$) Calcd. for [C$_{21}$H$_{26}$NO$_5$SBr+Na]$^+$ 506.0613, Found 506.0613.

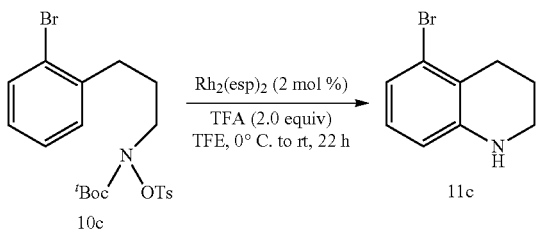

Following the general intramolecular aza-annulation procedure, tert-butyl (3-(2-bromophenyl)propyl)(tosyloxy)carbamate (10c: 0.121 g, 0.25 mmol), TFA (38 μL, 0.5 mmol), and Du Bois' catalyst (3.8 mg, 5 μmol) were stirred at rt in TFE (2.5 mL) for 22 h. Chromatographic purification of the crude product afforded 5-bromo-1,2,3,4-tetrahydroquinoline (11c) as an oil (41 mg, 77%). TLC: R$_f$=0.6 (20% EtOAc/hexanes); $^1$H NMR (400 MHz, CDCl$_3$) δ 6.93-6.75 (m, 2H), 6.41 (dd, J=7.8, 1.3 Hz, 1H), 3.89 (br s, 1H), 3.33-3.19 (m, 2H), 2.77 (t, J=6.6 Hz, 2H), 2.04-1.88 (m, 2H); $^{13}$C NMR (101 MHz, CDCl$_3$) δ 146.46, 127.54, 125.96, 120.75, 120.68, 113.16, 41.46, 27.64, 22.20. HRMS (ESI$^+$) Calcd. for [C$_9$H$_{10}$NBr+H]$^+$ 212.0075, Found 212.0073.

FIG. 3: Entry 4

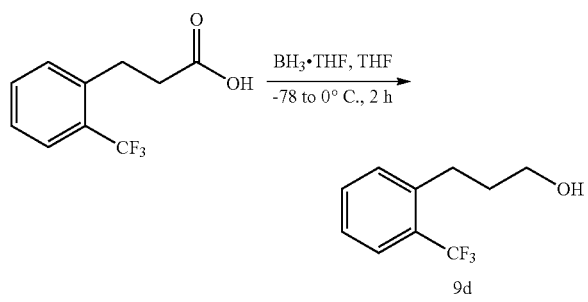

Following the acid reduction procedure as applied to 9b, 3-(2-(trifluoromethyl)phenyl)propanoic acid (0.654 g, 3.0 mmol; Aldrich Chem. Co.) and BH$_3$.THF (1.0 M in THF, 3.6 mL, 3.6 mmol) were reacted in THF (9 mL). Chromatographic purification of the crude product afforded 3-(2-(trifluoromethyl)phenyl)propan-1-ol (9d) as a colorless oil (0.570 g, 93%) whose spectral data were in agreement with literature values in de Haan, et al., 1997. TLC: R$_f$=0.5 (40% EtOAc/hexanes); $^1$H NMR (400 MHz, CDCl$_3$) δ 7.60 (d, J=7.9 Hz, 1H), 7.45 (t, J=7.5 Hz, 1H), 7.34 (d, J=7.7 Hz, 1H), 7.27 (t, J=7.7 Hz, 1H), 3.71 (t, J=3.1 Hz, 2H), 2.86 (t, J=6.9 Hz, 2H), 1.95-1.76 (m, 2H), 1.51 (br s, 1H).

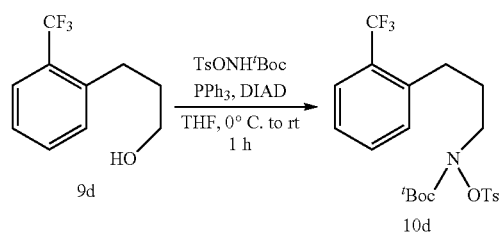

Following the general Mitsunobu procedure, 3-(2-(trifluoromethyl)phenyl)propan-1-ol (9d: 0.204 g, 1.0 mmol), PPh$_3$ (0.315 g, 1.2 mmol), DIAD (0.24 mL, 1.2 mmol), and TsONHBoc (0.345 g, 1.2 mmol) were stirred at rt in dry THF (5 mL) for 1 h. Chromatographic purification of the crude product afforded tert-butyl tosyloxy(3-(2-(trifluoromethyl)phenyl)propyl)carbamate (10d) as a colorless, viscous oil (0.450 g, 95%). TLC: R$_f$=0.6 (30% EtOAc/hexanes); $^1$H NMR (400 MHz, CDCl$_3$) δ 7.85 (d, J=8.3 Hz, 2H), 7.60 (d, J=7.9 Hz, 1H), 7.47 (t, J=7.5 Hz, 1H), 7.33 (d, J=8.3 Hz, 2H), 7.31-7.27 (m, 2H), 3.67 (br s, 2H), 2.75 (t, J=8.0 Hz, 2H), 2.44 (s, 3H), 1.95 (br s, 2H), 1.22 (s, 9H); $^{13}$C NMR (101 MHz, CDCl$_3$) δ 155.31, 145.68, 139.93 (q, $^4J_{C,F}$=2 Hz), 131.83, 131.12, 130.75, 129.64, 129.49, 128.33 (q, $^2J_{C,F}$=30 Hz), 126.10, 125.91 (q, $^3J_{C,F}$=6 Hz), 124.62 (q, $^1J_{C,F}$=272 Hz), 83.32, 52.68, 29.50 (q, $^4J_{C,F}$=2 Hz), 27.73, 27.54, 21.67. HRMS (ESI$^+$) Calcd. for [C$_{22}$H$_{26}$F$_3$NO$_5$S+Na]$^+$ 496.1382, Found 496.1382.

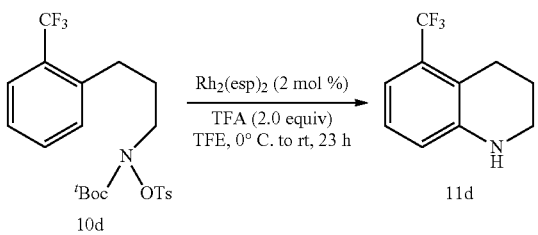

Following the general intramolecular aza-annulation procedure, tert-butyl tosyloxy(3-(2-(trifluoromethyl)phenyl)propyl)carbamate (10d: 0.142 g, 0.3 mmol), TFA (46 μL, 0.6 mmol), and Du Bois' catalyst (4.5 mg, 6 μmol) were stirred at rt in TFE (3.0 mL) for 23 h. Chromatographic purification of the crude product afforded 5-(trifluoromethyl)-1,2,3,4-tetrahydroquinoline (11d) as an oil (46 mg, 77%). TLC: R$_f$=0.7 (30% EtOAc/hexanes); $^1$H NMR (400 MHz, CDCl$_3$) δ 7.08-6.95 (m, 1H), 6.92 (d, J=7.2 Hz, 1H), 6.60 (d, J=8.0 Hz, 1H), 3.91 (br s, 1H), 3.38-3.25 (m, 2H), 2.91 (t, J=6.3 Hz, 2H), 2.02-1.87 (m, 2H); $^{13}$C NMR (101 MHz, CDCl$_3$) δ 145.55, 129.10 (q, $^2J_{C,F}$=29 Hz), 126.26, 124.74 (q, $^1J_{C,F}$=273 Hz), 119.0 (q, $^4J_{C,F}$=2 Hz), 117.70 (q, $^4J_{C,F}$=1

Hz), 114.21 (q, $^3J_{C,F}$=6 Hz), 41.31, 23.40 (q, $^4J_{C,F}$=2 Hz), 21.37. HRMS (ESI$^+$) Calcd. for $[C_{10}H_{10}F_3N+H]^+$ 202.0844, Found 202.0840.

FIG. 3: Entry 5

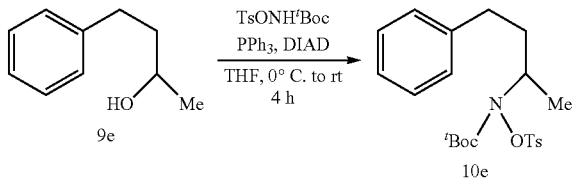

Following the general Mitsunobu procedure, 4-phenylbutan-2-ol (9e: TCI America, 0.150 g, 1.0 mmol), PPh$_3$ (0.315 g, 1.2 mmol), DIAD (0.24 mL, 1.2 mmol), and TsONHBoc (0.345 g, 1.2 mmol) were stirred in dry THF (5 mL) at rt for 4 h. Chromatographic purification of the crude product afforded tert-butyl (4-phenylbutan-2-yl)(tosyloxy)carbamate (10e) as a colorless, viscous oil (0.387 g, 92%) along with some impurity which was used for the next step without further purification. An analytical sample was purified by preparative TLC (2% EtOAc/toluene). TLC: $R_f$≈0.7 (30% EtOAc/hexanes); $^1$H NMR (400 MHz, CDCl$_3$) δ 7.87 (d, J=8.3 Hz, 2H), 7.33 (d, J=8.3 Hz, 2H), 7.30-7.21 (m, 2H), 7.22-7.13 (m, 3H), 4.08-3.94 (m, 1H), 2.74-2.60 (m, 2H), 2.43 (s, 3H), 2.12-2.00 (m, 1H), 1.73 (br s, 1H), 1.27 (s, 9H), 1.22 (d, J=6.7 Hz, 3H); $^{13}$C NMR (101 MHz, CDCl$_3$) δ 156.26, 145.49, 141.65, 131.72, 129.58, 129.47, 128.39, 128.33, 125.84, 83.34, 60.68, 35.66, 32.88, 27.66, 21.68, 17.28. HRMS (ESI$^+$) Calcd. for $[C_{22}H_{29}NO_5S+Na]^+$ 442.1664. Found 442.1659.

MHz, CDCl$_3$) δ 144.77, 129.28, 126.69, 121.11, 116.98, 114.01, 47.17, 30.14, 26.61, 22.63.

FIG. 3: Entry 6

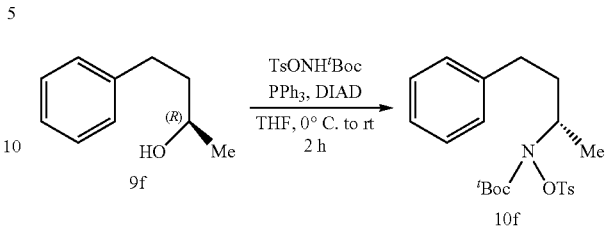

Following the general Mitsunobu procedure, (R)-4-phenylbutan-2-ol (9f: 0.150 g, 1.0 mmol; Aldrich Chem. Co.), PPh$_3$ (0.315 g, 1.2 mmol), DIAD (0.24 mL, 1.2 mmol), and TsONHWBoc (0.345 g, 1.2 mmol) were stirred at rt in dry THF (5 mL) for 2 h. Chromatographic purification of the crude product afforded (S)-tert-butyl (4-phenylbutan-2-yl)(tosyloxy)carbamate (10f: 0.377 g, 90%) as a colorless viscous oil accompanied by a minor impurity, that was used for the next step without further purification. An analytical sample was purified by preparative TLC (2% EtOAc/toluene). TLC: $R_f$≈0.7 (30% EtOAc/hexanes); $^1$H NMR (400 MHz, CDCl$_3$) δ 7.87 (d, J=8.3 Hz, 2H), 7.33 (d, J=8.3 Hz, 2H), 7.30-7.24 (m, 2H), 7.22-7.15 (m, 3H), 4.08-3.94 (m, 1H), 2.74-2.60 (m, 2H), 2.43 (s, 3H), 2.12-2.00 (m, 1H), 1.73 (br s, 1H), 1.27 (s, 9H), 1.22 (d, J=6.7 Hz, 3H); $^{13}$C NMR (101 MHz, CDCl$_3$) δ 156.26, 145.49, 141.65, 131.72, 129.58, 129.47, 128.39, 128.33, 125.84, 83.34, 60.68, 35.66, 32.88, 27.66, 21.68, 17.28. HRMS (ESI$^+$) Calcd. for $[C_{22}H_{29}NO_5S+Na]^+$ 442.1664, Found 442.1667.

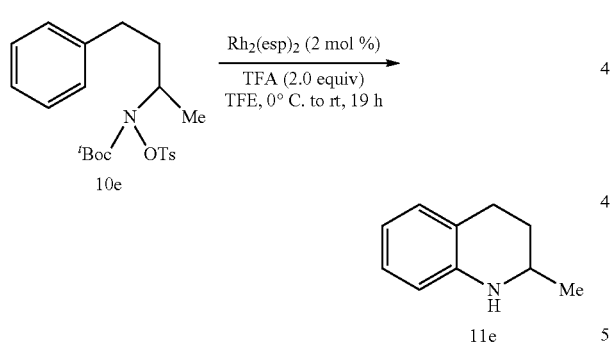

Following the general intramolecular aza-annulation procedure, tert-butyl (4-phenylbutan-2-yl)(tosyloxy)carbamate (10e: 0.105 g, 0.25 mmol), TFA (38 µL, 0.5 mmol), and Du Bois' catalyst (3.8 mg, 5 µmol) were stirred at rt in TFE (2.5 mL) for 19 h. Chromatographic purification of the crude product afforded 2-methyl-1,2,3,4-tetrahydroquinoline (11e) as an oil (31 mg, 84%) whose spectral data were in agreement with literature values in Sridharan, et al., 2007. The enantiomers were resolved with baseline separation using a Chiralcel® OJ-H HPLC column (vide infra). TLC: $R_f$≈0.7 (20% EtOAc/hexanes); $^1$H NMR (400 MHz, CDCl$_3$) δ 7.07-6.94 (m, 2H), 6.63 (td, J=7.4, 1.2 Hz, 1H), 6.49 (dd, J=8.3, 1.2 Hz, 1H), 3.60 (br s, 1H), 3.46-3.36 (m, 1H), 2.94-2.82 (m, 1H), 2.82-2.69 (m, 1H), 2.01-1.89 (m, 1H), 1.67-1.55 (m, 1H), 1.23 (d, J=6.3 Hz, 3H); $^{13}$C NMR (101

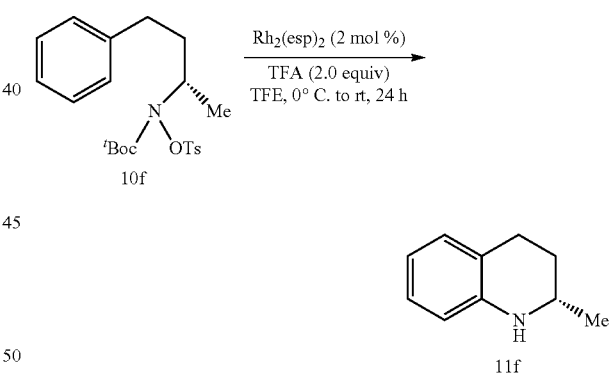

Following the general intramolecular aza-annulation procedure, (S)-tert-butyl (4-phenylbutan-2-yl)(tosyloxy)carbamate (10f: 0.105 g, 0.25 mmol), TFA (38 µL, 0.5 mmol), and Du Bois' catalyst (3.8 mg, 5 µmol) were stirred at rt in TFE (2.5 mL) for 24 h. Chromatographic purification of the crude product afforded (S)-2-methyl-1,2,3,4-tetrahydroquinoline (11f) as an oil (30 mg, 82%) whose spectral data were in agreement with literature values in Wang, et al., 2003. Chiral HPLC analysis showed 11f consisted >99% of the S-enantiomer. TLC: $R_f$≈0.7 (20% EtOAc/hexanes); $^1$H NMR (400 MHz, CDCl$_3$) δ 7.04-6.93 (m, 2H), 6.62 (td, J=7.4, 1.2 Hz, 1H), 6.49 (dd, J=8.3, 1.2 Hz, 1H), 3.70 (br s, 1H), 3.49-3.36 (m, 1H), 2.95-2.80 (m, 1H), 2.80-2.69 (m, 1H), 2.01-1.90 (m, 1H), 1.68-1.54 (m, 1H), 1.23 (d, J=6.3

Hz, 3H); ¹³C NMR (101 MHz, CDCl₃) δ 144.77, 129.28, 126.69, 121.11, 116.98, 114.01, 47.17, 30.14, 26.61, 22.63.

FIG. 3: Entry 7

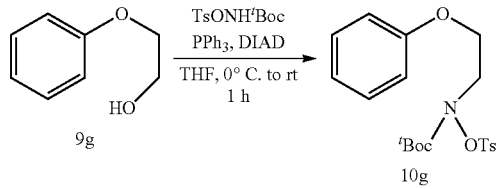

Following the general Mitsunobu procedure, 2-phenoxyethanol (9g: 0.138 g, 1.0 mmol; TCI America), PPh₃ (0.315 g, 1.2 mmol), DIAD (0.24 mL, 1.2 mmol), and TsONH$^t$Boc (0.345 g, 1.2 mmol) were reacted in dry THF (5 mL) for 1 h. Chromatographic purification of the crude product afforded tert-butyl (2-phenoxyethyl)(tosyloxy)carbamate (10g: 0.370 g, 91%) as a colorless solid, mp 70.3° C. TLC: $R_f$≈0.6 (30% EtOAc/hexanes); ¹H NMR (400 MHz, CDCl₃) δ 7.87 (d, J=8.3 Hz, 2H), 7.34 (d, J=8.1 Hz, 2H), 7.26 (t, J=8.0 Hz, 2H), 6.94 (t, J=7.4 Hz, 1H), 6.85 (d, J=8.7 Hz, 2H), 4.19 (br s, 4H), 2.45 (s, 3H), 1.22 (s, 9H); ¹³C NMR (101 MHz, CDCl₃) δ 158.30, 155.32, 145.82, 130.93, 129.75, 129.55, 129.40, 121.07, 114.57, 83.35, 62.75, 51.42, 27.55, 21.70. HRMS (ESI⁺) Calcd. for [C₂₀H₂₅NO₆S+Na]⁺ 430.1300, Found 430.1307.

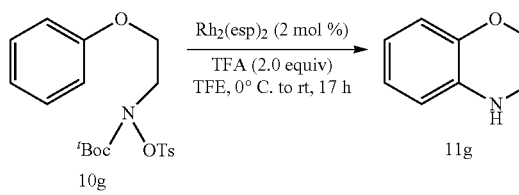

Following the general intramolecular aza-annulation procedure, tert-butyl (2-phenoxyethyl)(tosyloxy)carbamate (10g: 0.102 g, 0.25 mmol), TFA (38 µL, 0.5 mmol), and Du Bois' catalyst (3.8 mg, 5 µmol) were stirred at rt in TFE (2.5 mL) for 17 h. Chromatographic purification of the crude product afforded 3,4-dihydro-2H-benzo[b][1,4]oxazine (11g) as an oil (28 mg, 82%) whose spectral data were in agreement with literature values in Dugar, et al., 2015. TLC: $R_f$≈0.4 (30% EtOAc/hexanes); ¹H NMR (400 MHz, CDCl₃) δ 6.82-6.74 (m, 2H), 6.70-6.63 (m, 1H), 6.60 (dd, J=7.7, 1.6 Hz, 1H), 4.26 (app t, J=4.5 Hz, 2H), 3.74 (br s, 1H), 3.42 (app t, J=4.5, 2H); ¹³C NMR (101 MHz, CDCl₃) δ 144.11, 133.64, 121.28, 118.85, 116.73, 115.63, 65.22, 40.99.

FIG. 3: Entry 8

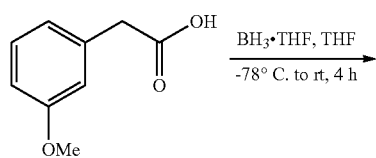

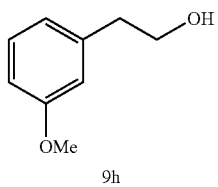

Following the acid reduction procedure as applied to 9b, 2-(3-methoxyphenyl)acetic acid (1.16 g, 7.0 mmol; Aldrich Chem. Co.) and BH₃·THF (1.0 M in THF, 8.4 mL, 8.4 mmol) were reacted in THF (20 mL) for 4 h. Chromatographic purification of the crude product afforded 2-(3-methoxyphenyl)ethanol (9h) as a colorless oil (1.05 g, 98%) whose spectral data were in agreement with literature values in Gómez, et al., 2006. TLC: $R_f$≈0.5 (30% EtOAc/hexanes); ¹H NMR (400 MHz, CDCl₃) δ 7.30-7.19 (m, 1H), 6.87-6.73 (m, 3H), 3.89-3.82 (m, 2H), 3.80 (s, 3H), 2.84 (t, J=6.5 Hz, 2H), 1.59 (br s, 1H); ¹³C NMR (101 MHz, CDC₃) 159.75, 140.08, 129.57, 121.33, 114.76, 111.75, 63.56, 55.15, 39.22.

Following the general Mitsunobu procedure, 2-(3-methoxyphenyl)ethanol (9h: 0.152 g, 1.0 mmol), PPh₃ (0.315 g, 1.2 mmol), DIAD (0.24 mL, 1.2 mmol), and TsONH$^t$Boc (0.345 g, 1.2 mmol) were stirred at rt in dry THF (5 mL) for 19 h. Chromatographic purification of the crude product afforded tert-butyl 3-methoxyphenethyl(tosyl) carbamate (10h) as a colorless, viscous oil (0.325 g, 77%). TLC: $R_f$≈0.6 (30% EtOAc/hexanes); ¹H NMR (400 MHz, CDCl₃) δ 7.86 (d, J=8.3 Hz, 2H), 7.34 (d, J=8.3 Hz, 2H), 7.18 (t, J=7.8 Hz, 1H), 6.82-6.68 (m, 3H), 3.85 (br s, 2H), 3.78 (s, 3H), 2.90 (t, J=7.6 Hz, 2H), 2.44 (s, 3H), 1.14 (s, 9H); ¹³C NMR (101 MHz, CDCl₃) δ 159.64, 154.94, 145.70, 139.39, 131.10, 129.70, 129.49, 121.33, 114.48, 112.11, 83.12, 55.13, 53.89, 32.22, 27.48, 21.68. HRMS (ESI⁺) Calcd. for [C₂₁H₂₇NO₆S+Na]⁺ 444.1457, Found 444.1451.

Following the general intramolecular aza-annulation procedure, tert-butyl 3-methoxyphenethyl(tosyl)carbamate (10h: 51 mg, 0.12 mmol), TFA (18 µL, 0.24 mmol), and Du Bois' catalyst (1.8 mg, 2.5 µmol) were stirred at rt in TFE (1 mL) for 19 h. Chromatographic purification of the crude product afforded 5-methoxyindoline (11h: 10 mg, 56%) as a colorless oil whose spectral data were in agreement with literature values in Kulkarni, et al., 2011. TLC: R$_f$≈0.4 (30% EtOAc/hexanes); $^1$H NMR (400 MHz, CDCl$_3$) δ 6.74 (s, 1H), 6.60-6.55 (m, 2H), 3.73 (s, 3H), 3.52 (t, J=8.3 Hz, 2H), 2.99 (t, J=8.3 Hz, 2H).

FIG. 3: Entry 9

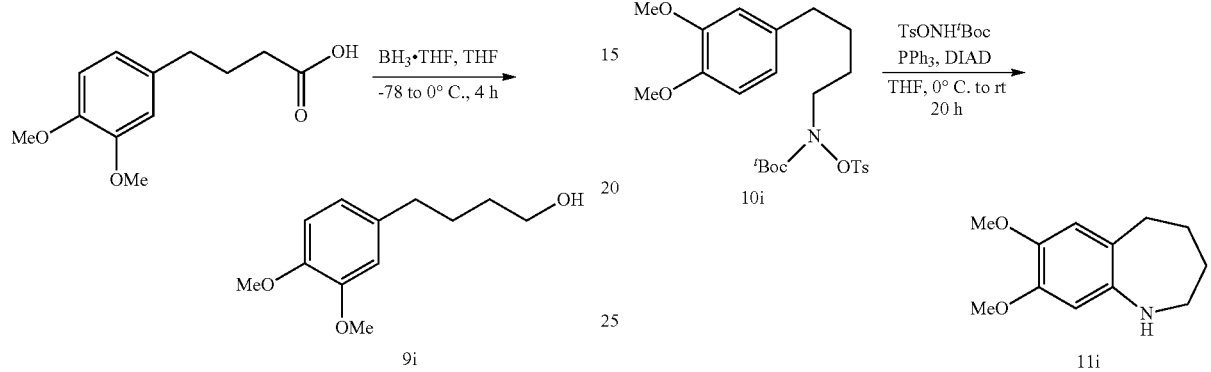

Following the acid reduction procedure as applied to 9b, 4-(3,4-dimethoxyphenyl)butanoic acid (1.12 g, 5.0 mmol) and BH$_3$·THF (1.0 M in THF, 6.0 mL, 6.0 mmol) were reacted in THF (15 mL) for 4 h. Chromatographic purification of the crude product afforded 4-(3,4-dimethoxyphenyl)butan-1-ol (9i: 0.925 g, 88%) as a colorless oil whose spectral data were concordant with literature values in Asiamah, et al., 2015. TLC: R$_f$≈0.3 (40% EtOAc/hexanes); $^1$H NMR (400 MHz, CDCl$_3$) δ 6.78 (d, J=8.7 Hz, 1H), 6.77-6.65 (m, 2H), 3.87 (s, 3H), 3.85 (s, 3H), 3.71-3.62 (m, 2H), 2.59 (t, J=7.4 Hz, 2H), 1.75-1.55 (m, 4H), 1.28 (br s, 1H); $^{13}$C NMR (101 MHz, CDCl$_3$) δ 148.74, 147.07, 134.97, 120.12, 111.65, 111.12, 62.83, 55.90, 55.78, 35.25, 32.33, 27.75.

Following the general Mitsunobu procedure, 4-(3,4-dimethoxyphenyl)butan-1-ol (9i: 0.152 g, 1.0 mmol), PPh$_3$ (0.315 g, 1.2 mmol), DIAD (0.24 mL, 1.2 mmol), and TsONH$^t$Boc (0.345 g, 1.2 mmol) were stirred in dry THF (5 mL) for 19 h. Chromatographic purification of the crude product afforded tert-butyl (4-(3,4-dimethoxyphenyl)butyl)(tosyloxy)carbamate (10i: 0.386 g, 80%) as a colorless solid, mp 88.1° C. TLC: R$_f$≈0.5 (30% EtOAc/hexanes); $^1$H NMR (400 MHz, CDCl$_3$) δ 7.85 (d, J=8.3 Hz, 2H), 7.34 (d, J=8.3 Hz, 2H), 6.78 (d, J=8.6 Hz, 1H), 6.75-6.65 (m, 2H), 3.86 (s, 3H), 3.84 (s, 3H), 3.65 (br s, 2H), 2.55 (t, J=7.5 Hz, 2H), 2.44 (s, 3H), 1.72-1.50 (m, 4H), 1.18 (s, 9H); $^{13}$C NMR (101 MHz, CDCl$_3$) δ 155.45, 148.74, 147.09, 145.65, 134.64, 131.17, 129.68, 129.49, 120.11, 111.61, 111.14, 83.11, 55.90, 55.77, 52.65, 34.99, 28.57, 27.55, 25.38, 21.69. HRMS (ESI$^+$) Calcd. for [C$_{24}$H$_{33}$NO$_7$S+Na]$^+$ 502.1875, Found 502.1880.

Following the general intramolecular aza-annulation, tert-butyl (4-(3,4-dimethoxyphenyl)butyl)(tosyloxy)carbamate (10i: 96 mg, 0.2 mmol), TFA (31 µL, 0.4 mmol), and Du Bois' catalyst (3.0 mg, 4.0 µmol) were stirred at rt in TFE (2 mL) for 20 h. Chromatographic purification of the crude product afforded 7,8-dimethoxy-2,3,4,5-tetrahydro-1H-benzo[b]azepine (11i: 28 mg, 68%) whose spectral data were in agreement with literature values in Fan, et al., 2011. TLC: R$_f$≈0.3 (50% EtOAc/hexanes); $^1$H NMR (400 MHz, CDCl$_3$) δ 6.65 (s, 1H), 6.33 (s, 1H), 3.82 (s, 3H), 3.81 (s, 3H), 3.08-2.94 (m, 2H), 2.77-2.59 (m, 2H), 1.82-1.73 (m, 2H), 1.64-1.56 (m, 2H); $^{13}$C NMR (101 MHz, CDCl$_3$) δ 147.08, 143.74, 143.01, 125.64, 114.74, 104.40, 56.37, 55.95, 49.26, 35.59, 32.28, 27.20.

FIG. 5

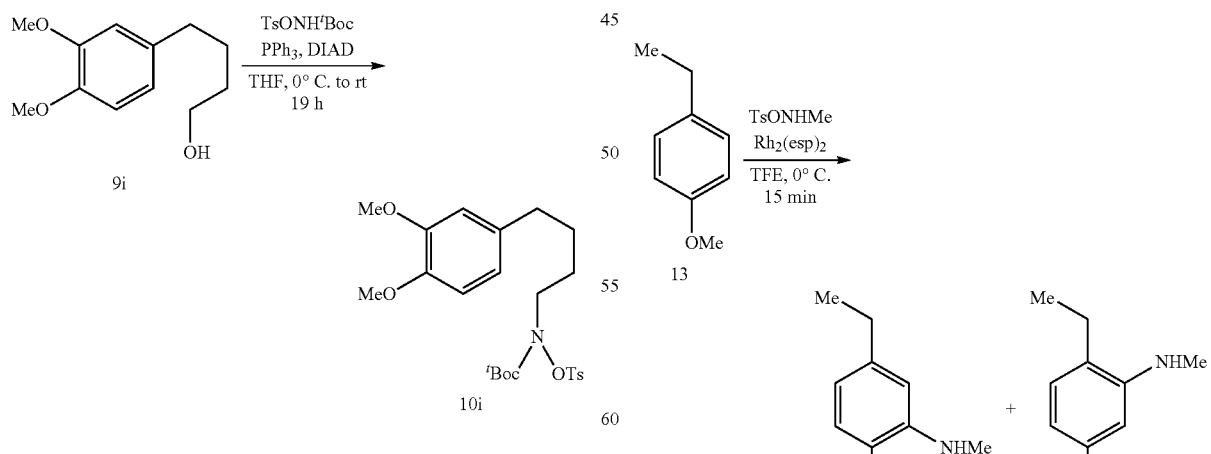

67%, 3.6:1

Following the general intermolecular amination procedure, 4-ethylanisole (13: 68 mg, 0.5 mmol), Du Bois' catalyst (7.6 mg, 0.01 mmol), and TsONHMe (0.151 g, 0.75 mmol) were stirred at 0° C. in TFE (5 mL) for 15 min. Chromatographic purification of the crude product afforded 15 (43 mg) and 16 (12 mg) (55 mg total, 67% combined yield) as oils.

5-ethyl-2-methoxy-N-methylaniline (15)

TLC: $R_f$=0.6 (30% EtOAc/hexanes); $^1$H NMR (400 MHz, CDCl$_3$) δ 6.72 (dd, J=8.0, 1.9 Hz, 1H), 6.59-6.44 (m, 2H), 4.25 (br s, 1H), 3.85 (s, 3H), 2.90 (s, 3H), 2.62 (q, J=7.6 Hz, 2H), 1.27 (t, J=7.6 Hz, 3H); $^{13}$C NMR (101 MHz, CDCl$_3$) δ 145.11, 139.18, 137.33, 115.05, 109.34, 109.20, 55.55, 30.44, 28.71, 16.04. HRMS (ESI$^+$) Calcd. for [C$_{10}$H$_{15}$NO+H]$^+$166.1232, Found 166.1233.

2-ethyl-5-methoxy-N-methylaniline (16)

TLC: $R_f$=0.4 (30% EtOAc/hexanes); $^1$H NMR (400 MHz, CDCl$_3$) δ 6.81-6.69 (m, 2H), 6.59 (d, J=9.4 Hz, 1H), 3.77 (s, 3H), 2.86 (s, 3H), 2.48 (q, J=7.5 Hz, 2H), 1.25 (t, J=7.5 Hz, 3H); $^{13}$C NMR (101 MHz, CDCl$_3$) δ 151.91, 140.94, 129.64, 114.99, 111.06, 110.57, 55.79, 31.63, 23.86, 12.88. HRMS (ESI$^+$) Calcd. for [C$_{10}$H$_{16}$NO+H]$^+$166.1232, Found 166.1237.

Control Experiments

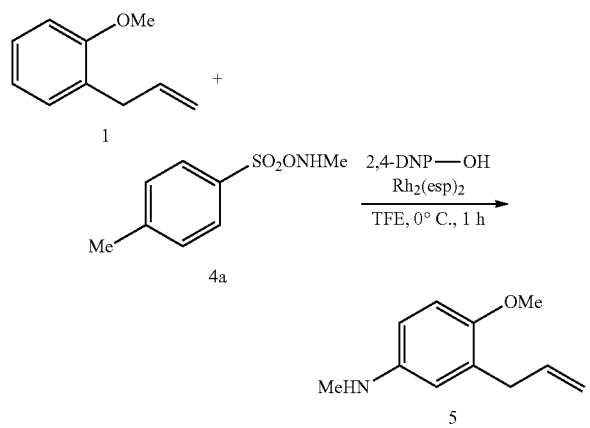

Du Bois' catalyst (7.6 mg, 0.01 mmol), 2,4-DNP—OH (0.138 g, 0.75 mmol), and aminating agent (4a: 0.151 g, 0.75 mmol) were added to a stirring 0° C. solution of 2-allylanisole (1: 74 mg, 0.5 mmol) in TFE (5 mL). After 1 h, the reaction was worked up following the general intermolecular amination procedure (vide supra). Chromatographic purification of the crude product afforded 3-allyl-4-methoxy-N-methylaniline (5: 47 mg, 53%) as an oil whose spectral characteristics were concordant with values described above (FIG. 1, Right Panel).

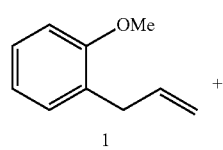

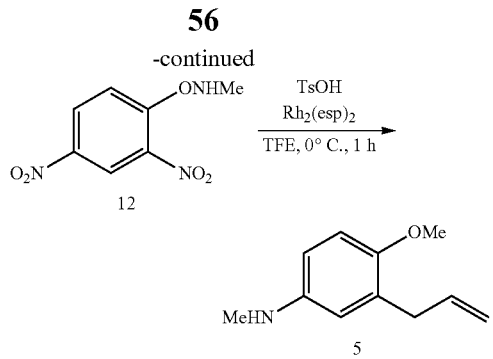

Du Bois' catalyst (7.6 mg, 0.01 mmol), p-toluene sulfonic acid (TsOH: 0.143 g, 0.75 mmol), and aminating agent (12: 0.160 g, 0.75 mmol) were added to a stirring 0° C. solution of 2-allylanisole (1: 74 mg, 0.5 mmol) in TFE (5 mL). After 1 h, the reaction was worked up following the general intermolecular amination procedure (vide supra). Chromatographic purification of the crude product afforded 3-allyl-4-methoxy-N-methylaniline (5: 37 mg, 42%) as an oil whose spectral characteristics were concordant with values described above (FIG. 1, Right Panel).

C. Catalyst Screening: Initial Catalyst Screen

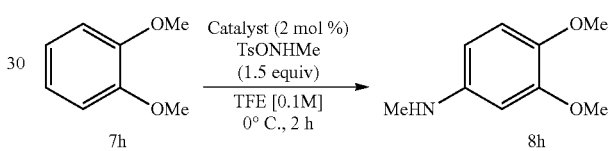

Under standardized reaction conditions, yields of 55% of amine 8h from 7h were realized using: CuCl, CuOAc, CuCl$_2$, CuI, CuTC, Cu(OAc)$_2$, CoBr$_2$, 1,2-bis(diphenylphosphino)ethane]dichloronickel(II), NiCl$_2$(PPh$_3$)$_2$, (R,R)-(−)-N,N'-bis(3,5-di-tert-butylsalicylidene)-1,2-cyclohexanediaminocobalt(II), Fe(II)CO$_2$Cy$_2$, Fe(acac)$_3$, (1,5-cyclooctadiene)bis(methyldiphenylphosphine)iridium(I) hexafluorophosphate, and Bis(1,5-cyclooctadiene)diiridium (I) dichloride.

Catalyst Screening: Rh Catalyst Screen

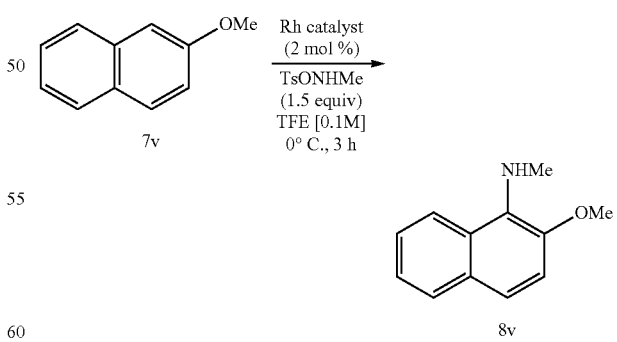

Under standardized reaction conditions, yields of 40-50% of amine 8v from 7v were realized using: chloro(1,5-hexadiene)rhodium(I) dimer, rhodium(III) acetylacetonate, and dirhodium(II)tetrakis[methyl 2-oxazolidone-4(S)-carboxylate]acetonitrile complex (Doyle catalyst).

Example 5—Reaction Conditions, Isotope Studies, and Chiral Selectivity

A. Reaction Conditions

TABLE 1

Reaction Optimization Studies 7h (1,2-dimethoxybenzene) + Rh-catalyst (2 mol %), TsONHMe (1.5 equiv), TFE [0.1 M] → 8h (4-methoxy-3-methoxy-N-methylaniline)

| Entry | Catalyst | Temperature (° C.) | Time (h) | Solvent | Yield (%) |
|---|---|---|---|---|---|
| 1 | Rh$_2$(esp)$_2$ | 0 | 1 | TFE | 62 |
| 2 | Rh$_2$(esp)$_2$ | −20 | 24 | TFE | 48 |
| 3 | Rh$_2$(esp)$_2$ | 0 | 1 | CH$_3$CN | 0 |
| 4 | Rh$_2$(esp)$_2$ | 0 | 1 | CH$_2$Cl$_2$ | 0 |
| 5 | Rh$_2$(esp)$_2$ | 0 | 1 | THF | 0 |
| 6 | Rh$_2$(esp)$_2$ | 0 | 1 | Toluene | 0 |
| 7 | Rh$_2$(esp)$_2$ | 0 | 1 | Dioxane | 0 |
| 8 | Rh$_2$(esp)$_2$ | 0 | 1 | MeOH | 10-20 |
| 9 | Rh$_2$(esp)$_2$ | 0 | 1 | EtOH | 10-20 |
| 10 | Rh$_2$(OAc)$_4$ | 0 | 1 | TFE | 46 |
| 11 | Rh$_2$(n-octanoate)$_4$ | 0 | 1 | TFE | 41 |
| 12 | Rh$_2$(TFA)$_4$ | 0 | 1 | TFE | 10-20 |
| 13 | Rh$_2$(heptafluorobutyrate)$_4$ | 0 | 1 | TFE | 10-20 |
| 14 | Rh$_2$(esp)$_2$ | 0 | 1 | TFE (1 equiv TFA) | 50 |
| 15 | Rh$_2$(esp)$_2$ | 0 | 1 | TFE (1 equiv K$_2$CO$_3$) | <10% |
| 16 | Rh$_2$(esp)$_2$ | 0 | 2 | TFE:AcOH (4:1); quench with Na$_2$CO$_3$ to pH 9 | 69 |
| 17 | Rh$_2$(esp)$_2$ | 0 | 2 | TFE:AcOH (4:1); quench with NaOH to pH 9 | 64 |
| 18 | Rh$_2$(esp)$_2$ | 0 | 0.5 | TFE:AcOH (4:1) | 75 |

B. Chiral Separations

Figure 6:
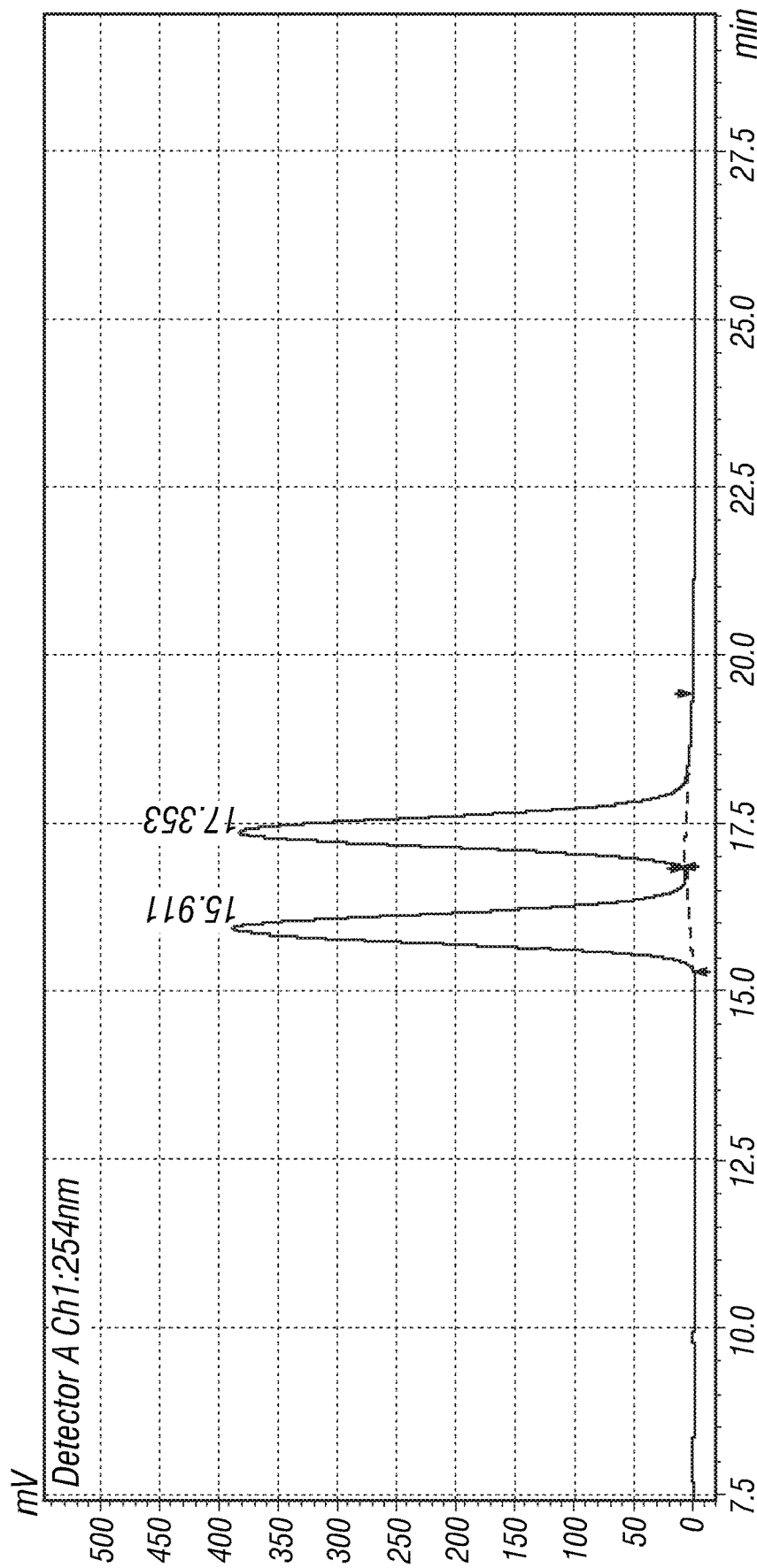
FIG. 6 shows the chiral HPLC trace of 11e.

Chiralcel® OJ-H, n-hexane/i-PrOH=95/5, 254 nm detection, flow rate=0.8 mL/min, R$_t$ (S-isomer)=15.9 min, R$_t$ (R-isomer)=17.3 min. See FIG. 6.

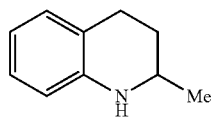

11e

TABLE 2

| Chiral HPLC analysis of 11e | | | | |
|---|---|---|---|---|
| Peak # | Ret. Time | Area | Height | Area % |
| 1 | 15.911 | 11658624 | 386321 | 50.2186 |
| 2 | 17.353 | 11557128 | 376406 | 49.7814 |

Figure 7:
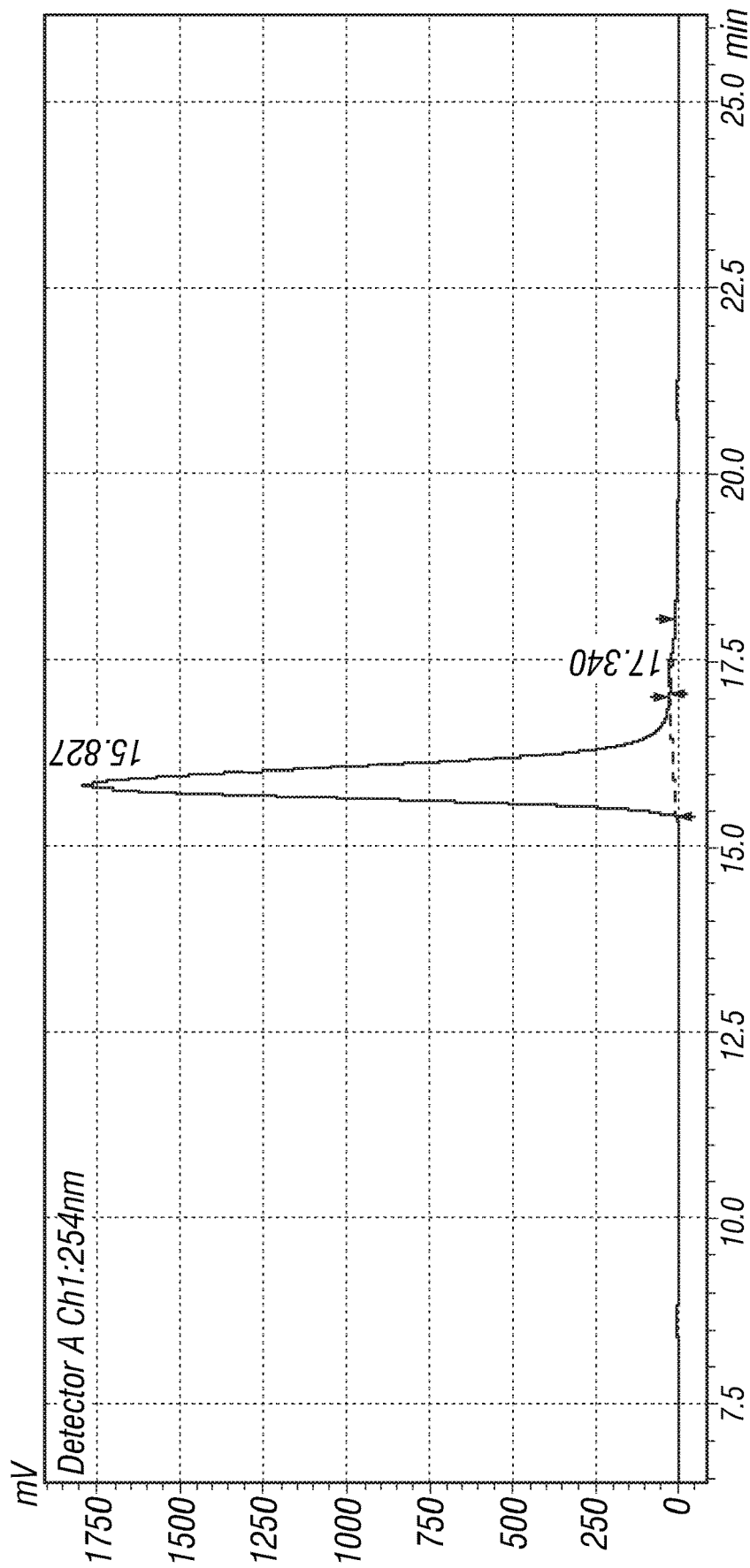
FIG. 7 shows the chiral HPLC trace of 11f.

Chiralcel® OJ-H, n-hexanes/i-PrOH=95/5, 254 nm detector, flow rate=0.8 mL/min, R$_t$ (S-isomer)=15.8 min, R$_t$ (R-isomer)=17.3 min. See FIG. 7.

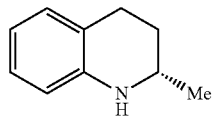

TABLE 3

| Chiral HPLC analysis of 11f | | | | |
|---|---|---|---|---|
| Peak # | Ret. Time | Area | Height | Area % |
| 1 | 15.827 | 52052475 | 1779241 | 99.7212 |
| 2 | 17.340 | 145552 | 6488 | 0.2788 |

C. HPLC Sensitivity Test

Figure 8:
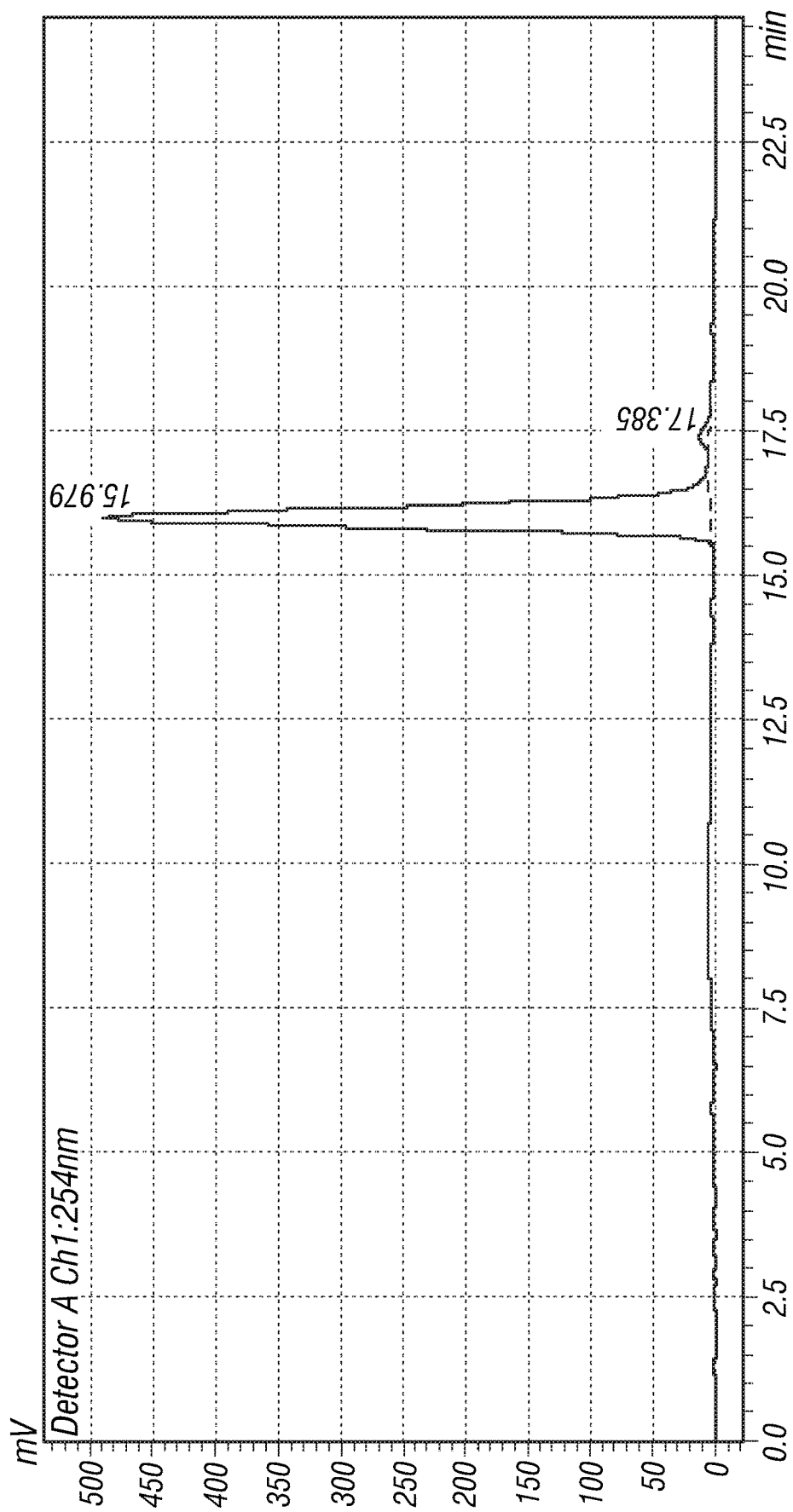
FIG. 8 shows the chiral HPLC trace of 11f doped with 11e.
Figure 9A:
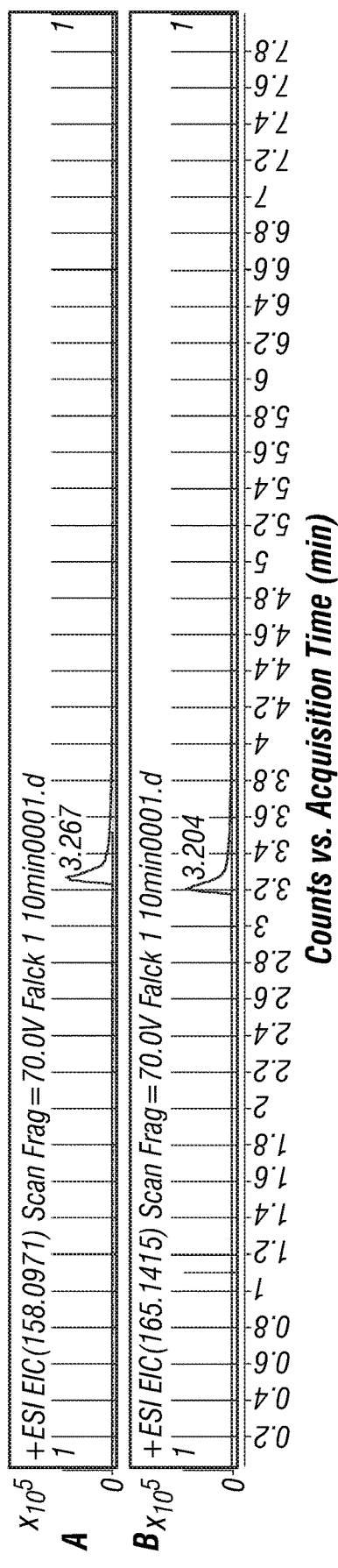
FIGS. 9A-9D shows the ESI-LC/MS (M+1)$^+$ using Single Ion Monitoring chromatograms for the deuterium isotope studies for 10 minutes (FIG. 9A), 20 minutes (FIG. 9B), 30 minutes (FIG. 9C), or 40 minutes (FIG. 9D).
Figure 9B:
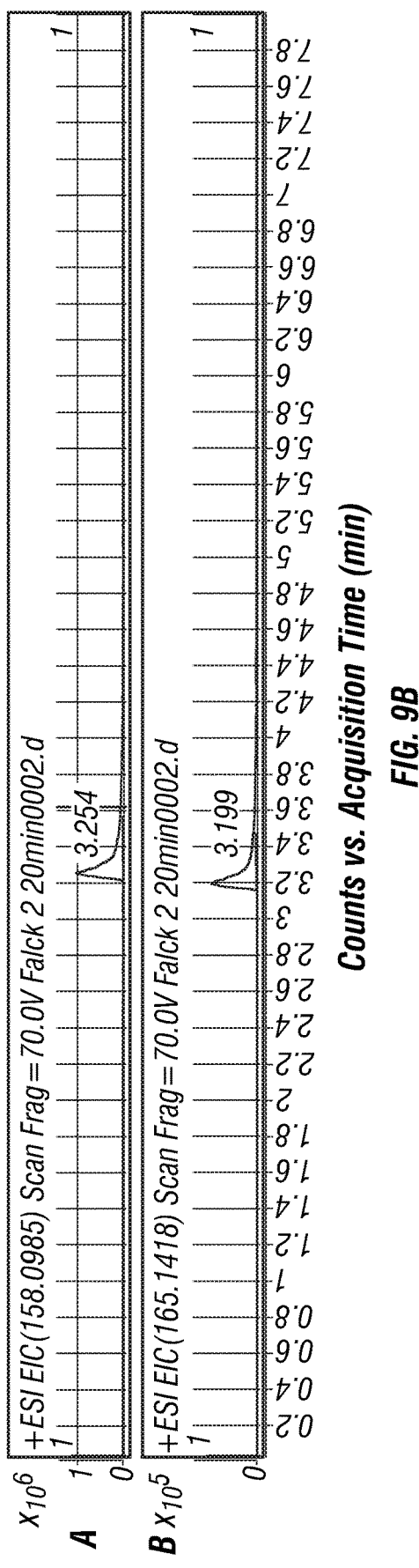
Figure 9C:
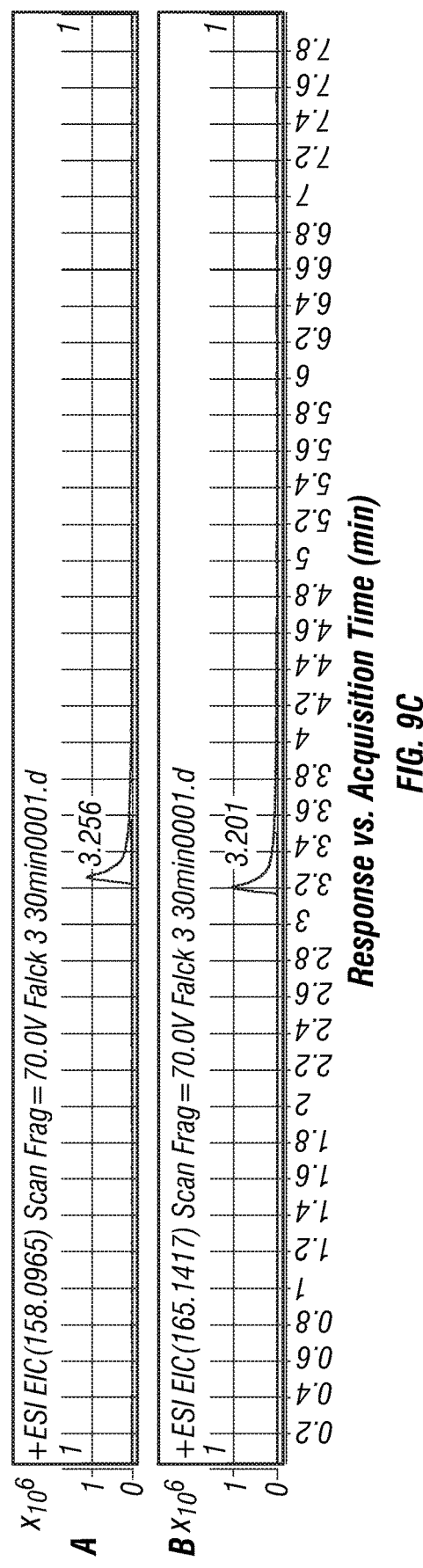
Figure 9D:
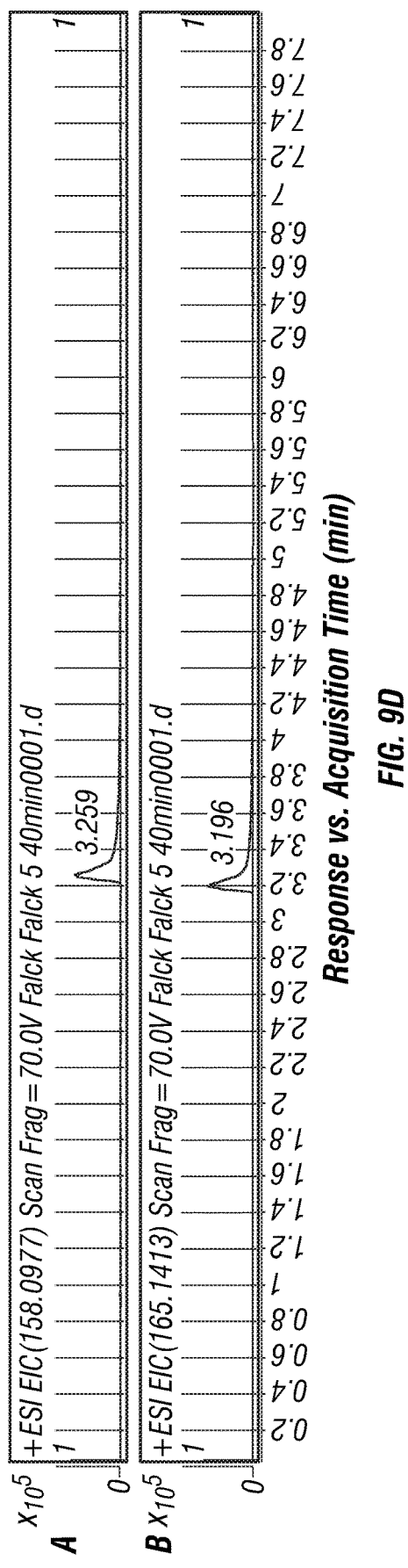

Sample of 11f spiked plus 2% of 11e analyzed using a Chiralcel® OJ-H column, n-hexanes/i-PrOH (95/5) eluent, 254 nm detection, flow rate=0.8 mL/min, R$_t$ (S-isomer)=15.9 min, R$_t$ (R-isomer)=17.3 min. See FIG. 8.

TABLE 4

| Chiral HPLC Results of 11f spiked with 11e | | | | |
|---|---|---|---|---|
| Peak # | Ret. Time | Area | Height | Area % |
| 1 | 15.979 | 12013565 | 487307 | 98.7925 |
| 2 | 17.385 | 146832 | 6904 | 1.2075 |

An equimolar mixture of naphthalene (7t) and naphthalene-d8 (7t-d) were treated with TsONHMe (0.5 equiv) and Rh2(esp)2 (2 mol %) as described in the General Intermolecular Amination procedure. Aliquots were removed at 10, 20, 30, and 40 min intervals and the ratio of amination products analyzed by ESI-LC/MS. The uncorrected integrated areas are approximately 1:1 in all cases.

D. Kinetic Isotope Studies

ESI-LC/MS conditions: 5% CH$_3$CN/H$_2$O to 100% CH$_3$CN, Flow rate: 0.5 mL/min, Injection volume=1 μL, UV detection: 254 nm HRMS (ESI$^+$): 8t Calcd. [C$_{11}$H$_{11}$N+H]$^+$ 158.0970, 8t-ds. Calcd. [C$_{11}$H$_4$D$_7$N+H]$^+$ 165.1409. See FIGS. 9A-9D.

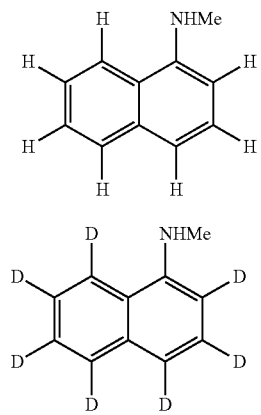

Example 6—Formation of N-Heterocycloalkyl Group

A. General Mitsunobu Procedure

Diisopropyl azodicarboxylate (DIAD: 1.2 equiv) was added to a stirring, 0° C. solution of triphenylphosphine (1.2 equiv) in dry THF under an argon atmosphere. A white precipitate developed after stirring for about 10 min. After 30 min total, a solution of alcohol (1.0 equiv) in dry THF and tert-butyl tosyloxycarbamate (TsONHBoc: 1.2 equiv) were added successively. The ice bath was removed after 1 h and the reaction mixture was stirred for 2-10 h. The volatiles were then removed in vacuo and, unless otherwise stated, the residue was purified with a pre-packed SiO$_2$ column on a medium pressure, automated chromatograph using EtOAc/hexanes as eluent to furnish the $^t$Boc-amino adduct.

B. General Insertion Procedure

To a stirring, 0° C. solution of $^t$Boc-protected amino adduct (1.0 equiv) in 2,2,2-trifluoroethanol were added sequentially trifluoroacetic acid (TFA, 2.0 equiv) and Rh$_2$(esp)$_2$ (2 mol %). After stirring for 2 h, the cold bath was removed and the stirring was continued for an additional 20-22 h. The reaction mixture was diluted with CH$_2$Cl$_2$ and washed successively with saturated aqueous Na$_2$CO$_3$ and brine. The organic layer was dried over anhydrous Na$_2$SO$_4$ and concentrated in vacuo. The crude product was purified with a pre-packed SiO$_2$ column on a medium pressure, automated chromatograph using methanol/dichloromethane with 1% $^t$BuNH$_2$ as eluent to furnish an N-heterocycle.

Some non-limiting examples of these methods are described below.

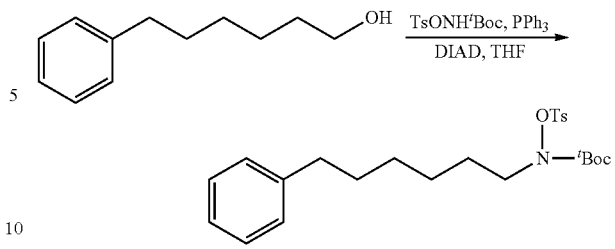

Following the general Mitsunobu procedure, 6-phenylpropan-1-ol (Aldrich Chem. Com., 0.56 mL, 3.0 mmol), PPh$_3$ (0.866 g, 3.3 mmol), DIAD (0.65 mL, 3.3 mmol), and TsONHBoc (0.948 g, 3.3 mmol) were stirred at rt in dry THF (9 mL) for 4 h. Chromatographic purification of the crude product afforded tert-butyl (6-phenylhexyl)(tosyloxy)carbamate (1.24 g, 92%) as a colorless, viscous oil. R$_f$=0.7 (30% EtOAc:hexanes); $^1$H NMR (400 MHz, CDCl$_3$) δ 7.85 (d, J=8.3 Hz, 2H), 7.34 (d, J=8.3 Hz, 2H), 7.30-7.24 (m, 2H), 7.20-7.14 (m, Hz, 3H), 3.60 (app br s, 2H), 2.59 (t, J=8.0 Hz, 2H), 2.45 (s, 3H), 1.67-1.55 (m, 4H), 1.39-1.23 (m, 4H), 1.21 (s, 9H).

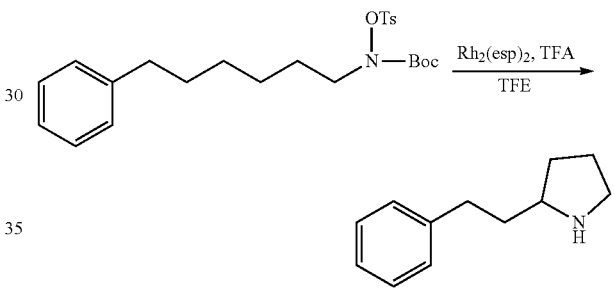

Following the general insertion procedure, tert-butyl (6-phenylhexyl)(tosyloxy)carbamate (0.448 g, 1.0 mmol), TFA (153 μL, 2.0 mmol), and Du Bois' catalyst (15.2 mg, 0.02 mmol) were stirred at rt in TFE (10 mL) for 21 h. Chromatographic purification of the crude product afforded 2-phenethylpyrrolidine (117 mg, 67%) as an oil. R$_f$=0.3 (5% MeOH/DCM with 3% $^t$BuNH$_2$); $^1$H NMR (400 MHz, CDCl$_3$) δ 7.32-7.24 (m, 2H), 7.24-7.12 (m, 3H), 3.07-2.91 (m, 2H), 2.88-2.79 (m, 1H), 2.77-2.61 (m, 2H), 1.96-1.64 (m, 5H), 1.34-1.23 (m, 1H); $^{13}$C NMR (101 MHz, CDCl$_3$) δ 142.33, 128.33, 128.31, 125.70, 58.79, 46.62, 38.21, 33.87, 31.82, 25.40. Characterization data corresponds to reported data from Secor and Seeman, 1986.

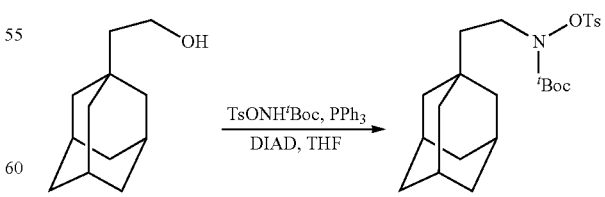

Following the general Mitsunobu procedure, 2-((3r,5r,7r)-adamantan-1-yl)ethan-1-ol (Aldrich Chem. Com., 0.361g, 2.0 mmol), PPh$_3$ (0.577 g, 2.2 mmol), DIAD (0.44 mL, 2.2 mmol), and TsONH$^t$Boc (0.632 g, 2.2 mmol) were stirred at rt in dry THF (6 mL) for 3 h. Chromatographic purification of the crude product afforded tert-butyl (2-((3r,5r,7r)-adamantan-1-yl)ethyl)(tosyloxy)carbamate (0.826 g, 92%) as a colorless, viscous oil. $R_f$=0.7 (20% EtOAc:hexanes); $^1$H NMR (400 MHz, CDCl$_3$) δ 7.85 (d, J=8.3 Hz, 2H), 7.34 (d, J=8.2 Hz, 2H), 3.61 (app br s, 2H), 2.45 (s, 3H), 1.93 (app br s, 3H), 1.73-1.64 (m, 3H), 1.65-1.56 (m, 3H), 1.49-1.40 (m, 6H), 1.23 (s, 9H).

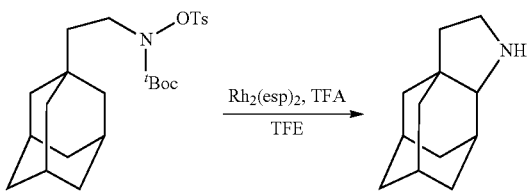

Following the general insertion procedure, tert-butyl (2-((3r,5r,7r)-adamantan-1-yl)ethyl)(tosyloxy)carbamate (0.225 g, 0.5 mmol), TFA (77 µL, 1.0 mmol), and Du Bois' catalyst (7.6 mg, 0.01 mmol) were stirred at rt in TFE (5 mL) for 23 h. Chromatographic purification of the crude product afforded (3ar,5R,7S,9s)-decahydro-3a,7:5,9-dimethanocycloocta[b]pyrrole (68 mg, 77%) as an oil. $R_f$=0.3 (5% MeOH/DCM with 1% $^t$BuNH$_2$); $^1$H NMR (400 MHz, CDCl$_3$) δ 3.07 (dt, J=11.3, 8.3 Hz, 1H), 2.95 (td, J=10.8, 3.0 Hz, 1H), 2.60 (d, J=2.7 Hz, 1H), 2.44 (br s, 1H), 2.09 (d, J=3.1 Hz, 1H), 1.99-1.86 (m, 2H), 1.85-1.75 (m, 3H), 1.70-1.60 (m, 4H), 1.57-1.50 (m, 1H), 1.49-1.38 (m, 2H), 1.37-1.29 (m, 1H), 1.28-1.21 (m, 1H); $^{13}$C NMR (101 MHz, CDCl$_3$) δ 67.60, 42.98, 41.79. 39.22, 38.11, 37.66, 37.47, 36.77, 30.53, 29.98, 29.33, 28.22. Characterization data corresponds to reported data from Zoidis, et al., 2008.

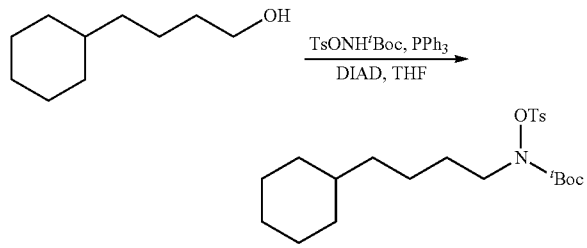

Following the general Mitsunobu procedure, 4-cyclohexylbutan-1-ol (0.469 g, 3.0 mmol), PPh$_3$ (0.866 g, 3.3 mmol), DIAD (0.65 mL, 3.3 mmol), and TsONHBoc (0.958 g, 3.3 mmol) were stirred at rt in dry THF (9 mL) for 5 h. Chromatographic purification of the crude product afforded tert-butyl (4-cyclohexylbutyl)(tosyloxy)carbamate (1.09 g, 85%) as a colorless, viscous oil. $R_f$=0.7 (20% EtOAc: hexanes); 1H NMR (400 MHz, CDCl$_3$) δ 7.86 (d, J=8.3 Hz, 2H), 7.34 (d, J=8.6 Hz, 2H), 3.59 (app br s, 2H), 2.45 (s, 3H), 1.71-1.55 (m, 6H), 1.22 (s, 9H), 1.30-1.09 (m, 9H), 093-0.77 (m, 2H).

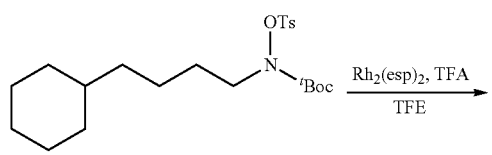

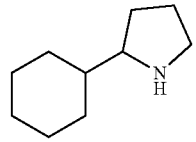

Following the general insertion procedure, tert-butyl (4-cyclohexylbutyl)(tosyloxy)carbamate (0.213 g, 0.5 mmol), TFA (77 µL, 1.0 mmol), and Du Bois' catalyst (7.6 mg, 0.01 mmol) were stirred at rt in TFE (5 mL) for 22 h. Chromatographic purification of the crude product afforded 2-cyclohexylpyrrolidine (50 mg, 65%) as an oil. $R_f$=0.3 (10% MeOH/DCM with 1% $^t$BuNH$_2$); $^1$H NMR (400 MHz, CDCl$_3$) δ 3.02-2.93 (m, 1H), 2.78 (dt, J=10.2, 7.3 Hz, 1H), 2.60 (app q, J=8.6 Hz, 1H), 1.96-1.76 (m, 3H), 1.75-1.56 (m, 5H), 1.52-1.35 (m, 1H), 1.33-1.07 (m, 5H), 1.01-0.86 (m, 2H); $^{13}$C NMR (101 MHz, CDCl$_3$) δ 64.76, 46.52, 43.88, 31.12, 30.48, 29.64, 26.53, 26.18, 26.07, 25.20.

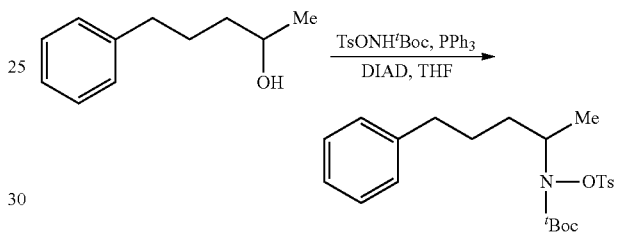

Following the general Mitsunobu procedure, 5-phenylpentan-2-ol (0.2 g, 1.218 mmol), PPh$_3$ (0.48 g, 1.826 mmol), DIAD (0.36 mL, 1.826 mmol), and TsONHBoc (0.524 g, 1.826 mmol) were stirred at rt in dry THF (15 mL) for 12 h. Chromatographic purification of the crude product afforded tert-butyl (5-phenylpentan-2-yl)(tosyloxy)carbamate (0.43 g, 82%) as a colorless, viscous oil. $R_f$=0.6 (20% EtOAc: hexanes); $^1$H NMR (400 MHz, CDCl$_3$) δ 7.85 (d, J=8.3 Hz, 2H), 7.32 (d, J=8.0 Hz, 2H), 7.29-7.25 (m, 3H), 7.20-7.15 (m, 2H), 4.01-3.91 (m, 1H), 2.60 (t, J=7.6 Hz, 2H), 2.44 (s, 3H), 1.82-1.73 (m, 1H), 1.69-1.59 (m, 2H), 1.53-1.45 (m, 1H), 1.25 (s, 9H), 1.19 (d, J=6.8 Hz, 3H).

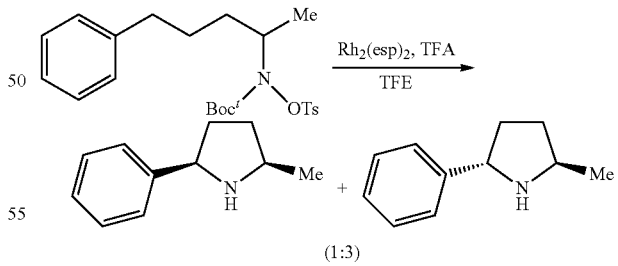

Following the general insertion procedure, tert-butyl (5-phenylpentan-2-yl)(tosyloxy)carbamate (0.1 g, 0.23 mmol), TFA (35 µL, 0.46 mmol), and Du Bois' catalyst (3.5 mg, 4.6 µmol) were stirred at rt in TFE (2 mL) for 21 h. Chromatographic purification of the crude product afforded a mixture of cis- and trans-2-methyl-5-phenylpyrrolidine (1:3, 30 mg, 81%) as an oil. $R_f$=0.5 (10% MeOH/DCM); $^1$H NMR (400 MHz, CDCl$_3$) δ 7.34-7.10 (m, 6H, cis and trans), 4.30 (t, J=7.7 Hz, 1H, trans), 4.09 (t, J=8.0 Hz, 0.3H, cis), 3.53-3.41 (m, 1H, trans), 3.29-3.19 (0.4H, cis), 2.78 (bs, 1.8H, cis and trans), 2.26-2.17 (m, 1.09H, cis and trans), 2.14-1.99 (m, 1.4H, cis and trans), 1.96-1.86 (m, 0.4H, cis and trans), 1.79-1.65 (m, 1.4H, cis and trans), 1.45-1.34 (m, 1.45H, cis and trans), 1.17 (d, J=13.7 Hz, 1H, cis), 1.14 (d, J=13.7 Hz, 2.8H, trans); $^{13}$C NMR (101 MHz, CDCl$_3$) δ 144.78, 144.22, 128.38, 128.29, 126.81, 126.79, 126.63, 126.42, 62.95, 61.57, 54.8, 54.26, 35.19, 34.6, 33.92, 33.4, 21.84, 21.39. Characterization data corresponds to reported data from O'Reilly, et al., 2014.

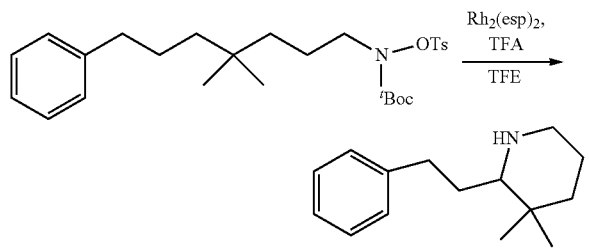

Following the general insertion procedure, tert-butyl (4,4-dimethyl-7-phenylheptyl)(tosyloxy)carbamate (0.2 g, 0.408 mmol), TFA (62 μL, 0.81 mmol), and Du Bois' catalyst (6.1 mg, 8.1 μmol) were stirred at rt in TFE (2 mL) for 19 h. Chromatographic purification of the crude product afforded 3,3-dimethyl-2-phenethylpiperidine (40 mg, 46%) as an oil. R$_f$=0.5 (15% MeOH/DCM); $^1$H NMR (400 MHz, CDCl$_3$) δ 7.42-7.07 (m, 5H), 3.19-3.11 (m, 1H), 2.92-2.82 (m, 1H), 2.63-2.53 (m, 2H), 2.31 (d, J=10 Hz, 1H), 1.91-1.81 (m, 1H), 1.72-1.58 (m, 1H), 1.51-1.39 (m, 3H), 1.31-1.20 (m, 2H), 0.90 (s, 3H), 0.84 (s, 3H); $^{13}$C NMR (101 MHz, CDCl$_3$) δ 142.32, 128.41, 128.35, 125.78, 64.96, 47.06, 40.0, 33.62, 32.84, 32.12, 28.79, 22.70, 19.14.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Angelici, Reagents for Transition Metal Complex and Organometallic Synthesis., Wiley-Interscience, New York, vol. 28, 1990.
Asiamah, et al., Bioorg. Med. Chem., 23:7007-7014, 2015.
Brasche and Buchwald, Angew. Chem., Int. Ed. 47:1932-1934, 2008.
Candeias et al., Chem. Rev. 109, 2703-2802, 2009.
Carpino, J. Am. Chem. Soc. 82:3133-3135, 1960.
Chen, et al., J. Am. Chem. Soc., 137:11718-11724, 2015.
Chen et al., Org. Chem. Front. 2, 1107-1295, 2015.
Cooke, et al., J. Org. Chem., 52:1381-1396, 1987.
Dalla Cort et al., J. Org. Chem. 70, 8877-8883, 2005.
Daskapan, ARKIVOC 230-262, 2011.
Davies and Dai, Organomet. Chem. III., vol. 10, pp. 167-212, 2007. de Haan, et al., J. Photochem. Photobiol. A: Chem., 102:179-188, 1997.
Dugar, et al., Synthesis, 47:712-720, 2015.
Espino et al., J. Am. Chem. Soc. 126:15378-15379, 2004.
Fan, et al., Bioorg. Med. Chem., 19:1852-1859, 2011.
Gómez, et al., Tetrahedron, 62:9832-9839, 2006.
Hartwig et al., Chem. Anilines 1, 455-536, 2007.
Hartwig, Acc. Chem. Res. 41:1534-1544, 2008.
Hili and Yudin, Nat. Chem. Biol., 2:284-287, 2006.
Inamoto et al., J. Org. Chem. 75:3900-3903, 2010.
Inamoto et al., Org. Lett. 9:2931-2934, 2007.
Jat et al., Science 343:61-65, 2014.
John et al., Org. Lett. 9:4009-4012, 2007.
Jones, Acc. Chem. Res. 36:140-146, 2003.
Kulkarni, et al., Org. Lett., 13:5124-5127, 2011.
Kung and Falvey, J. Org. Chem., 70:3127-3132, 2005.
Kunz et al., Synlett, 2428-2439, 2003.
Lundgren and Stradiotto, Aldrichimica Acta 45:59-65, 2012.
Maejima et al., Tetrahedron 68:1712-1722, 2012.
Manas and Smith, Tetrahedron, 43:1847-1856, 1987.
Mendiola et al., Org. Process Res. Dev. 13:263-267, 2009.
O'Reilly, et al., Angew. Chem. Int. Ed., 53:2447-2450, 2014.
Ortiz-Marciales, et al., J. Org. Chem., 70:10132-10134, 2005.
Park et al., J. Am. Chem. Soc. 137:4534-4542, 2015.
Ricci, Amino Group Chemistry: From Synthesis to the Life Sciences., Wiley-VCH, pp. 394, 2008.
Romero et al., Science 349:1326-1330, 2015.
Secor and Seeman, Heterocycle, 24:1687-1698, 1986.
Shin et al., Acc. Chem. Res. 48:1040-1052, 2015.
Shrestha et al., J. Am. Chem. Soc. 135:8480-8483, 2013.
Simmons and Hartwig, Angew. Chem. Int. Ed. 51:3066-3072, 2012.
Sridharan, et al., Tetrahedron, 63:673-681, 2007.
Starkov et al., Chem.—Eur. J. 21:5278-5300, 2015.
Sun and Gu, Org. Lett. 17:2222-2225, 2015.
Surry and Buchwald, Angew. Chem., Int. Ed. 47:6338-6361, 2008.
Suzuki et al., Org. Lett. 17:1597-1600, 2015.
Takamatsu et al., J. Org. Chem. 80:3242-3249, 2015.
Takemoto and Miyabe, Organomet. Chem. III., vol. 10, pp. 695-724, 2007.
Tsang et al., J. Am. Chem. Soc. 127:14560-14561, 2005.
Wang, et al., J. Am. Chem. Soc., 125:10536-10537, 2003.
Xia and Taillefer, Angew. Chem., Int. Ed. 48:337-339, 2009.
Xie et al., Tetrahedron Lett. 54:5151-5154, 2013.
Xue et al., Eur. J. Org. Chem. 2014, 7481-7488, 2014.
Yang, Synlett 25:1186-1187, 2014.
Yu, et al., Tetrahedron Lett. 54:3167-3170, 2013.
Zeng et al., Org. Biomol. Chem. 9:8224-8227, 2011.
Zoidis, et al., Org. Biomol. Chem., 6:3177-3185, 2008.

What is claimed is:
1. A method of preparing a N-heterocycloalkane group comprising:
 (A) reacting a reactant compound, wherein the reactant compound contains a reactive functional group attached to an aliphatic linker and a second aliphatic or aromatic group and comprises 3 carbon atoms to 30 carbon atoms; with an aminating agent of the formula:

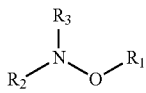

(I)

wherein:
R$_1$ is an arylsulfonyl$_{(C \leq 18)}$ or substituted arylsulfonyl$_{(C \leq 18)}$;
R$_2$ is hydrogen, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, alkynyl$_{(C \leq 12)}$, substituted alkynyl$_{(C \leq 12)}$, aryl$_{(C \leq 12)}$, substituted aryl$_{(C \leq 12)}$, aralkyl$_{(C \leq 12)}$, substituted aralkyl$_{(C \leq 12)}$, or a monovalent amino protecting group; and
R$_3$ is hydrogen, a monovalent amino protecting group; and
under conditions sufficient to displace the reactive functional group to obtain an aminating compound with the group:

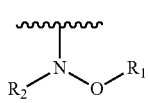

(III)

wherein:
R$_1$ is an arylsulfonyl$_{(C \leq 18)}$ or substituted arylsulfonyl$_{(C \leq 18)}$; and
R$_2$ is hydrogen, alkyl$_{(C \leq 12)}$, substituted alkyl$_{(C \leq 12)}$, cycloalkyl$_{(C \leq 12)}$, substituted cycloalkyl$_{(C \leq 12)}$, alkenyl$_{(C \leq 12)}$, substituted alkenyl$_{(C \leq 12)}$, alkynyl$_{(C \leq 12)}$, substituted alkynyl$_{(C \leq 12)}$, aryl$_{(C \leq 12)}$, substituted aryl$_{(C \leq 12)}$, aralkyl$_{(C \leq 12)}$, substituted aralkyl$_{(C \leq 12)}$, or a monovalent amino protecting group; and
(B) reacting the aminating compound prepared in step (A) in the presence of a rhodium catalyst and an acid to obtain a compound containing a N-heterocycloalkyl group wherein the N-heterocycloalkyl group contains 3 to 10 ring atoms and a bond is formed between a second carbon atom of the reactant compound and the nitrogen atom of the group of formula III.

2. The method of claim 1, wherein the reactant compound is further defined as:

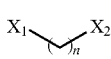

(V)

wherein:
X$_1$ is a reactive functional group;
X$_2$ is alkyl$_{(C \leq 18)}$, cycloalkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, alkoxy$_{(C \leq 18)}$, cycloalkoxy$_{(C \leq 18)}$, alkenyloxy$_{(C \leq 18)}$, alkynyloxy$_{(C \leq 18)}$, aryloxy$_{(C \leq 18)}$, aralkyloxy$_{(C \leq 18)}$, heteroaryloxy$_{(C \leq 18)}$, heteroaralkyloxy$_{(C \leq 18)}$, heterocycloalkoxy$_{(C \leq 18)}$, alkylamino$_{(C \leq 18)}$, dialkylamino$_{(C \leq 18)}$, cycloalkylamino$_{(C \leq 18)}$, dicycloalkylamino$_{(C \leq 18)}$, alkenylamino$_{(C \leq 18)}$, alky-nylamino$_{(C \leq 18)}$, arylamino$_{(C \leq 18)}$, aralkylamino$_{(C \leq 18)}$, heteroarylamino$_{(C \leq 18)}$, heteroaralkylamino$_{(C \leq 18)}$, heterocycloalkyl-amino$_{(C \leq 18)}$, or a substituted version of any of these groups; and
n is 1, 2, 3, 4, 5, 6, 7, or 8;
provided that the reactant compound does not contain a nonoxidized sulfur atom or a thiocarbonyl.

3. The method of claim 1, wherein the reaction conditions are Mitsunobu conditions.

4. The method of claim 1, wherein the N-heterocycloalkyl group contains 4 to 8 ring atoms.

5. The method of claim 4, wherein the N-heterocycloalkyl group contains 4 to 6 ring atoms.

6. The method of claim 1 further comprising reacting the substrate compound with the rhodium catalyst in a reaction mixture.

7. The method of claim 1, wherein the method comprises adding from about 0.05 mol % to about 10 mol % of the rhodium catalyst.

8. The method of claim 1, wherein the acid is R$_4$CO$_2$H; wherein:
R$_4$ is alkyl$_{(C \leq 8)}$, cycloalkyl$_{(C \leq 8)}$, or a substituted version of either group.

9. The method of claim 1, wherein the reactant compound comprises 6 carbon atoms to 24 carbon atoms.

10. The method of claim 9, wherein the reactant compound comprises 6 carbon atoms to 18 carbon atoms.

11. The method of claim 1, wherein the reactant compound does not contain a nonoxidized sulfur atom or a thiocarbonyl.

12. The method of claim 1, wherein the second aliphatic or aromatic group of the reactant compound is further defined as alkyl$_{(C \leq 18)}$, cycloalkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, alkoxy$_{(C \leq 18)}$, cycloalkoxy$_{(C \leq 18)}$, alkenyloxy$_{(C \leq 18)}$, alkynyloxy$_{(C \leq 18)}$, aryloxy$_{(C \leq 18)}$, aralkyloxy$_{(C \leq 18)}$, heteroaryloxy$_{(C \leq 18)}$, heteroaralkyloxy$_{(C \leq 18)}$, heterocycloalkoxy$_{(C \leq 18)}$, alkylamino$_{(C \leq 18)}$, dialkylamino$_{(C \leq 18)}$, cycloalkylamino$_{(C \leq 18)}$, dicycloalkylamino$_{(C \leq 18)}$, alkenylamino$_{(C \leq 18)}$, alkynylamino$_{(C \leq 18)}$, arylamino$_{(C \leq 18)}$, aralkylamino$_{(C \leq 18)}$, heteroarylamino$_{(C \leq 18)}$, heteroaralkylamino$_{(C \leq 18)}$, heterocycloalkyl-amino$_{(C \leq 18)}$, or a substituted version of any of these groups.

13. The method of claim 12, wherein the second aliphatic or aromatic group is cycloalkyl$_{(C \leq 18)}$, aryl$_{(C \leq 18)}$, or a substituted version of any of these groups.

14. The method of claim 1, wherein the aliphatic linker of the reactive compound is further defined as a methylene, ethylene, propylene, butylene, pentylene, or hexylene.

15. The method of claim 1, wherein the reactive functional group of the reactive compound is a tosyl, mesyl, trifluoromethanesulfonyl, hydroxy, mercapto, or halo.

16. The method of claim 15, wherein the reactive functional group of the reactive compound is a hydroxyl.

17. The method of claim 1, wherein the reactive group is an electron deficient aromatic ring.

18. The method of claim 1, wherein the reaction mixture comprises an organic solvent.

19. The method of claim 1, wherein the reaction mixture has a temperature from about 0° C. to about 100° C.

20. The method of claim 1, wherein the aminating compound is reacted with the acid and the rhodium catalyst for a time period from about 1 hour to about 3 days.

* * * * *